United States Patent [19]

Johnson et al.

[11] 4,189,431

[45] Feb. 19, 1980

[54] ALKINYL TERMINATING GROUPS IN BIOGENETIC-LIKE CYCLIZATIONS TO STEROIDS

[75] Inventors: William S. Johnson, Portola Valley, Calif.; Michael B. Gravestock, Bramhall, England

[73] Assignee: The Board of Trustees of Leland Stanford Junior University, Stanford, Calif.

[21] Appl. No.: 821,266

[22] Filed: Aug. 3, 1977

Related U.S. Application Data

[63] Continuation of Ser. No. 601,742, Aug. 4, 1975, Pat. No. 4,055,603, which is a continuation-in-part of Ser. No. 375,617, Jul. 2, 1973, abandoned, which is a continuation-in-part of Ser. No. 162,672, Jul. 17, 1971, abandoned.

[51] Int. Cl.$^2$ .............................................. C07C 71/00
[52] U.S. Cl. ........................ 260/239.55 R; 260/340.7; 260/340.9 AS; 260/397.45; 260/397.3; 260/397.4; 260/397.2
[58] Field of Search ...................... 260/239.55, 397.45, 260/617 R, 631 R, 340.7, 340.9

[56] References Cited

U.S. PATENT DOCUMENTS

| | | | |
|---|---|---|---|
| 3,884,945 | 5/1975 | Johnson et al. | 260/397.45 |
| 4,032,579 | 6/1977 | Johnson | 260/397.45 |

Primary Examiner—Elbert L. Roberts
Attorney, Agent, or Firm—Bertram I. Rowland

[57] ABSTRACT

Polyenine compounds are provided having the naturally occurring geometry and a group which in the presence of acid initiates a carbocation cyclization to a steroid or A-nor-steroid structure, particularly the pregnane parent structure. The compounds are formed for the most part by condensation of two units prepared from readily available small molecules and are joined to form a polyenine, usually having a substituted carbocyclic ring which upon contact with a Lewis acid catalyst (includes protonic) cyclizes directly to provide the 5-membered D ring as well as substitution at the C-20 position.

7 Claims, No Drawings

ALKINYL TERMINATING GROUPS IN BIOGENETIC-LIKE CYCLIZATIONS TO STEROIDS

CROSS REFERENCE TO RELATED APPLICATIONS

This is a continuation of application Ser. No. 601,742 filed Aug. 4, 1975, now U.S. Pat. No. 4,055,603, which application is a continuation-in-part of pending application Ser. No. 375,617, filed July 2, 1973, now abandoned, which was a continuation-in-part of application Ser. No. 162,672, filed July 17, 1971, now abandoned.

BACKGROUND OF THE INVENTION

1. Field of the Invention

Steroids play a significant biological role in the animal and vegetable kingdom in being a mediator in many biological processes. In addition, the steroids, because of their hormonal activity, have been a basis for the production of a wide variety of synthetic drugs, which differ in various structural ways from naturally occurring steroids and either mimic steroidal activities or provide new biological activity.

Because of the many inherent synthetic difficulties in modifying naturally occurring steroids and the uncertainties involved in depending upon sufficient supplies of naturally occurring steroids, particularly plant steroids, there has been increasing interest in providing synthetic routes to steroid products. Any synthesis of a steroid is complicated by the perhydrocyclopentanophenanthrene structure and the particular geometry of the structure as to the ring fusions. In adddition, the presence of bridgehead alkyl groups at C-10 and C-13 add additional complications. There is a further consideration of substituents which are frequently present at C-3 and C-17. Finally, there is the need that in each of the steps, particularly the latter steps, the desired geometry is retained and good yield of the desired products is obtained without the presence of only difficultly removable contaminants.

2. Description of the Prior Art

Johnson, Accounts of Chemical Research, 1968, discloses a wide variety of nonenzymic biogenetic-like olefinic cyclizations of polyunsaturated compounds using various groups which serve as sources of carbocations. Johnson, et al., J. Amer. Chem. Soc., 92, 4461 (1970) discloses the synthesis of polyenes which may be cyclized to a homosteroid having a 6-membered D ring. Johnson, et al., ibid, 93, 4330 (1971) discloses an acetylenic terminating group in the formation of bi and tricyclic compounds. Johnson, et al., ibid, 93, 4332 (1971) shows the formation of progesterone employing an intermediate having an acetylenic terminating group. Markezich, et al., ibid, 95, 4414 (1973) shows a cyclization to a pregnone structure employing a cyclohexenyl initiating ring and an acetylenic terminating group. McCarry, et al., ibid, 95, 4416 (1973) discloses cyclization of a polyenine compound to a pregnone structure which is then modified to progesterone. Use of nitroalkane to capture the vinyl carbonium ion which is formed at the acetylenic terminating group is described in Morton, et al., ibid, 95, 4417 (1973). Polyenines employing cyclohexenol as initiators is described in Carney, et al., ibid, 96, 2549 (1974). Use of an acetal as an initiating group is found in Johnson, et al., ibid, 96, 3979 (1974).

SUMMARY OF THE INVENTION

Novel intermediates for the formation of novel polyenine precursors are provided which can be cyclized by acid catalysis to a steroid or nor-steroid having the desired geometric configuration, as well as forming the 5-membered D ring directly. In addition, substitution can be provided at the C-20 position. Depending upon the choice of cyclization initiator which reacts with an acid to form a carbocation which initiates the cyclization, a 5- or 6-membered A ring may be formed directly. Products are therefore formed having the desired geometry, and, as desired, intermediates may be resolved to the naturally occurring stereoisomer, and upon cyclization the desired stereoisomeric steroid is obtained.

DESCRIPTION OF THE SPECIFIC EMBODIMENTS

Intermediates are provided for preparing polyenines which upon treatment with acids under relatively mild condition cyclize directly to A-nor or steroid structure, particularly pregnane structure having the desired geometry and having a substituent at the C-20 carbon atom which may be hydrocarbon or hetero. The precursor compounds which are employed as the intermediates for the cyclization will have at least 18 carbon atoms, usually at least 19 carbon atoms, and generally fewer than 50 carbon atoms, frequently fewer than 36 carbon atoms, and preferably fewer than about 30 carbon atoms. The cyclization precursor may be divided into three parts: (1) initiator (Z); (2) linking group (Y); and (3) terminator (X). In addition, upon cyclization the intermediate will react with a nucleophile (WH) which will be bonded at the C-20 position. The reaction is as follows:

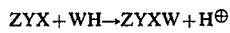

$$ZYX + WH \rightarrow ZYXW + H^\oplus$$

The cyclization precursor will have at least one chalcoxy group and may have as many as four chalcoxy groups, more usually having from 1 to 2 chalcoxy groups, normally as part of the initiator. (By chalcoxy is intended hydroxy, thiol, oxyether, and thioether, but not esters. The ether groups may be bonded to hydrocarbyl groups, which may be aliphatic, cycloaliphatic or aromatic, or combinations thereof, generally free of aliphatic unsaturation or substituted hydrocarbyl groups and heterocyclic groups, but will generally be bonded to hydrocarbyl groups.)

The description of the invention will be divided as follows:
I. Intermediates
II. Methods of Preparing Intermediates
III. Cyclization
IV. Tetracyclic Products
V. Reaction Charts
VI. Experimental
VII. Conclusion Before considering the various categories, a general discussion of the synthetic route and nature of the major fragments will be considered. In following a route whereby an internal double bond is formed which joins together the initiator and the terminator in a single molecule, it is necessary that the double bond formation result in the desired geometry. the group having the terminator will also have a double bond with the desired geometry, so that at the time of formation of the double bond in the terminator fragment, it is necessary to provide the desired geometry for that double bond. The remaining site of unsaturation is the double bond in the initiator, which is endocyclic when the initiator is a carbocyclic ring. The geometry is fixed for the carbocyclic initiator, while for the acyclic initiator the double bond must be formed with the proper geometry. Thus, the sequence of reactions must provide a cyclization precursor which has the plurality of double bonds, each one having the proper geometry to provide the desired ring fusions upon cyclization. During the course of the reaction, conditions must be provided which do not isomerize double bonds to an undesirable mixture containing both the desired and undesired geometry.

Where possible, it is desirable to resolve either one of the fragments or the cyclization precursor, so that upon cyclization an optically active product is obtained having the desired asymmetry. Depending upon the particular molecules involved, various sites offer the opportunity for an optically active center, e.g. C-5 and C-11. For resolution, it is necessary to have a functionality in the molecule which can be combined with an optically active material to form a diastereomer.

In addition, the terminating group should desirably form the 5-membered D ring directly, so that additional synthetic steps are not required in transforming the 6-membered D ring to the desired 5-membered D ring.

As indicated previously, the cyclization precursor has three parts: an inititaor (Z); a diene linking group (Y); and an acetylenic terminator (X). The initiator will be cyclic or acyclic and will have the following functionality as part of its structure:

wherein:

p is of from 2 to 3, being 3 when the broken line is not a bond;

f is a chalcoxy group; and the broken line indicates the presence of a bond when Z is cyclic and the absence of a bond when Z is acyclic.

The initiator has an allylic chalcogen atom when cyclic and a C-6 chalcogen atom to a $\Delta^1$ double bond when acyclic. The double bond is positioned to form a bond with the chalcogen substituted carbon atom in a 5 or 6 membered ring.

The linking group (Y) is a 5-substituted or unsubstituted deca-3,7-dien-1,10-ylene, which may be further substituted at the 7-position by a lower alkyl group (1–4 carbon atoms), particularly straight chained. The substituent at the 5-position will also be lower alkyl, e.g. methyl and will be the 11-position of the steroid. Other positions of the linking group may also be substituted, particularly lower alkyl substituted, e.g. methyl (when lower alkyl is referred to, it is intended alkyl of from 1 to 4 carbon atoms, unless otherwise specifically indicated).

The terminator (X) is an alkinyl or substituted alkinyl group of from 2 to 18 carbon atoms, more usually of from 2 to 6 carbon atoms, and preferably of from 3 to 4 carbon atoms, and may be substituted with chalcogen or silyl.

I. Intermediates

The cyclization precursor is a trienine having at least one chalcogen atom, and generally not more than 4 chalcogen atoms, usually having 1 to 3 chalcogen atoms, and more usually 1 to 2 chalcogen atoms. The intermediates will have at least 18 carbon atoms, more usually at least 19 carbon atoms, and generally not more than 50 carbon atoms, usually not more than 40 carbon atoms, and usually having from about 19 to 36 carbon atoms, preferably from about 19 to 30 carbon atoms. The trienine may be substituted with lower alkyl groups at any position having a saturated carbon atom, for example C-6 and C-11.

For the most part, the cyclization precursors will have the following formula:

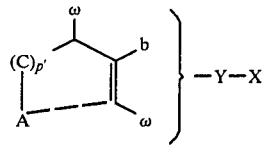

wherein:

one of the omegas ($\omega$) is a bond to —Y—X and is otherwise hydrogen;

b is hydrogen or alkyl of from 1 to 4 carbon atoms, more usually of from 1 to 2 carbon atoms, and usually straight chained;

p' is an integer of from 1 to 2;

A is an alkyl or alkylidene radical (depending on whether the broken line is a bond) of from 1 to 12 carbon atoms, more usually of from 1 to 7 carbon atoms having from 1 to 2 chalcoxy groups bonded to the carbon atom in the chain and may have an oxygen atom briding to the adjacent saturated carbon atom to form an epoxide; and the broken line indicates the presence or absence of a bond, depending upon whether the initiator is cyclic or acyclic.

The carbon atoms in the parenthesis may be substituted or unsubstituted, when substituted being substituted with alkylidene of from 1 to 4 carbon atoms, more usually of from 1 to 3 carbon atoms, or chalcoxy of from 0 to 6 carbon atoms, more usually of from 0 to 4 carbon atoms, and wherein 2 chalcoxy groups bonded to the same carbon atom may be taken together to form a cyclic ketal of from 5 to 6 annular members, there being a total of from 0 to 2 substituents on the carbon atoms in the parenthesis.

More particularly, the precursors to the tetracyclic compounds will have the following formula:

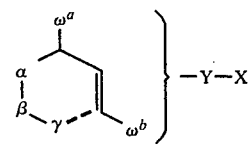

wherein:

the broken line is a bond when the group is cyclic and is not a bond when the group is acyclic;

$\alpha$ is methylene or a bond, being methylene when the broken line is not a bond;

$\beta$ is an aliphatic hydrocarbylidene group of a total of from 1 to 6 carbon atoms, more usually of from 1 to 4 carbon atoms having from 0 to 2 alpha-chalcoxy groups, wherein two chalcoxy groups may be taken together to form a cyclic ketal of from 5 to 6 annular members and having from 0 to 1 site of ethylenic unsaturation, or, with the proviso that the broken line is a bond, of the following formula $\omega^c$—CH<;

γ is alpha-chalcoxyhydrocarbyl having from 1 to 2 alpha-chalcoxy groups and being of from 1 to 10 carbon atoms, more usually of from 1 to 8 carbon atoms and free of aliphatic unsaturation and includes alkyl, cycloalkyl and phenyl substituents on the carbon atoms in the chain, and wherein an oxygen atom may bridge to β to form an epoxy group;

when the broken line is a bond, γ is usually alkylidine of from 1 to 6 carbon atoms, more usually of from 1 to 4 carbon atoms and having from 1 to 2 alph-chalcoxy groups which may be taken together to form a cyclic ketal of from 5 to 6 annular members, and when the broken line is not a bond, γ will be hydrocarbyl having from 1 to 2 alpha-chalcoxy groups which may be taken together to form a cyclic acetal or ketal of from 5 to 6 annular members and is of from 1 to 8 carbon atoms, more usually of from 2 to 8 carbon atoms and free of aliphatic unsaturation, and wherein one of the chalcoxy groups may be taken together with β to form an epoxide ring;

b is hydrogen or lower alkyl of from 1 to 4 carbon atoms, more usually of from 1 to 3 carbon atoms, and preferably of from 1 to 2 carbon atoms and is straight chained; and one of $\omega^{a-c}$ is a bond to Y and is otherwise hydrogen;

Y is 5-e-7-a-3,7-decadien-1,10-ylene, where the 1-position is bonded to Z and the 10-position is bonded to X and is of the formula:

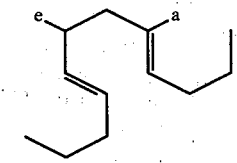

wherein:

a is hydrogen or lower alkyl, usually of from 1 to 3 carbon atoms and preferably of from 1 to 2 carbon atoms, particularly methyl, and usually straight chained;

e is hydrogen or loweralkyl, particularly alkyl of from 1 to 2 carbon atoms, e.g. methyl, usually having the alpha-configuration; and X is of the formula:

$$\overset{R^1}{\underset{|||}{|}}$$

wherein:

$R^1$ is hydrogen, saturated alphatic hydrocarbon of from 1 to 3, usually 1 to 2 carbon atoms, having from 0 to 1 oxy or halo group (oxy being of from 0 to 6 carbon atoms); lower alkyl, usually of from about 1 to 3, more usually of from 1 to 2 carbon atoms, particularly methyl and ethyl, hydroxy-(lower alkyl), particularly protected hydroxy(lower alkyl), e.g. ethers and esters of from 1 to 8, more usually 1 to 6 carbon atoms, haloalkyl, particularly halomethyl, where halo is fluorine, chlorine or bromine; or tri-(lower alkyl)silyl.

(Unless otherwise indicated, when referring to a carbon as for example, C-5, in the cyclization precursor, it is intended that the carbon atom will ultimately be at the C-5 position of the steroid product.)

For the most part, the cyclic compounds of this invention will have the following formula:

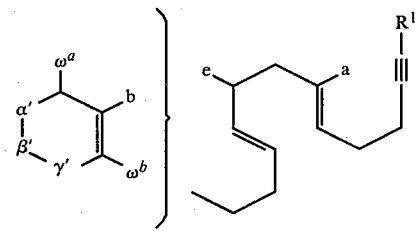

wherein:

a and b are hydrogen or lower alkyl, more usually of from 1 to 3 carbon atoms, and preferably of from 1 to 2 carbon atoms, particularly methyl with a preferably being alkyl;

$R^1$ is alkyl, oxyalkyl, particularly protected oxyalkyl, e.g. acylcarboxyalkyl and hydrocarbyloxyalkyl, of from 1 to 8 carbon atoms, more usually of from 1 to 6 carbon atoms, preferably of from 1 to 4 carbon atoms, particularly preferred of from 1 to 2 carbon atoms, particularly methyl, hydroxymethyl and protected hydroxymethyl;

e is hydrogen or lower alkyl, particularly methyl, and more particularly methyl of the alpha-configuration;

α' is a bond or methylene;

β' is alkylidene of from 1 to 8, more usually of from 1 to 6, and preferably of from 1 to 4 carbon atoms, having from 0 to 2 chalcoxy groups bonded to the annular carbon atom, wherein two chalcoxy groups may be taken together to form a cyclic ketal of from 5 to 6 annular members and having from 0 to 1 site of ethylenic unsaturation, particularly exo unsaturation, that is, a double bond to the annular carbon atom, or of the formula $\omega^c$—CH<;

γ' is alpha-chalcoxyalkylene of from 1 to 8, more usually 1 to 6 and preferably 1 to 4 carbon atoms having from 1 to 2 chalcoxy groups bonded to the annular carbon atom, wherein two chalcoxy groups may be taken together to form a cyclic ketal of from 5 to 6 annular members; and wherein one of $\omega^{a-c}$ is a bond, but are otherwise hydrogen.

When Z is acyclic, the compounds for the most part will have the following formula:

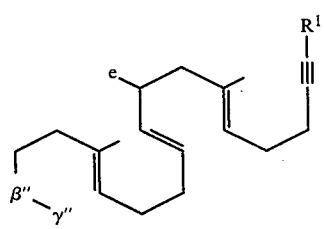

wherein:

a, b, e and $R^1$ have been defined previously;

β" is an aliphatic hydrocarbylidene group having from 0 to 2 alpha-chalcoxy substitutents and from 0 to 1 site of ethylenic unsaturation, particularly $\Delta^1$ and is of 1 to 8 carbon atoms, more usually of from 1 to 6 carbon atoms, and preferably of from 1 to 4 carbon atoms, and usually methylene and may be taken together with γ" to form an epoxide ring; and γ" is chalcoxymethyl of from 1 to 12 carbon atoms, more usually of from 1 to 10 carbon atoms, preferably of from 1 to 8 carbon atoms, and more preferred of from 1 to 5 carbon atoms, having from 1 to 2 alpha-chalcoxy groups, where 2 alpha-chalcoxy groups may be taken together to form a cyclic ketal of from 5 to 6 annular members and one chalcoxy group may be taken together with β" to form an epoxide ring; γ" may be substituted with aliphatically saturated hydrocarbyl groups—alkyl, cycloalkyl, or carbocyclic aryl groups—of from 1 to 8 carbon atoms, more usually of from 1 to 6 carbon atoms and when other than aryl, of from 1 to 2 carbon atoms, particularly methyl.

The following are a number of reactions for preparing a wide variety of initiator groups, indicating literature sources for the reaction conditions where appropriate.

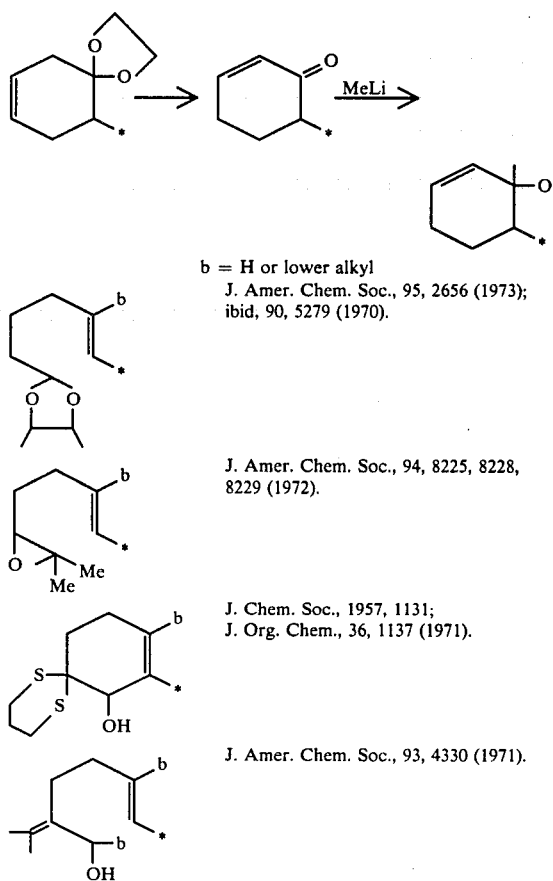

b = H or lower alkyl
J. Amer. Chem. Soc., 95, 2656 (1973); ibid, 90, 5279 (1970).

J. Amer. Chem. Soc., 94, 8225, 8228, 8229 (1972).

J. Chem. Soc., 1957, 1131; J. Org. Chem., 36, 1137 (1971).

J. Amer. Chem. Soc., 93, 4330 (1971).

(The * indicates the site of attachment.)

In addition to the illustrative initiators indicated above, other initiators may be prepared where allylic chalcoxy groups are present or a chalcoxy group is at the C-6 position in relation to a Δ¹-double bond. The significant factor is that the chalcoxy group is situated so that in the presence of acid a carbonium ion is formed which can interact with a double bond to form a 6-membered ring, either the A or B ring depending upon whether the initiator is cyclic or acyclic.

II. Method of Preparing Intermediates

The intermediates described in Section I are prepared by the condensation of two units, which provides for the $\Delta^3$ double bond of Y. The double bond is introduced by condensation between a phosphonium ion and an aldehyde under Schlosser-Wittig conditions. The condensation provides for trans geometry, so that the desired ring geometry is obtained upon ring fusion.

The preparation of the various fragments which contain the Z group for condensation with the aldehyde has appeared in a number of references and will be further disclosed in the experimental section. The following publications are therefore cited to demonstrate the synthesis of a number of different Z group containing fragments.

Johnson, Accounts of Chem. Research, 1968, 1; Johnson, et al., J. Am. Chem. Soc., 90, 299 (1968); Johnson and Schaaf, Chemical Comm., 1969, 671; Abrams, et al., Bioorganic Chemistry, 1, 243 (1971); Johnson, et al., J. Am. Chem. Soc., 93, 4332 (1971); Johnson, et al., ibid, 92, 4461 (1972). U.S. Pat. Nos. 3,558,672 and 3,598,845, and German Offenlegungsschrift Nos. P2234018.7 and P2418877.0.

The Schlosser-Wittig reaction combines in an ethereal solvent approximately equimolar amounts of a trihydrocarbyl ylide, particularly the triphenylphosphonium ylide, with the appropriate aldehyde. An ethereal solvent is employed, e.g. tetrahydrofuran, diethyl ether, dimethoxyethylene and combinations thereof. The temperature will normally be about −90° to −50° C. and the concentration of reactants will generally be from about 0.05 to 1M, usually from about 0.1 to 0.5M. Carbocyclicaryl lithium, e.g. phenyl lithium is added in at least about equimolar amount and usually in excess, ranging from about 1 to 2 moles per mole of ylide-aldehyde reactant. The temperature is allowed to rise to from about −50 to −10° C. and after a sufficient time, e.g. 5 minutes to 1 hour, the reaction is quenched, e.g. by addition of a lower alkanol, for example methanol. The product may then be isolated and purified according to conventional procedures.

Flow sheets are set forth consequently which indicate the course of the reaction. In Flow Sheets 1 and 2, two separate modes of preparing 9-$R^1$-4-methylnon-4-enal are set forth. In Flow Sheet 1, by using an ortho ester other than ortho acetate, a hydrocarbyl group may be introduced at the carbon atom which will ultimately provide the C-11 position. This compound will have the following formula:

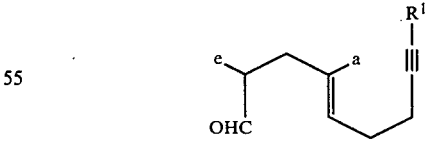

wherein:
a and e are hydrogen or lower alkyl, and $R^1$ has been defined previously.

Flow Sheet 3 provides for the preparation of a cyclic initiator, where the chalcoxy group is a cyclic thioketal, which if desired, may be hydrolyzed to the ketone and reduced to an hydroxyl chalcoxy group, which may serve as the intiator.

In Flow Sheet 4 is depicted a sequence which provides an initiator precursor. The diketal, where n is 2 or 3, is initially employed as the intermediate for the condensation with the aldehyde. Subsequently, as shown in Flow Sheet 6, the ketals may be hydrolyzed to the diketone, which may then be condensed to a cyclopentenone, which upon condenation with a methyl carbanion reagent forms the tertiary allylic alcohol.

It should be noted that in preparing the various compounds, chiral carbon atoms will be introduced. While the reaction can be carried out to provide racemic product, it may be advantageous in many situations to resolve one of the intermediates at an early stage, so that upon cyclization, an optically active product is obtained. The choice as to the compound to be resolved will depend to a significant degree upon the manner of synthesis, the chemical inertness of the chiral center, the ease of resolution, and the like.

In Flow Sheet 5 is shown the course of the reaction employing a cyclohexenone ethylenedithioketal which is used to form cyclohexenol which serves as the initiator. The dithioketal derivative is first condensed with the aldehyde group and then transformed to the alcohol.

By appropriate choice of reagents during the preparation of the intermediates, intermediates may be prepared which upon cyclization will afford a variety of substituents at various positions on the steroid nucleus. The opportunity to introduce a substituent at the 11-position has already been indicated, whereby an ortho ester is employed which is a homologue of orthoacetate. The following are illustrative examples of various procedures for introducing substituents at particular sites on the steroid nucleus.

Substitution in the A ring can be controlled by the choice of the cyclization initiator. For alkyl substitution at the C-1 position, Hagemann's ester may be alkylated at the alpha-vinyl carbon atom and the ester employed for formation of the desired phosphonium ylid or aldehyde. Alkylation at the 2-position can be accomplished by condensation of an alkyl metal compound with the appropriate ketone. Alkyl substitution at the 4-position can be provided, for example by employment of the acyclic initiator, with the appropriate groups bonded to the carbon atom which will ultimately provide the 4-position.

Alkyl substitution at C-6 and C-7 is accomplished by introducing the appropriate groups on the ethylene group bonded to the cyclization initiator ring. For example, where the ethylene group is bonded to a carboxylic acid, alpha-alkylation may be carried out. Alternatively, the ethylene group can be built up with introduction of the particular substituents.

Substitution on the C ring at C-12 can be achieved with the appropriate choice of the Grignard reagent 4 Flow Sheet 1.

Finally, substitution on the D ring is achieved by substituting the appropriate alkine groups with alkyl substituents at the carbon atoms which will ultimately provide C-15 and C-16. For example, a 4-substituted-but-4-ynyl Grignard reagent may be combined with ethylene oxide and the resulting alcohol oxidized to an aldehyde. The product may then be used as described previously. For the C-15 substituent, the aldehyde described above may be alpha-alkylated.

Substitution at the bridgehead carbon atoms C-10 and C-13 have already been described. As for substitution at C-5 and C-14, substitution at C-5 is achieved by the appropriate choice of cyclization initiator, while substitution at C-14 can be achieved by condensation of an alkyl metal, e.g. alkyl Grignard reagent, with oct-2-yn-7-en-6-one to produce the desired alcohol, which may then be used in manners previously described.

III. Cyclization

The cyclization is carried out in a protic or aprotic solvent in the presence of a Lewis acid (includes protonic) and optionally in the presence of a nucleophile other than supplied by the solvent or Lewis acid. The solvent and nucleophile may be the same or different, and when a solvent is employed in combination with the nucleophile, the solvent will normally be inert and aprotic.

A wide variety of solvents may be employed, which may be used by themselves or in combination with a nucleophilic reagent. Particularly useful solvents are halocarbon, both chloro and fluoro, normally of from 1 to 8 carbon atoms, and varying from monosubstituted to persubstituted and having from 0 to 1 site of ethylenic unsaturation, particularly when polyhalo substituted. Illustrative solvents include methylene chloride, 1,2-dichloroethane, 1,1-dichloroethylene, 1,1-difluoroethane, hexafluorobenzene, perfluoromethylcyclohexane, 1,1,2-trichloro-1,2,2-trifluoroethane, etc. Haloethers may also be employed, such as perfluoro-2-butyltetrahydrofuran, bis-2,2-trifluoroethyl ether, etc. Saturated hydrocarbons may also be employed such as hexane, heptane, cyclohexane, etc.

The nucleophile, which may also serve as the solvent, has a pair of electrons which may coordinate with a carbocation to form a covalent bond, e.g. a Lewis base, particularly a Bronsted base. The nucleophiles, which are employed, are relatively weak nucleophiles and include carbocyclic aromatics, e.g. benzene, toluene, anisole, etc.; olefinic hydrocarbons of from about 4 to 10 carbon atoms, e.g. 1-pentene, 2-pentene, isohexene, 1-heptene, 2-heptene, styrene, etc.; nitroalkanes of from about 1 to 6 carbon atoms having an alpha-hydrogen, e.g. nitromethane, 1-nitropropane, 2-nitropropane, etc.; water and fluorinated alcohol, e.g. 2,2,2-trifluoroethano, s-hexafluoroisopropanol, 2,2,3,3-pentafluoropropanol, etc. A peculiar nucleophile which forms a stable carbocation or orthoester is the cyclic esters of carbonic acid, e.g. ethylene carbonate.

The solvents and nucleophiles will normally have the following properties: (1) relatively low boiling point; (2) remain liquid in the reaction mixture at the reaction temperature; (3) provide some solubilization of the reactants; and (4) not undergo acid catalyzed reactions under the reaction conditions except with the cyclization precursor.

A wide variety of acidic catalysts may be used. For the purposes of this invention, Lewis acid shall include both protic and aprotic catalysts. The protonic catalysts are strong acids, preferably carboxylic acids, having pK in an aqueous solution of less than 4, preferably less than about 2. Illustrative strong protonic acids include trifluoroacetic acid, trichloroacetic acid, formic acid, etc. Illustrative aprotic Lewis acids include stannic chloride, titanium tetrachloride, zinc chloride, zinc bromide, boron trifluoride, etc.

The choice of acidic catalyst will affect the course of the reaction in that it may act as a nucleophile as well as a catalyst. The protonic catalyst may compete with nucleophilies present in solution to form vinyl esters, e.g. trifluoroacetate esters when trifluoroacetic acid is employed. The metal halides, particularly chlorides and bromides, will act to provide halide as a nucleophile.

Thus, vinyl halides will be formed. Where a variety of nucleophiles are present, such as the acid catalyst and an independent nucleophile, large excesses of the nucleophile will be required in order to insure a particular product. However, in many instances subsequent reactions, such as hydrolysis, will lead to the same product irrespective of the particular nucleophile which was involved with the carbocation.

Depending upon the particular initiating group, certain types of catalysts will be preferred. Where a thioether is involved, such as a thioketal, metal halide Lewis acids are the preferred catalysts. With an oxyether, either protonic or metal halide Lewis acid type catalysts may be employed. Where a nitroalkane is employed as the nucleophile, normally protonic catalysts will be employed.

The concentration of the cyclization precursor can be varied widely, although relatively dilute solutions will be employed to minimize the opportunity for polymerization. Generally the concentrations range from about 0.005M to 0.5M, more usually from about 0.001 to 0.1M, and preferably from about 0.01 to 0.05M. The acid concentration will vary depending upon the particular acid catalyst. With metal halide catalyst, a concentration may be as low as about 0.005M, and will generally not exceed about 0.5M, more usually being from about 0.01 to about 0.25M. With protonic catalysts, the molarity may be substantially higher, usually being as high as 2M, more usually up to about 1.5M, and usually not less than about 0.1M, more usually not less than about 0.2M. Usually, there will be at least one equivalent of acid per mole of cyclization intermediate, generally not exceeding about 50 moles of acid catalyst per mole of cyclization precursor. The metal halide Lewis acids will generally have equivalent ratios of from about 1 to 10.

The nucleophile when used as an auxiliary with a solvent will generally be used in large molar excess in relation to the cyclization precursor. Normally, the nucleophile will be used in at least about 5 moles per mole of cyclization precursor and may be as high as 100 moles per mole or higher. Conveniently, the mole ratio of nucleophile to cyclization precursor will generally be from about 10–50:1.

Mild temperatures will normally be employed, generally not exceeding 10° C. and may be as low as −50° C., more usually being from about −30° to 0° C. The time will vary as required, generally being at least about 5 minutes and usually not exceeding about 6 hours, more usually being from about 15 minutes to about 200 minutes. The particular time will vary depending upon the stability of the final product, the time being chosen to optimize the yield.

While the discussion has been primarily directed toward the preparation of steroids, the use of an acetylenic terminator is novel and can be used with the initiator Z, whenever it is desired to prepare a polycyclic compound having at least one 5-membered ring which has a functionality substituted on the ring. Thus, a variety of bi, tri, tetra and higher polycyclic compounds may be prepared, where the polycyclic structure involves at least one cyclopentane ring. In addition, depending upon the choice of substituent on the acetylene group, as well as the nucleophile, the cyclopentane ring may be substituted with an alpha-oxyalkylidene, acyl, both oximino and hydroxyalkyl at the same carbon atom, alkenyl or oxyalkenyl of a variety of chain lengths, arylalkyl, etc. The cyclization precursor will for the most part have the following formula:

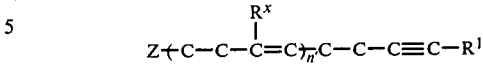

wherein:

Z and $R^1$ are as defined previously, usually saturated aliphatic hydrocarbyl of from 1 to 2 carbon atoms having 0 to 1 oxy or halo functional group, $R^x$ is hydrogen or alkyl of from 1 to 3, usually 1 to 2 carbocations, e.g. methyl, and the remaining valences of the carbon atoms may be unsubstituted (bonded to hydrogen) or substituted with alkyl substituents, particularly from 1 to 4 carbon atoms, more usually of from 1 to 2 carbon atoms, and preferably methyl. In the butenylene groups, the third carbon atom will normally be a bridgehead carbon atom and alkyl groups are more likely to be present there. In addition, the trans-configuration for the ethylenic groups is preferred. $n'$ is 0 or greater depending upon the number of rings, usually being from 0 2.

The bicyclic compounds are particularly useful as precursors to vitamin D.

In the experimental section a number of reactions are illustrated which demonstrate the formation of bicyclic and tricyclic species, in addition to the tetracyclic steroid species. As a matter of convenience, the 5-membered ring derived by including one of the acetylenic carbons will be referred to as D, the 6-membered ring fused to the 5-membered ring as C, the ring fused to the C ring as B and the remaining ring as A, depending upon the number of fused rings.

IV. Tetracyclic Products

The cyclic products which are formed in accordance with the subject invention will have from about 19 to 45 carbon atoms, usually from about 19 to 36 carbon atoms, more usually from about 20 to 36 carbon atoms.

For the most part the tetracyclic products of this invention will have the following formula:

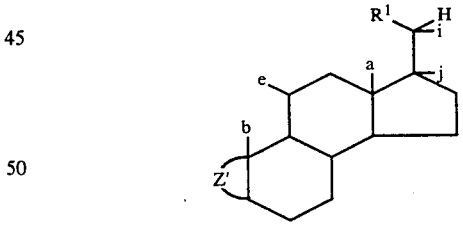

wherein:

$R^1$, a, b and e have been defined previously;

$Z'$ is the product resulting from the protonation of the cyclization initiator and will have shifted the double bond to the site of the chalcoxy group, wherein a single chalcoxy group will be lost, while two chalcoxy groups bonded to the same carbon atom will have one remaining chalcoxy group bonded to the carbon atom, which will be vinyl;

h will be determined by the particular nucleophile. Where the nucleophile involves C-C unsaturation, e.g. carbocylic aromatics and alkenes, h will be the alkenyl group or oxy-substituted (including esters) alkenyl or aryl, and i and j will be taken together to form a double bond; where h is an oxy group (ethers and esters) i and j will be taken together to form a double bond; h and i may be taken together to form oxo, for example where water is present or is introduced during the workup, and j will be hydrogen or oximino, where a nitroalkane has been employed as the nucleophile; h can also be halogen, particularly chloro and bromo, wherein i and j will be taken together to form a double bond.

As previously indicated various positions on the tetracyclic ring may be substituted with alkyl groups, by appropriate substitution of the intermediates during the synthesis of the cylization precursor.

Where a cyclopentenol has been used as the cyclization initiator, the cyclization product will have the following formula:

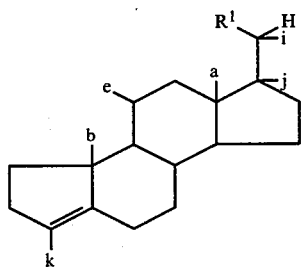

wherein:

all the symbols have been defined except k, and k will normally be alkyl of from 1 to 4 carbon atoms, more usually of from 1 to 2 carbon atoms, preferably methyl and usually straight chained.

Upon oxidation the A-nor-steroid will have the A ring opened and, if i and j are a double bond, will also cleave the double bond at C-17 (20) to give one of the following products:

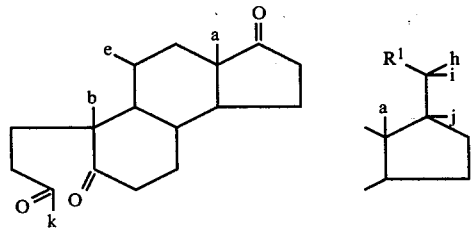

wherein:

all the symbols have been defined previously.

Upon keto-condensation, the 6-membered ring will be formed, and any vinyl halide or oxy derivative at C-20 will be hydrolyzed to form the oxo group, so that the product will have the following formula:

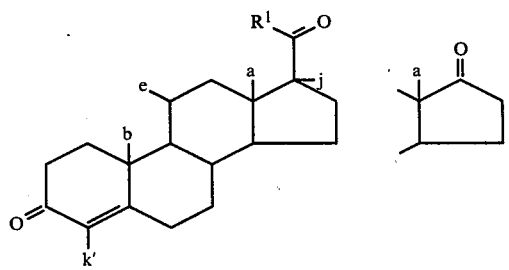

wherein:

with the exception of j' and k' all of the symbols have been defined previously; and k' is hydrogen when k was methyl, and alkyl of one fewer carbon atom when k was other than methyl, and j' is hydrogen, hydroxyl, or hydroxamic ether when j was oximino.

When a 6-membered cyclization initiator is employed, the products for the most part will have the following formula:

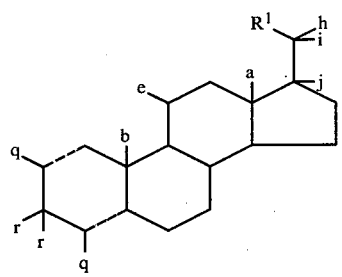

wherein:

$R^1$, a, b, e, h, i and j have all been defined previously; only one of the broken lines is a double bond;

the q bonded to the vinyl carbon atom is hydrogen or beta- or gamma-hydrochalcoxy-(hydroxy or thiol)-alkylene-chalcoxy of from 2 to 6, more usually of from 2 to 3 carbon atoms, but is hydrogen when bonded to the saturated carbon atom; and the two r's are taken together to form alkylidene of from 1 to 4 carbon atoms or dichalcoxy which are taken together to form a ring of from 5 to 6 annular members and from 2 to 6, more usually 2 to 3 carbon atoms.

The resulting tetracyclic products prepared by the acid catalyzed cyclization may be modified in a variety of ways. As already indicated, the C-17 (20) double bond may be oxidatively cleaved to provide a C-17 oxo group. Carbonyl groups may be introduced, for example, at C-3 by known procedures. Similarly, C-4 ethylenic unsaturation may be introduced into the A ring. Thus, various techniques may be employed, whereby cholestane, pregnane, androstane, or other steroidal structures may be provided.

V. Flow Sheets

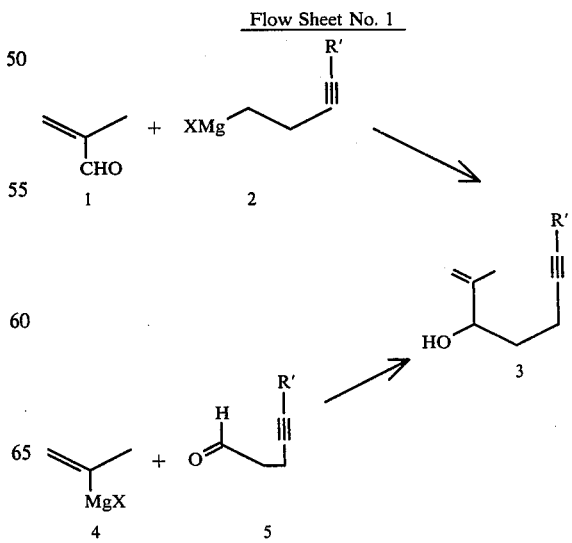

4,189,431
15
-continued
Flow Sheet No. 1
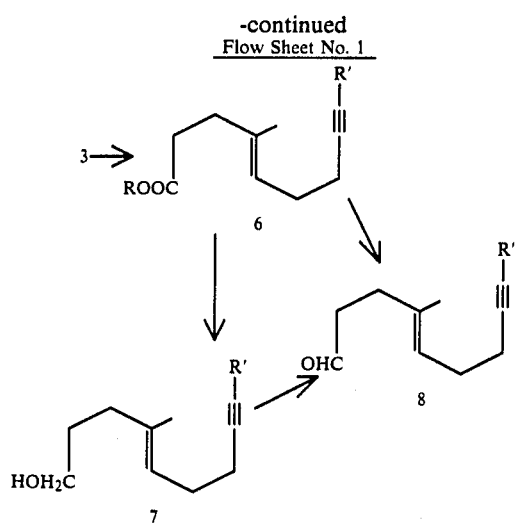
16
-continued
Flow Sheet No. 3
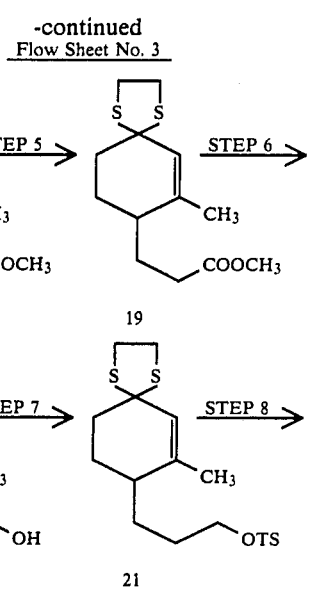
Flow Sheet No. 2
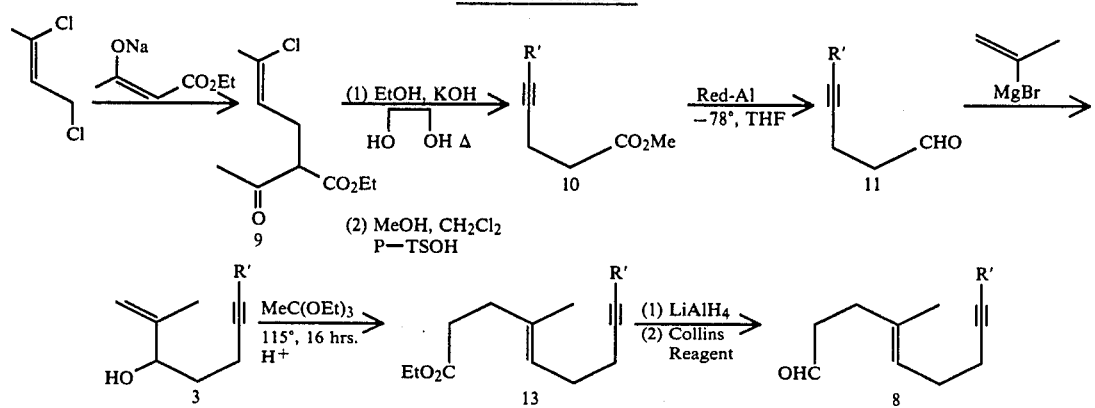
Flow Sheet No. 3
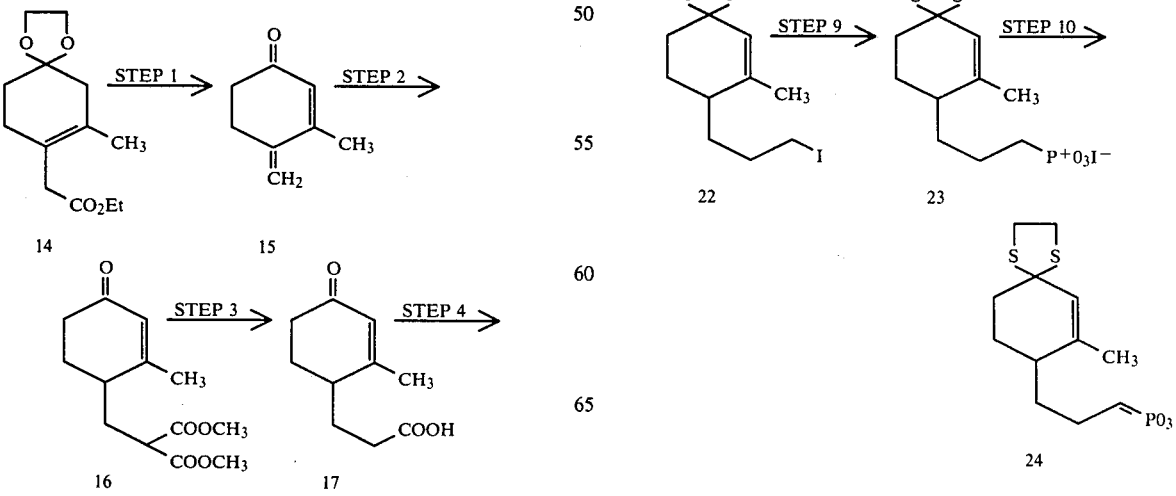

4,189,431
Flow Sheet No. 4
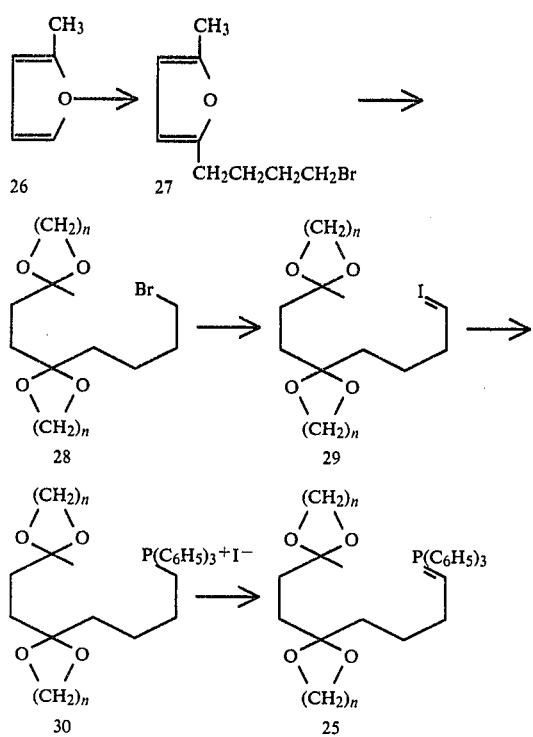
Flow Sheet No. 5
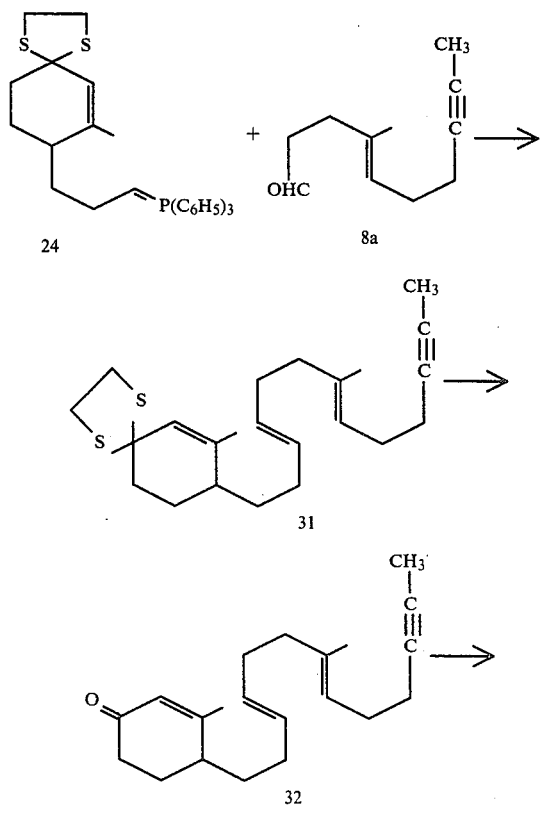
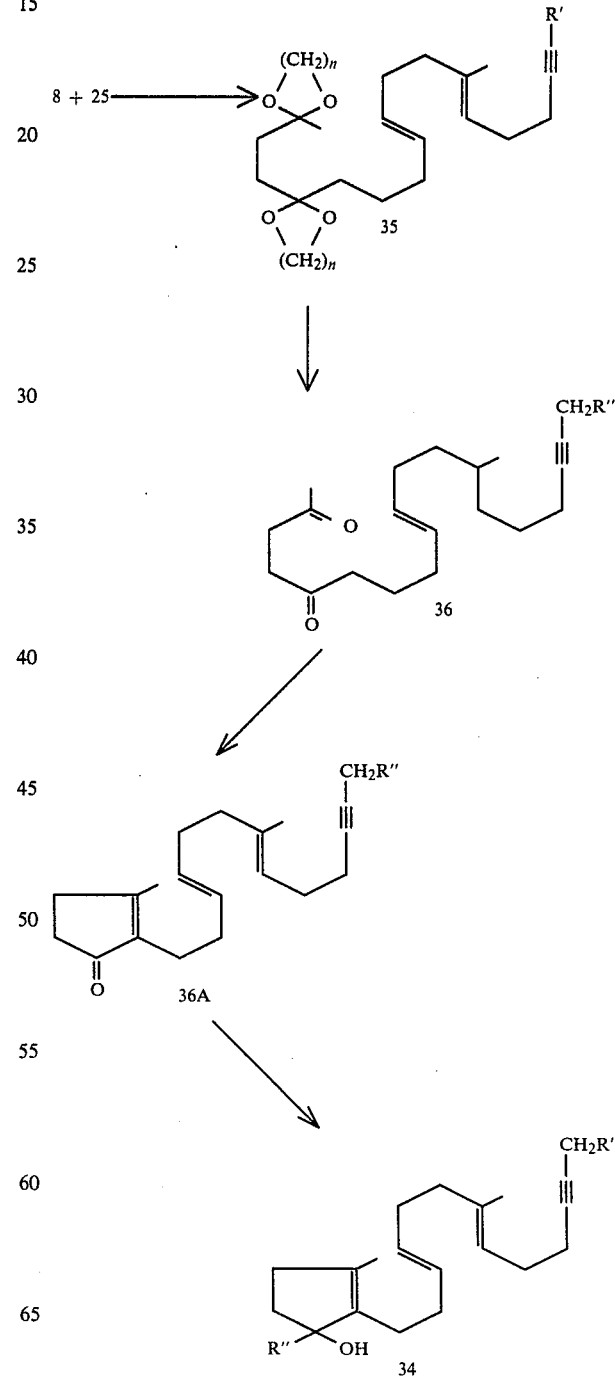

Flow Sheet No. 7
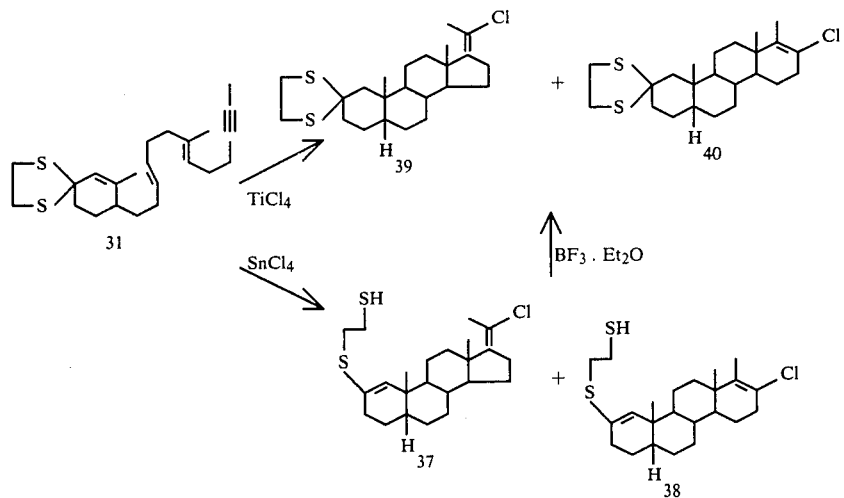
Flow Sheet No. 8
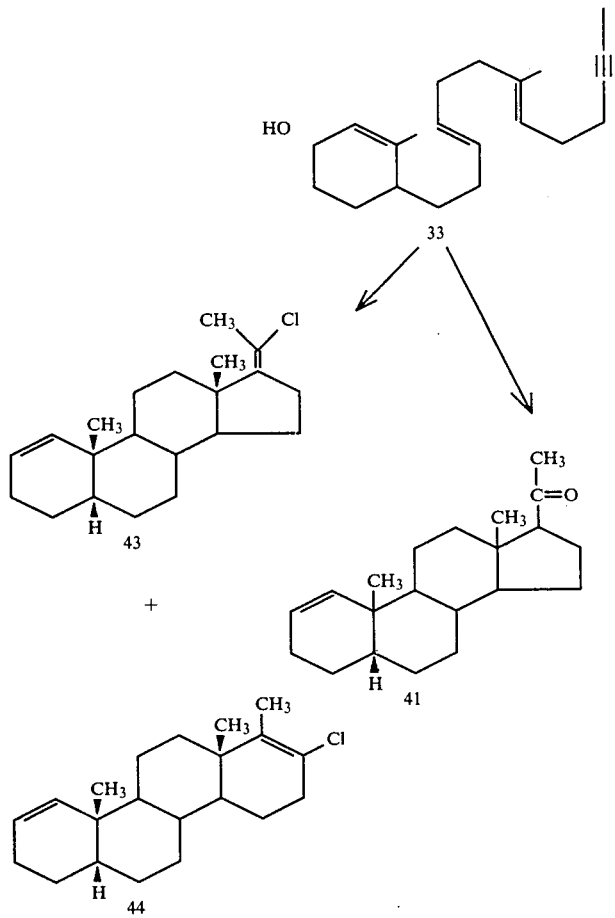

21
4,189,431
22
Flow Sheet No. 9
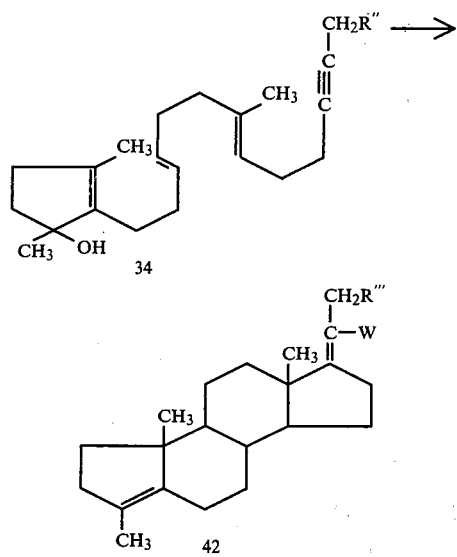
34
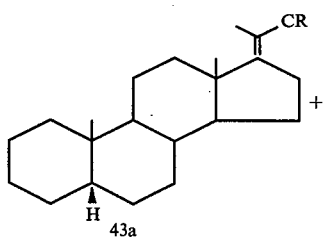
Flow Sheet No. 9A
37/38 ⟶ 43/44 ⟶
-continued
Flow Sheet No. 9A
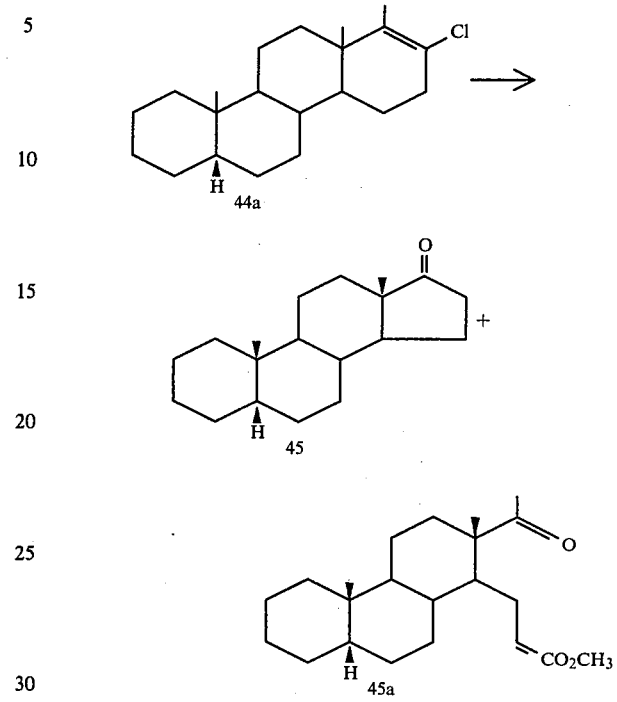
Flow Sheet No. 10
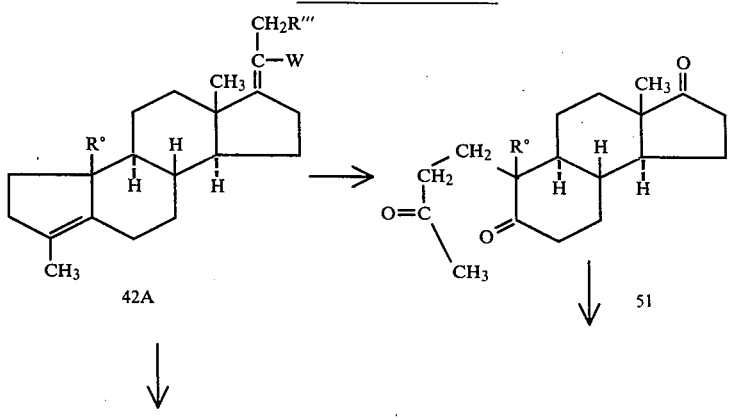

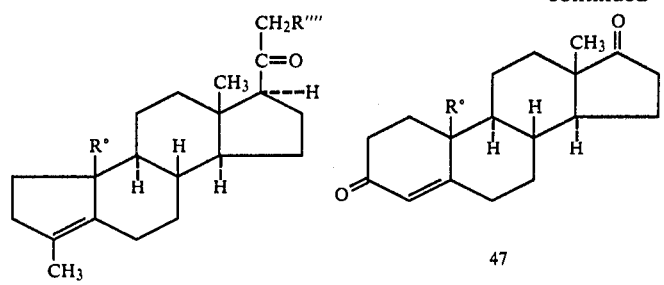
49
47
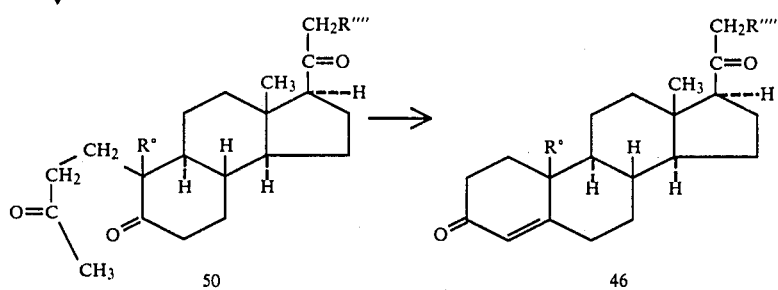
50
46
Flow Sheet No. 11
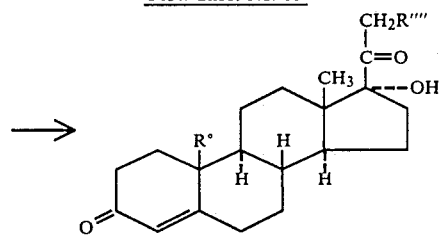
48
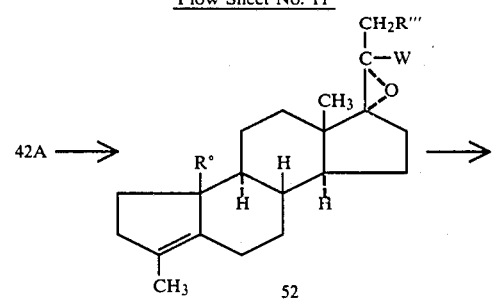
52
Flow Sheet No. 12
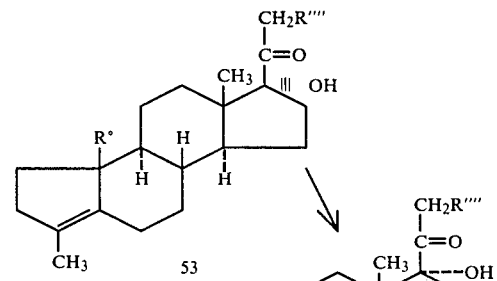
53
41
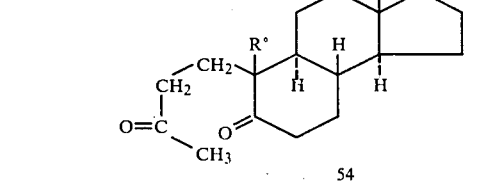
54
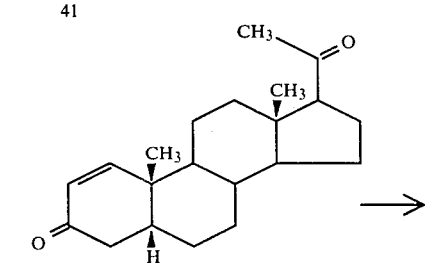
55

-continued
Flow Sheet No. 12

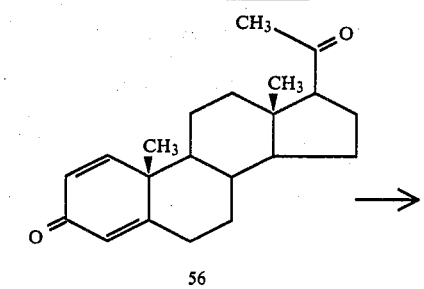

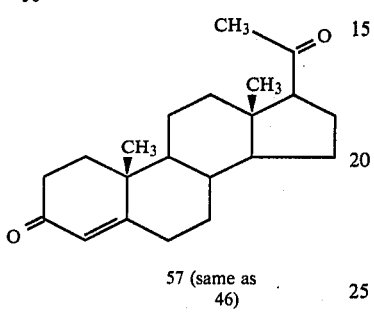

R° = CH₃; R'''' = H)

Flow Sheet No. 13

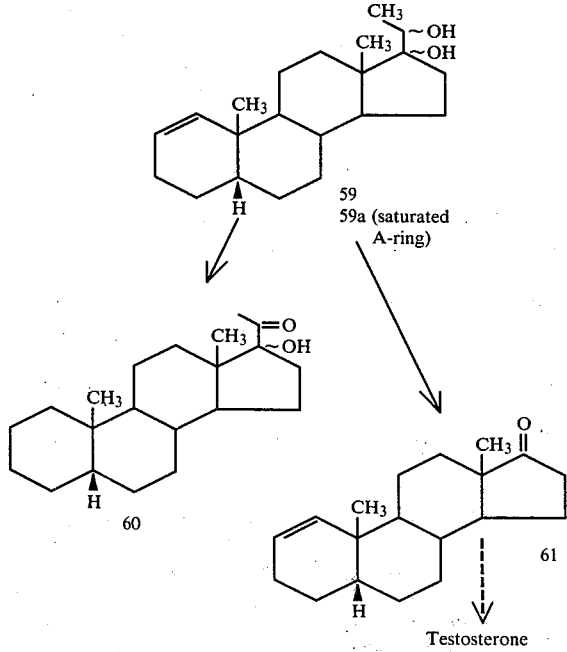

Flow Sheet No. 14

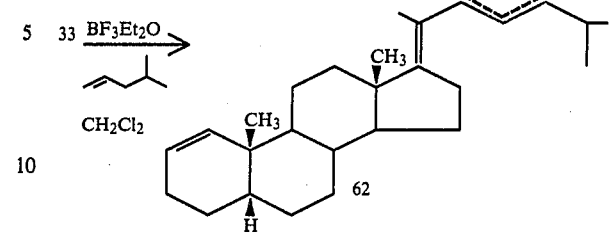

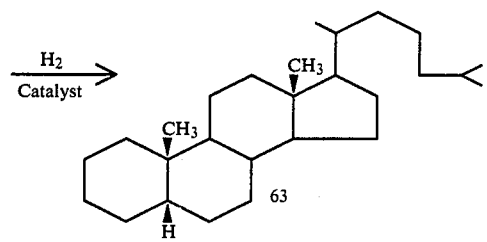

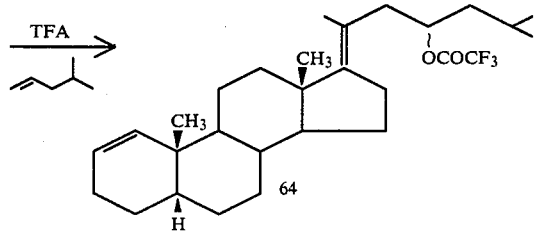

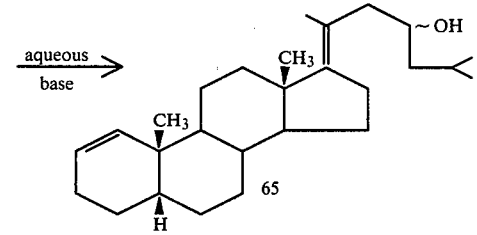

VI. Experimental

The following examples are offered by way of illustration and not by way of limitation. (All temperatures not otherwise indicated are in Centigrade. All percents not otherwise indicated are by weight. The phrase "worked up in the usual manner" means the organic layer is washed with brine, dried over anhydrous magnesium sulfate, filtered, and the solvent removed in vacuo. Where a number is indicated with a compound, it relates with a number in an earlier chart.)

In the following examples, except where otherwise stated, all compounds having chiral carbon atoms were prepared in the dl form. The same procedures apply to preparation of optically active forms provided resolution is accomplished at a suitable stage. For the sake of simplicity, the conventional wedges (to indicate the β-configuration) and dotted lines (to indicate the α-configuration) at positions such as C-5, C-10, etc. are sometimes omitted and it will be understood that the placement of H, CH₃ etc. at these positions is as in the natural steroids, the exception being that in those instances where the C-5 hydrogen or substituent is in the β-configuration it is so indicated. In general, the steric configuration at C-17-are also shown.

The following examples will serve further to illustrate the practice and advantages of the invention.

EXAMPLE 1—Synthesis of Aldehyde 8

Referring to Flow Sheet I, the unsaturated alcohol 3 ($R^1$ is methyl or tri-lower-alkylsilyl) is prepared by a Grignard reaction between methacrolein (1) and $XMgCH_2CH_2C\equiv CR^1$ (2) (X is chlorine, bromine or iodine) or the alternative reaction between $CH_2=C(CH_3)MgX$ (4) $R^1-C\equiv C(CH_2)_2CHO$ (5). The unsaturated alcohol 3 is then converted by the orthoacetate Claisen reaction (see Johnson et al J.A.C.S., 92, 741 (1970) with a lower alkyl orthoacetate, $CH_3C(O\text{-lower-alkyl})_3$ to the enyne ester 6. The latter is subjected to metal hydride reduction, as with lithium aluminum hydride, to afford the enyne alcohol 7. The alcohol can then be oxidized with an oxidizing agent capable of oxidizing primary alcohols to aldehydes, for example, with dipyridine-chromium (VI) oxide complex to the corresponding aldehyde 8. Alternatively, it has been found possible to effect selective reduction of the ester 6 with sodium bis (2-methoxy-ethoxy) aluminum hydride to give a mixture containing predominantly the aldehyde 8 with smaller amounts of alcohol 7.

Alternatively, the procedure of Flow Sheet No. 2 may be employed to synthesize the aldehyde 8.

Examples 36–38 provide details of these syntheses and Example 1a provides details of the synthesis of aldehyde 8a,

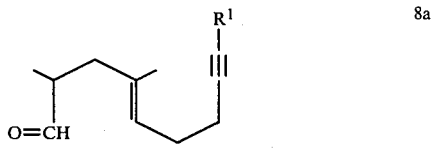

8a

EXAMPLE 1a—Synthesis of Aldehyde 8a ($R^1=CH_3$)

(a) Ethyl trans-2,4-dimethyl-dec-4-en-8 ynoate. [13a $R^1=CH_3$]

The crude alcohol 3 (see Flow Sheet No. 2), 5.47 g (81% pure, 31.8 mmoles), was dissolved in 33.7 g (190 mmoles) triethylorthopropionate together with 0.25 g propionic acid and slowly heated under dry nitrogen to 120° in a 100 ml three-necked flask equipped with a Dean-Stark trap. As the temperature approached 100°, ethanol began to separate and was removed. The reaction mixture was then heated at 120° for 22 hours. After brief cooling it was poured into 100 ml of water and thoroughly extracted with three 25 ml portions of 1.2 N HCl, once with brine then dried over magnesium sulfate and concentrated yielding 7.98 g of a light yellow liquid. Short path distillation yielded 5.89 g (84%) of a colorless liquid (bp 127°–129°/4.7 mm). Vpc analysis indicated this material to be >98% pure showing only one peak of RT 6.7 mm. $n_D$20.5 1.4593

IR: $\lambda_{max}^{Film}$ 3.35, 3.39, 3.42, 3.49, 5.77(C=O), 6.88, 7.27, 7.42, 7.81, 7.98, 8.51, 8.96, 9.55, 9.75, 11.70.

NMR: $\delta_{CCl_4}^{TMS}$ 1.07 (doublet, 3H, J-6.4cps, $C_2$-Me), 1.27 (triplet, 3H, J=7.2 cps, O-C-Me), 1.61 (singlet, 3H, Me-C=), 1.72 (triplet, 3H, J=1.2 cps, Me-C), 1.80–2.70 (multiplet, 7H), 4.07 (quartet, 2H, J=7.2 cps, O—CH$_2$—C), 5.18 (multiplet, 1H, H—C=).

Anal. Calcd. for $C_{14}H_{22}O_2$: C, 75.62; H, 9.99. Found: C, 75.45; H, 9.96.

(b) trans-2,4-Dimethyl-dec-4-en-8-ynal. [8a $R^1=CH_3$]

A solution of 1.39 ml of 3.59 M sodium bis-(2-methoxyethoxy) aluminum hydride benzene solution (Aldrich-Redal; 5.00 mmoles) in 5.0 ml dry THF was cooled in a jacketed addition funnel to −78°. It was then added dropwise over 30 minutes to a very vigorously stirring solution of 1.11 g (5.00 mmoles) of 13a in 4.0 ml dry THF at −78° under a dry nitrogen atmosphere. After vigorously stirring for five hours at −78°, the cold reaction mixture was rapidly poured into 50 ml of 1.2 N HCl and swirled vigorously. The product was extracted with three 25 ml portions of ether which were combined, dried over magnesium sulfate and concentrated. Short path distillation of the residue yielded 0.61 g (65%) of a colorless liquid (bp 105°–107°/2.4 mm). Vpc analysis indicated this material to be >95% pure aldehyde having RT of 3.6 min with only a trace of ester-alcohol mixture at 6.6 min. Silica gel TLC (4:1 hexane-EtOAc) showed only one component of $R_f$, 0.45.

$^{20.5}$ 1.4722

IR: $\lambda_{max}^{Film}$ 3.36, 3.42, 3.47, 3.48, 3.68, 5.79 (C=O), 6.90, 7.25, 7.54, 9.04, 10.83.

NMR: $\delta_{CCl_4}^{TMS}$ 1.00 (doublet, 3H, J=6.0 cps, $C_2$-Me), 1.61 (singlet, 3H, Me—C=), 1.70 (triplet, J=1.0 cps, 3H, Me-C), 1.70–2.70 (multiplet, 7H), 5.21 (multiplet, 1H, H—C=), 9.68 (doublet, J=1.5 cps, 1H, O=C—H).

Synthesis of Ylides

The following examples will serve to illustrate the synthesis of different species of the ylide III.

(a) The Ylide 24

This ylide is synthesized as set forth in Flow Sheet No. 3. The several steps in this synthesis are described in Examples 2 to 13.

EXAMPLE 2—3-Methyl-4-methylene-cyclohex-2-enone (15)

Step 1 of Flow Sheet No. 3

To 243 g (1.08 mole) of crude ethyl 3-methylcyclohex-3-enone-4 -carboxylic ethylene ketal 14 in 600 ml of dry tetrahydrofuran contained in a 3-liter flask fitted with a mechanical stirred nitrogen inlet, and addition funnel was added slowly (with icebath cooling) over a 3 hour period 400 ml of "Red-Al" solution (Aldrich Chemical Co., 2.78 moles of hydride) in 200 ml of dry tetrahydrofuran. After the addition was complete the reaction mixture was allowed to stir overnight at room temperature. Excess "Red-Al" was destroyed by the addition of 10% aqueous sodium hydroxide and the precipitated aluminum salts were filtered off through celite. To the organic filtrate containing 3-methylcyclohex-3-enone-4-hydroxylmethyl ethyleneketal was added 100 ml of 10% aqueous hydrochloric acid and this mixture stirred (mechanical stirrer) at room temperature under nitrogen for 4 hours. The reaction mixture was poured into a separatory funnel and extracted with ether (3×1000 ml). The ether extracts were washed with saturated sodium bicarbonate solution, saturated sodium chloride solution and then dried over anydrous sodium sulfate. Filtration and concentration in vacuo afforded 116 g (89% yield) of the dienone 15 as a yellow oil. An analytical sample was distilled to afford a faint yellow liquid, bp 96°–98°/15 mm.

Anal. Calcd for $C_8H_{10}O$: C, 78.65; H, 8.25, Found: C, 78.73; H, 8.36.

Vpc on 3% XE-60°/90° show one peak, $R_t$ 4 min. 1R (film) 5.98μ(C═O)

NMR (CDCl$_3$): δ2.08 (3H,S), 2.60 (4H,m), 5.37 (2H,S), and 5.92 (1H,S).

EXAMPLE 3—Methyl-2-carbomethoxy-3-(2-methyl-4-oxo-2-cyclohexene)-propionate (16)

Step 2 of Flow Sheet No. 3

Into a 2-liter round-bottom flask equipped with a nitrogen inlet, magnetic stirrer, and addition funnel was placed 900 ml of methanol and 3.828 g (0.07 mole, Matheson, Coleman, and Bell) of sodium methoxide. After stirring for 15 minutes, 395 g (3 moles) of dimethyl malonate was added and this mixture stirred for 30 minutes. Then was added dropwise 110 g (0.9 mole) of 15 in 100 ml of methanol. The reaction mixture turned green which faded to a dark yellow. After stirring at room temperature for 19 hours (vpc of a aliquot showed no dienone remaining) the solution was poured into 2 liters of water and acidified to pH 1 with 10% aqueous hydrochloric acid. The diester was extracted with two-1000 ml portions of ether and 1000 ml of dichloromethane. The combined organic extracts were washed with saturated sodium chloride solution and dried over anhydrous sodium sulfate. Filtration and evaporation in vacuo afforded 484 g of an orange oil, a mixture of the substituted dimethyl malonate plus excess dimethyl malonate. (96% yield, the mixture should contain 45% by weight of the alkylated material).

EXAMPLE 4—Methyl 3-(2-methyl-4-oxo-2-cyclohexane)propionate (18)

Steps 3 and 4 of Flow Sheet No. 3

Into a 100 ml round-bottom flask equipped with a reflux condenser, magnetic stirrer, oil bath, and nitrogen inlet was placed 20.335 g of a ca. 45/55 mixture of 16 (ca. 9.02 g, 35.5 mmole) and dimethyl malonate (ca. 11.31 g), 25 ml of glacial acetic acid, 25 ml of water, and 5 ml of concentrated hydrochloric acid. This mixture was refluxed for 19 hours, cooled, and extracted with dichloromethane (3×100 ml). The organic extracts were washed with saturated sodium chloride solution and dried over anhydrous sodium sulfate. Filtration and evaporation in vacuo afforded 8.109 g of a brown oil. The crude acid 17 was esterified according to the procedure of Clinton and Laskowski. Into a 100 ml round-bottom flask was placed the crude acid, 30 ml of dichloromethane, 12 ml (0.3 mole) of methanol, and 0.1 g of p-toluenesulfonic acid. The mixture was refluxed for 17 hours, and then the cooled reaction mixture was washed with water, saturated sodium bicarbonate solution, and saturated sodium chloride solution and dried over anhydrous sodium sulfate. Filtration and concentration in vacuo afforded 5.685 g of a brown liquid. Distillation afforded 4.010 g (58% yield) of a light yellow liquid, bp 115°–118° 0.15 mm.

Anal. Calcd. for $C_{11}H_{16}O_3$; C, 67.32; H, 8.22.
Found: C, 67.38%, H, 8.19%.
Vpc 3% XE-60°/172°
4 min. 97%
3 min. 2%
2 min. 1%
IR (film): 6.00μ(C—O), 5.76μ(C═O)
NMR (CDCl$_3$): δ2.00 (3H,S), 3.67 (3H,S), 5.80 (1H,S)

EXAMPLE 5—Methyl 3-(2-methyl-4-oxo-2-cyclohexene)propionate ethylene thioketal (19)

Step 5 of Flow Sheet No. 3

(A) Into a 250 ml round-bottom flask fitted with a magnetic stirrer and drying tube was placed 6.027 g (30.8 mmole) of 18 100 ml of chloroform and 10 ml of ethanedithiol followed by the addition of 2 ml of boron trifluoride etherate. The solution turned yellow and water started to separate. After stirring at room temperature for 5.5 hours the reaction mixture was poured into 200 ml of water followed by 300 ml of ether. The two layers were separated and the organic portion washed with 10% aqueous sodium hydroxide (2×100 ml), saturated sodium chloride solution (1×200 ml), and dried over anhydrous sodium sulfate. Filtration and concentration in vacuo afforded 8.235 g of a yellow orange liquid. Bulb-to-bulb distillation at 180°/0.025 mm afforded 7.949 g (95% yield) of the thioketal 19 as a light yellow liquid.

(B) Into a 2-liter round-bottom flask fitted with a reflux condenser, magnetic stirrer, heating mantle, and nitrogen inlet was placed 463 g of a ca. 45/55 mixture of 16 ca. (208 g, 0.82 mole) and dimethyl malonate ca. (255 g), 500 ml of glacial acetic acid, 500 ml of water, and 100 ml of concentrated hydrochloric acid. The mixture was refluxed for 22 hours, cooled, and poured into 2 liters of water. The acid was extracted with three-1000 ml portions of dichloromethane, the organic extracts washed with saturated sodium chloride solution and concentrated in vacuo to 1000 ml. The crude acid was esterified according to the procedure of Clinton and Laskowski. Into a 2-liter round-bottom flask was placed the dichloromethane solution of the acid, 360 ml of methanol (9 moles), and 3 g of p-toluenesulfonic acid. This mixture was refluxed for 21 hours, and then the cooled reaction mixture was washed with water, saturated sodium bicarbonate solution, and saturated sodium chloride solution. The dichloromethane solution containing the keto-ester was placed into a 2-liter round-bottom flask followed by 200 ml of ethanedithiol. The flask was fitted with a drying tube and magnetic stirrer and 40 ml of boron trifluoride etherate was added. The solution was stirred over night (15 hours) and then poured into a separatory funnel. The organic layer was washed with two-500 ml portions of 10% aqueous sodium hydroxide, saturated sodium chloride solution (1×500 ml), and dried over anhydrous sodium sulfate. Filtration and evaporation in vacuo afforded 197 g of brown liquid Distillation afforded 92.4 g (0.34 mole, 41% yield) of the thioketal-ester 19 as a clear liquid, bp 173°–174°/0.15 mm; 144°/146° 0.02 mm.

Anal. Calcd for $C_{13}H_{20}O_2S_2$; C, 57.34; H, 7.40 S, 23.50.
Found: C, 57.22; H, 7.28; S, 23.57.
Vpc 3% XE-60/190°
4 min. 1%
5.5 min. 99%
IR (film): 5.73μ(C═O),
NMR (CDCl$_3$): δ1.70 (3H,S), 3.33(4H,S), 3.68 (3H,S), 5.68 (1H,S)

EXAMPLE 6—3-(2-methyl-4-oxo-2-cyclohexene)-propionic acid ethylene thioketal (19a) (The dl-acid corresponding to ester 19)

Into a 500 ml round-bottom flask equipped with a magnetic stirrer and nitrogen inlet was placed 56.1 g (0.260 mole) of 18 300 ml of methanol, and 19.7 g (0.30 mole) of 85% potassium hydroxide in 75 ml of water. After stirring at room temperature for 24 hours the mixture was poured into a separatory funnel followed by 400 ml of water. The mixture was extracted with 200 ml of ether and the aqueous solution acidified to pH 1 with 10% aqueous hydrochloric acid. The acid was extracted with three-300 ml portions of dichloromethane. After washing with saturated sodium chloride and drying over anhydrous sodium sulfate filtration and concentration in vacuo afforded 53.7 g (100% yield) of the acid as thick light-brown oil.

Anal. Calcd for $C_{12}H_{18}O_2S_2$; C, 55.81; H, 7.02; S, 24.78. Found: C, 55.90; H, 7.02; S, 24.91.

IR (film): 5.84μ(C=O)
NMR (CDCl$_3$): 1.71 (3H,S), 3.33 (4H,S), 5.63 (1H,S), 11.22 (1H,S)

EXAMPLE 7—Resolution of the Acid 19a into d- and l-salt

To a solution of 53.2 g (0.206 mole) of dl-acid 19a in 900 ml of hot ethyl acetate contained in a 1-liter Erlenmeyer flask was added 25.157 g (0.207 mole) of d-α-methylbenzyl-amine in 100 ml of hot ethyl acetate. The resulting solution was heated to boiling for a few minutes and then allowed to cool. A seed crystal was added and the solution cooled slowly to room temperature. Filtration afforded 31.5 g (0.083 mole, 40%) of light tan needles [α]$_D$ free acid + 10.1°. Another recrystallization from 400 ml of hot ethyl acetate, cooling slowly to room temperature, afforded 24.8 g (0.065 mole) of needles [α]$_D$ of free acid +13.1°. One more recrystallization from 340 ml of hot ethyl acetate gave 20.5 g (0.054 mole, 26%) of white needles, mp 107°-113°, [α]$_D$ of free acid +13.7°.

Anal. Calcd for $C_{20}H_{29}NO_2S_2$: C, 63.31; H, 7.70; N, 3.69; S, 16.87. Found: C, 63.42; H, 7.63; N, 3.73; S, 16.88.

The mother liquor from the first recrystallization was concentrated to 700 ml and cooled to 0°. Cotton-like crystals separated which are the salt from the l-acid. These were not collected but this mixture was treated with 10% aqueous hydrochloric acid to liberate the free acid. To a solution of ca. 32 g (0.123 mole) of l-enriched acid 1-19a in 400 ml of hot ethyl acetate was added 15.30 g (0.126 mole) of l-α-methylbenzylamine in 100 ml of hot ethyl acetate. The resulting solution was heated to boiling for a few minutes and then allowed to cool slowly to room temperature. Filtration afforded 29 g (0.076 mole, 37%) of off-white needles, [α]$_D$ of free acid −8.15°. Another recrystallization from 400 ml of hot ethyl acetate, cooling slowly to room temperature, afforded 20.8 g (0.055 mole) of needles, [α]$_D$ of free acid −12.2°. One more recrystallization from 320 ml of hot ethyl acetate gave 16.2 g (0.043 mole, 21%) of off-white needles, mp 107°-112°, [α]$_D$ of free acid −14.2°.

Anal. Calcd for $C_{20}H_{29}NO_2S_2$: C, 63.31; H, 7.70; H, 3.69; S, 16.87.
Found: C, 63.15; H, 7.53; H, 3.68; S, 17.09.

EXAMPLE 8—d-3-(2-methyl-4-oxo-2-cyclohexene)-propionic acid ethylene thioketal (d-19a)

To 19.762 g (0.052 mole) of salt of d-19 suspended in 300 ml of ethyl acetate was added 200 ml of 10% aqueous hydrochloric acid. This mixture was stirred for 10 minutes and then poured into a separatory funnel and separated. The organic layer was washed with brine and dried over anhydrous sodium sulfate. Filtration and evaporation in vacuo afforded 13.904 g (104% yield) of the acid D-19a as a light tan oil [α]$_D$ + 13.7°.

Bulb-to-bulb distillation, 169°-173°/0.015 mm afforded an analytical sample as a clear oil.

Anal. Calcd for $C_{12}H_{18}O_2S_2$; C, 55.81; H, 7.02; S, 24.78. Found: C, 55.94; H, 7.12; S, 24.89.

EXAMPLE 9—3-(2-methyl-4-oxo-2-cyclohexene)-9-propyl alcohol ethylene thioketal (20)

Step 6 of Flow Sheet No. 3

The thioketal methyl ester 19, 35.74 g (131 mmoles), was dissolved in 300 ml dry THF in an oven-dried 1 liter flask equipped with a magnetic stirring bar, addition funnel and an N$_2$ inlet. The solution was cooled to 0° and 50 ml (340 mmoles H$^-$) of Redal, (sodium bis-(2-methoxyethoxy) aluminum hydride in benzene) diluted with 60 ml dry THF was added from the funnel over 15 minutes. The solution was stirred for four hours at 0°. After this time the reaction mixture was carefully quenched with 5% aqueous sodium hydroxide by dropwise addition until a granular precipitate was obtained. The almost clear supernatant was decanted and the aluminum salts were washed with ether. The organic solvent was evaporated in vacuo and the residue was taken up in ether. The ether solution was extracted with water (2×550 ml) and the aqueous layers were extracted with ether (2×200 ml). The combined ether layers were washed with saturated brine and then dried over anhydrous potassium carbonate. Evaporation of the solvent in vacuo left 32.2 g pale yellow oil (131 mmoles, quantitative recovery) of the thioketal alcohol (20). A sample was purified by the silica gel (ethyl acetate) R$_f$ 0.48, and distillation bp 180°/0.050 mm.

Analysis: Calc'd for: $C_{12}H_{20}OS_2$: C,59.00; H,8.25; S,26.25. Found: dl—C,59.15; H,8.16; S,26.20. d—C,58.76; H,8.05; S,26.54. l—C,58.89; H,8.39.

| NMR (CDCl$_3$) | 1.66 δ | (s, 3H, CH$_3$(R)C=) |
|---|---|---|
| | 3.31 | (s, 4H,—S—CH$_2$CH$_2$—S—) |
| | 3.64 | (m, 2H, —CH$_2$—OH) |
| | 5.60 | (s, 1H, H(R)C=) |
| IR (liquid film) | 2.97μ (OH) | 3.41 (CH) |
| | 6.08 | $\diagup C=C \diagdown$ 7.85, 9.50, 11.80 |

[α]$_D^{22°}$ + 24.3° (CHCl$_3$)
tlc: Et$_2$O/hexane (1/1) R$_f$ 0.15

EXAMPLE 10—3-(2-methyl-4-oxo-2-cyclohexene)-propanol tosylate ethylene thioketal (21)

Step 7 of Flow Sheet No. 3

In an oven-dried 250 ml flask was placed p-toluenesulfonyl chloride (recrystallized from hexane/chloroform; 36 g 0.188 mole, 1.42 equivalents) and 50 ml dry pyridine. The mixture was stirred and cooled in an ice water bath. Then the above crude thioketal alcohol 20 was dissolved in 30 ml dry pyridine and added slowly to the chilled tosyl chloride/pyridine mixture. Transfer of the alcohol was completed with two pyridine washings (15 ml then 5 ml). Soon after the alcohol solution had been added the mixture became a very pale yellow, clear solution but within five minutes a fine white precipitate of pyridinium hydrochloride began to come out of solution. After stirring two hours at 0° 8 ml of 85% lactic acid (75 mmoles) was added dropwise via syringe. After stirring an additional 30 minutes at 0° the reaction mixture was poured into 1 liter of 10% HCl overlaid with ether (500 ml). The ether layer was extracted with another liter of 10% HCl. The combined aqueous layers were then extracted with ether (2×200 ml). The ether layers were washed successively with $H_2O$, saturated $NaHCO_3$ and saturated brine. After drying over anhydrous potassium carbonate the solvent was evaporated in vacuo leaving the thioketal tosylate (21) a very pale yellow viscous oil, 48.6 g (126.5 mmoles, 96% yield). This product was used directly in the next step. A sample of the tosylate (21) was purified by chromatography on Florisil with 10% ether in hexane.

Analysis: Calc'd for $C_{19}H_{26}S_3O_3$: C, 57,25; H, 6.57. Found: C, 57.17; H, 6.54.

Spectral Data:
NMR: (CDCl₃)  1.61 (s, 3H, CH₃(R) C=)
2.45 (s, 3H, CH₃—Ar)
3.31 (s, 4H, —S—CH₂CH₂—S—)
4.06 (t, 2H, J = 6Hz, —CH₂—OTs)
5.62 (s, 1H, H(R)C=)
7.39;7.86 (d, 2H each, J = 8Hz, H's on aromatic ring)

IR: (CHCl₃ sol'N) 3.41 (CH)
7.36, 8.40, 8.51 (tosylate bands)

$[\alpha]_D^{22°} + 18.5°$ (CHCl₃)

$[\alpha]_D^{22.5°} -18.6°$ (CHCl₃)

tlc: Et₂O/hexane (2/1) R_f 0.54

EXAMPLE 11—1-iodo-3-(2-methyl-4-oxo-2-cyclohexene)-propane ethylene thioketal (22)

Step 8 of Flow Sheet No. 3

Excess sodium iodide was added to 180 ml acetone and stirred at 23° for 30 minutes before the flask was set aside and allowed to settle and cool to room temperature. This sodium iodide saturated acetone was added to the above crude thioketal tosylate (21) and stirred at 23°. Then 0.5 ml of diisopropylethyl amine was added to the stirred suspension to prevent isomerization of the olefinic bond. After 2½ hours half of the acetone was evaporated in vacuo before the reaction mixture was poured into 1 liter of water overlaid with 500 ml ether. The aqueous layer was extracted with ether (2×200 ml). The combined ether layers were washed with saturated sodium bicarbonate and saturated brine. After drying over anhydrous potassium carbonate the solvent was evaporated in vacuo to yield the thioketal iodide (221), a pale yellow viscous oil, 41.9 g. The crude iodide was applied to 250 g of 100–200 mesh Florisil and eluted with 5% ether in hexane; 39.45 (0.112 moles, 89% yield) of clear colorless oil was collected. This represented an overall conversion of 85.5% from the thioketal ester (19).

Analysis: Calc'd for $C_{12}H_{19}I$: C,40,69; H,5.41; I,35; Found: C,41.18; H,5.39; I,35.

Spectral Data:
NMR: (CDCl₃)  1.69 δ  (s, 3H, CH₃(R)C=)
3.19 (t, 2H, J = 6Hz, —CH₂—I)
3.32 (s, 4H, —S—CH₂CH₂—S—)
5.61 (s, 1H, H(R)C=)

IR: (liquid film) 3.41 (CH)

6.09 $\left( \begin{array}{c} \diagdown \\ \diagup \end{array} C=C \begin{array}{c} \diagup \\ \diagdown \end{array} \right)$ 7.89, 8.19, 8.60, 11.80 tlc: Et₂O/hexane (2/1) R_f 0.70

$[\alpha]_D^{22} + 24.1$

EXAMPLE 12—3-(2-methyl-4-oxo-2-cyclohexene)-propane-1-tri-phenylphosphonium iodide ethylene thioketal (23)

Step 9 of Flow Sheet No. 3

In a 100 ml flask were placed 12.3 g (34.8 mmole) of the thioketal iodide (22), 12.8 g triphenylphosphine (1.4 equivalents and 15 ml dry acetonitrile (distilled from CaH₂). All three components were necessary to effect complete solution at 50°. Huenig's base (diisopropylethylamine 1.0 ml) was added and the reaction vessel was flushed with dry N₂ and then placed in a 50° oil bath. After 18 hours the homogenous reaction mixture was diluted with 35 ml dry methylene chloride then poured into swirling hexane (250 ml). A yellow-white gummy product separated from the hexane solution. After a little swirling the supernatant was decanted and the gummy product washed with hexane (2×30 ml). The hexane washings made the product gummier and far less mobile. Excess solvents were removed by aspirator. The crude product swelled to give a solid foam (volume about 600 ml) which when dry was broken down to a powder with a spatula. After the bulk of the volatiles were removed by aspirator the product was dried in vacuo then placed in a drying pistol at 68° (hexane)/0.010 mm to yield an ivory white powder 20.5 g (33.3 mmoles, 96% yield).

Analysis: Calc'd for: $C_{30}H_{35}IPS_2$: C,58.44; H, 5.56; I, 20.58. Found: l—C, 58.38; H, 5.62; I, 20.52; dl—C,58.47; H, 5.69; I, 20.16; d—C,58.34; H, 5.66; I, 20.65.

Spectral Data:
NMR: (CDCl₃)  1.61 (s, 3H, CH₃(R)C=)
3.29 (s, 4H, —S—CH₂CH₂—S—)
5.51 (s, 1H, H(R)C=)
7.70 (m, 15H, —Pφ₃)

IR: (CHCl₃ sol'n) 3.40 (CH)
6.31 (aromatic CH)
8.32, 9.02, 14.05 (all strong)

mp: dl 87°–91.5°
l 91°–93.5°
d 88°–90°

$[\alpha]_D^{22.5} - 4.79°$ (CHCl₃)

$[\alpha]_D^{22} + 5.08°$ (CHCl₃)

EXAMPLE 13—Preparation of Solution of Ylide 24

Step 10 of Flow Sheet No. 3

In an oven-dried 250 ml flask equipped with a magnetic stirring bar was placed 15.92 g (25.9 mmoles) of the phosphonium salt (23). After flushing the flask with dry nitrogen, 50 ml of dry THF were added. The partially dissolved salt was stirred at 23° as phenyllithium in THF was added via syringe until a permanent yellow was obtained (indicating a small concentration of the phosphorous ylide (24).

The phenyllithium was prepared by the procedure of Gilman (H. Gilman, R. G. Jones, Organic Reactions VI, p. 352). When the dark filtered solution of the phenyllithium in ether was placed in a freezer at −17°, the phenyllithium was observed to crystallize in large white crystals. The supernatant ether was decanted and dry THF was added. The concentration of phenyllithium was determined by the method of Watson and Eastham (J. Organomet. Chem. 9, 165(1967), which uses 1,10-phenanthroline (Aldrich) as a carbon base indicator. Solutions of phenyllithium in THF when stored at freezer temperatures (−15° to −20°) are stable and hold their titer within 5% for two months or longer.

After the permanent yellow color was obtained 1.00 equivalent of phenyllithium in THF (1.69 M, 15.3 ml, 25.9 mmoles) was added causing the temperature of the mixture to rise. Complete dissolution to a clear cherry red solution occurred within a minute.

(b) The Ylide 25

The ylide 25 and a method of synthesizing it are shown in Flow Sheet No. 4. The preparation is described in general terms in Example 14 and in detail in Examples 39 to 41.

EXAMPLE 14

2-methylfuran 26 is alkylated with 1,4-dibromobutane in the presence of a strong base, for example, n-butyllithium under anhydrous conditions, to produce 5-(4-bromobutyl)-2-methylfuran 27. The latter is then treated with ethylene or propylene glycol in the presence of an acid catalyst to afford the diketal bromide 28 (n=2 or 3). The bromide 28 is converted with a source of iodine ion, for example, sodium iodide, to the corresponding diketal iodide 29, which in turn is caused to react with triphenylphosphine to give the diketal phosphonium iodide 30. Treatment of the latter with phenyllithium in ether splits out the elements of HI resulting in a red solution of the ylide 25 which is not isolated as such but is used directly in condensation with aldehyde 8 (or 8a or 8b).

Synthesis of Cyclization Substrates (a) Condensation of Ylide 24 with Aldehyde 8 and Conversion of Resulting Cyclization Substrate to Other Cyclization Substrates.

The thioketal ylide 24 and the aldehyde 8 (R$^1$=CH$_3$) may be condensed as follows to afford the thioketal cyclization substrate 31 and the latter may, if desired have the thioketal group converted to a keto group as in 32 and the latter reduced to an hydroxyl group to afford a cyclization substrate 33 as shown in Flow Sheet No. 5.

Example 15 illustrates the condensation of the ylide 24 and aldehyde 8a(R$^1$=CH$_3$) to afford the thioketal cyclization substrate 31. Examples 16 and 17 illustrate different methods of hydrolyzing the thioketal 31 to the ketone 32. Example 18 illustrates the reduction of the ketone 32 to the hydroxy cyclization substrate 33.

EXAMPLE 15—Synthesis of Cyclization Substrate 31

The solution of the ylide 24 prepared as in Example 13 was cooled to −70° in a dry ice-acetone bath. After stirring 15 minutes at −70°, the aldehyde 8a(R$^1$=CH$_3$) (4.25 g, 25.9 mmole) in 5 ml dry THF was added dropwise via syringe. The color of the solution lightened to a pale orange as the solution was stirred for 15 minutes. Then 20 ml of phenyllithium in THF (1.3 equivalents) was added via syringe generating a very dark red solution of the betaine ylide. Sufficient dry ether (90 ml) was then added to adjust the THF/ether ratio to 1/1. The temperature was allowed to rise to −30°. After stirring 10-15 minutes at −30° the ylide was quenched with methanol to give a pale tan mixture which was allowed to warm to 23° and stand overnight.

The reaction mixture was added to 500 ml hexane and after stirring a few minutes the precipitated triphenylphosphine oxide was allowed to settle and the slightly cloudy supernatant decanted. The precipitated oxide was washed with 100 ml hexane. The solvent was evaporated in vacuo leaving a yellow oil. The crude product was applied to a 100 g column of Florisil (100-200 mesh) and eluted with hexane (to remove most of the biphenyl) followed by 5% ether in hexane. A total of 6.917 g of thioketal 31 was collected (18.5 mmoles, 71.5% yield). Vpc analysis shows less than 2% of the β;γ-unsaturated isomer and about 1% cis olefin. A sample was purified by the silica gel (benzene) R$_f$0.55 and distillation bp 180/25μ.

Analysis: Calc'd for: C$_{23}$H$_{34}$S$_2$: C, 73.74; H, 9.15. Found: dl—C, 74.12; H, 9.23. l—C, 73.98; H, 9.07. d—C, 73.88; H, 8.95.

| Spectral Data: | |
|---|---|
| NMR: CDCL$_3$) | 1.60 (s, 3H, vinyl CH$_3$) |
| | 1.66 (s, 3H, vinyl CH$_3$ in ring) |
| | 1.76 (s, 3H, —≡—CH$_3$) |
| | 3.31 (s, 4H, thioketal) |
| | 5.20 (m, 1H, ) |
| | 5.41 (m, 2H ) |
| | 5.60 (s, 1H, vinyl H in ring) |
| IR: (CHCL$_3$ sol'n) 3.32μ, 3.41, 3.49 (CH) | |
| | 6.07 ( >=< ) |
| | 7.25 (w), 7.82 (w) |
| | 10.32 (m, trans ⌇) |
| Mass spectrum (Atlas) | M$^+$ 374 |
| | M − 28 (thioketal cleavage) |
| tlc: Ether/hexane (1/1) | R$_f$0.65 |
| benzene | R$_f$0.57 |
| [α]$_D^{22}$ = −19.7° | |
| [α]$_D^{22}$ = +21.0° | |

For cyclization of 31 to occur to afford a steroid, it is necessary that both olefinic groups of the dienyne segment be trans groups. The trans group of the aldehyde 8 is assured by its method of synthesis. The trans character of the olefinic group which forms the C-8 and C-9 portions of the steroid is assured by its method of synthesis above described which includes steps which will be recognized as the Schlosser modification of the Wittig synthesis; see Schlosser, Angewandte Chemie, International Edition, 5, p. 126 (1966).

EXAMPLE 16—7-Methyl-13-(2-methyl-4-oxo-2-cyclohexene)-tridecatrans, trans-6,10-dien-2-yne (32)

In a 250 ml flask equipped with magnetic stirrer were placed 4.749 g of the thioketal 31 (12.7 mmole), 160 ml acetonitrile, 32 ml $H_2O$ and 18 ml methyl iodide. This solution was stirred under an atmosphere of dry nitrogen at 45° for 11 hours. When an aliquot was removed and analyzed by vpc, the hydrolysis was found to be complete. The reaction mixture was poured into 350 ml ether and washed with dilute $Na_2S_2O_3$ (2×400 ml). After extraction of the aqueous layers with ether the usual work-up was followed. This left a yellow oil which was chromatographed on 100 g, 100–200 mesh Florisil. The column was eluted with hexane followed by hexane containing 10% ether then 20% ether. A total of 3.249 g of the $\alpha,\beta$-unsaturated ketone 32 was obtained (10.9 mmoles, 86% yield). An analytical sample was prepared by treatment with Raney nickel in ethyl acetate/ethanol for ½ hour followed by evaporative distillation at 160°/25

Analysis: Calc'd for: $C_{21}H_{30}O$: C, 84.51; H, 10.13. Found: dl—C, 84.61; H, 10.34.

Spectral Data:
NMR: (CDCl₃)  1.58 δ  (s, 3H, vinyl $CH_3$)
1.73  (s, 3H, C C—$CH_3$)
1.93  (s, 3H, vinyl $CH_3$ of ketone)
5.18  (m, 1H, )
5.41  (m, 2H, )
5.80  (s, 1H, vinyl H of ketone)
IR: (CHCl₃ sol'n)  3.32μ, 3.41, 3.49 (CH)
6.02  7.24, 7.99
10.32
(trans  ) 11.65
UV: $\lambda_{max}^{MeOH}$ 238Mμ (E = 15,300)
$[\alpha]_D^{22} = +58.4°$
$[\alpha]_D^{22} = -58.0°$

EXAMPLE 17—Modified Hydrolysis of Thioketal 31

The method of Example 16 causes enolization of the ketone 32, therefore racemizes the thioketal 31 if that compound is used in resolved, optically active form. The procedure of this present example avoids or respresses enolization and results in an optically active ketone 32.

Into a 10 ml round-bottom flask was placed 58 mg (0.1555 mmole) of 1-thioketal 31 from acid with $[\alpha]_D - 10.1°$), 5 ml of dimethylformamide, 350 μl (800 mg, 5.6 mmole) of methyl iodide, 1 ml of water, and 26 mg (0.26 mmole) of calcium carbonate. This mixture was stirred at room temperature for 42 hours. Vpc of an aliquot on 3% XE-60/225° showed ketone 32 (76%, $R_t$ 5 min), 6% of unreactd thioketal ($R_t$ 13 min), and 19% of an unknown compound at $R_t$ 17 min. The reaction mixture was poured into a separatory funnel followed by ether. The mixture was washed with brine (pH of aqueous portion is 3–4) and dried over anhydrous sodium sulfate. Filtration and evaporation in vacuo afforded 52 mg of a yellow oil. This material was adsorbed onto a silica gel plate (10 cm×20 cm×0.1 cm) and eluted with ethyl acetate: benzene (1:4) to afford 24 mg (52% yield) of the ketone 32 as a clear oil, $[\alpha]_D - 41.0°$.

EXAMPLE 18—7-Methyl-13-(2-methyl-4-hydroxy-2-cyclohexen trideca-trans, trans-6,10-dien-2-yne (33)

In an oven dried 100 ml flask equipped with a magnetic stirrer bar were placed 2.158 g (7.24 mmoles) of the unsaturated ketone (32) and 25 ml dry THF. This solution was stirred under dry nitrogen and cooled to 0°. A solution of 0.8 ml Redal in 5 ml dry THF (1.5 equivalents of $H^-$) was added slowly via syringe to the chilled solution of ketone (32). The nearly colorless solution was stirred for 1 hour at 0°. After this time the excess Redal was carefully destroyed with 5% aqueous sodium hydroxide until a granular precipitate was formed. The almost clear supernatant was decanted and the salts washed with ether. The usual workup yielded the allylic alcohol (33), a very pale yellow oil, 2.128 g (99% yield). There was no unreacted ketone by infrared spectroscopy. A sample of the crude product was purified by chromatography on #5 basic alumina (Woelm) with 20% ether in hexane as eluent. The last traces of solvent were removed at 23°/10μ.

Analysis: Calc'd for: $C_{21}H_{32}O$: C, 83.94; H, 10.73. Found: dl—C, 84.00; H, 10.46.

Spectral data:
NMR: (CDCl₃)  1.60 δ  (s, 3H, vinyl $CH_3$)
1.67  (s, 3H, vinyl $CH_3$ in ring)
1.76  (s, 3H, C≡C—$CH_3$)
5.18  (m, 1H,)
5.42  (m, 3H, other vinyl H's)
IR: (liq. film)  3.00μ (OH); 3.41, 3.49 (CH);
6.04 (C=C), 7.26, 9.65, 10.32

(b) Condensation of Ylide 25 with Aldehyde 8 to provide Cyclization Substrate 34

This synthesis is illustrated in Flow Sheet No. 6. The condensation is described in Example 19 and in more detail in Examples 42 to 46.

EXAMPLE 19—Synthesis of Cyclization Substrate 34

The unsaturated aldehyde 8 and ylide 25 are condensed in the presence of phenyllithium to give the diketal dienyne 35 [$R^1$ is $CH_3$ or Si(lower-alkyl)₃]. If the compound 35 where $R^1$ is Si(lower-alkyl)₃ is treated with silver ion or aqueous potassium hydroxide in methanol or THF, the tri-lower-alkyl-silyl group is removed to give compound 35 where $R^1$ is H. The latter, either in the form of a Grignard reagent or alkali metal derivative ($R^1$ is MgX, Na, Li, etc.) can be condensed with formaldehyde to give compound 35 where $R^1$ is $CH_2OH$.

The diketal compound 35 ($R^1$ is $CH_3$ or $CH_2OH$) is then subjected to acid hydrolysis to give the dienyne diketone 36 ($R''$ is H or OH). The latter undergoes an kitol condensation under alkaline conditions to give the cyclopentenone derivative 36A.

The cyclopentenone 36A when treated with methyllithium or with methylmagnesium halide and the resulting reaction mixture hydrolyzed gives the cyclopentenol derivative 34 where R° is CH$_3$ and R" is H or OH. Alternatively, the cyclopentenone 36A can be reduced with a metal hydride capable of reducing the oxo group without reducing the unsaturated linkages, for example, sodium borohydride or lithium aluminum hydride, or with an aluminum (lower-alkoxide)$_3$ (Meerwein-Ponndorf-Verley reduction), to the secondary alcohol 34 where R° is H and R" is H or OH. The cyclopentenol 34 provides a cyclization substrate for producing an A-nor steroid as described in Example 24 below.

Synthesis of Steroids by Cyclization of Cyclization Substrates 31, 33 and 34

Flow Sheet No. 7 illustrates the cyclization of the thioketal cyclization substrate 31 to mixtures which include steroid products. Flow Sheet No. 8 illustrates the cyclization of the cyclization substrate 33 to different steroids. Flow Sheet No. 9 illustrates the cyclization of the cyclization substrate 34 to an A-nor steroid. Examples 20 to 24 provide details of the steps illustrared in these flow sheets.

EXAMPLE 20—Cyclization of Thioketal 31 with Stannic Chloride

Into a 50 ml round-bottom flask fitted with a rubber serum cap and a magnetic stirrer was placed 247 mg (0.66 mmole) of thioketal 31 (optically active, from acid 19a with $[\alpha]_D^{21°}$ −10.1°) and 20 ml of dry dichloromethane. This mixture was cooled to 0° with an ice bath and 0.5 ml (4.37 mmole, 6.6 eq) of stannic chloride was injected slowly. The first drop of acid turned the solution yellow which turned orange with additional acid. This orange solution was stirred for 15 minutes at 0° and then poured into aqueous 10% hydrochloric acid and extracted with ether. The ether extracts were washed with saturated sodium bicarbonate solution, brine and dried over anhydrous sodium sulfate. Concentration in vacuo afforded 243 mg (90% yield) of a vinyl sulfide mixture of the chlorocarbons 37 and 38 and a white semi-solid.

The nmr spectrum showed singlets at δ0.87, 0.92, and 1.03 and a vinyl proton at δ5.6.

EXAMPLE 21—Cyclization of Thioketal 31 with Titanium Tetrachloride

Into a 50 ml round-bottom flask fitted with a magnetic stirrer and nitrogen inlet was placed 278 mg (0.744 mmole) of thioketal 31 and 20 ml of dry 1,2-dichloroethane. Cooled to −30° in an acetone/dry ice bath and 0.05 ml (4.5 mmole, 6 eq) of titanium tetrachloride was injected slowly. The first drop turned the solution orange which turned red and then deep purple with additional acid. This dark purple solution was stirred for 10 minutes at −30° to −25° and then poured into 75 ml of 10% aqueous hydrochloric acid and extracted with ether. The ether extracts were washed with saturated sodium bicarbonate solution, brine and dried over anhydrous sodium sulfate. Filtration and concentration in vacuo afforded 295 mg of a light yellow oil. This material was absorbed onto a silica gel plate (20 cm × 20 cm × 0.1 cm) and eluted with ethyl acetate; hexane (1:4) to afford 242 mg (79% yield) of a clear oil which solidified on standing. Vpc on 3% XE-60/240° showed 4 peaks; 70% of compound (39) (R$_t$=12.25 min), 12% of compound (40) (R$_t$=14.25 min) and two other components of unknown structures, 15% (R$_t$=8.5 min) and 3% (R$_t$ 10.75 min). Recrystallization from hexane afforded white needles, mp 155°–158°, vpc of this material showed only the peaks corresponding to (39) and (40) in the same ratio as above.

NMR (CDCl$_3$): δ0.83 (S), δ0.89 (S); δ2.14, and 3.19 (S) Mass Spec. (Atlas): M+ 410

EXAMPLE 22—Cyclization of Allylic Alcohol 33 to Δ'-pregnen-20-one (41)

In an oven-dried 500 ml 3-necked flask equipped with a serum cap, a stopcock adapter, magnetic stirrer bar and a dry ice/acetone condenser was placed 2.50 g (8.33 mmoles) of the allylic alcohol (33). Then 250 ml of 1,1-difluoroethane (Matheson Gas, Genetron 152 A, bp. −25°) was introduced via the stopcock adapter. The allylic alcohol (33) is virtually insoluble in the difluoroethane. Then 30 g of ethylene carbonate (12% by weight; recrystallized from the melt) was added. About 80% of the ethylene carbonate and most of the substrate dissolved. Then 20 ml of trifluoroacetic acid (8% by volume) was introduced dropwise via syringe to the stirred, refluxing (−25°) mixture. A pinkish color began to develop after 25% of the acid had been added. After 15 minutes the solution had become light tan in color and completely homogeneous. The reaction was quenched after 1½ hours by the slow addition of 10% K$_2$CO$_3$ in 50% aqueous methanol. Once quenched the reaction mixture was diluted carefully with 100 ml ether followed by another 100 ml of the 10% K$_2$CO$_3$ solution. The difluoroethane was allowed to boil away and the reaction was stirred overnight. The reaction was poured into water (200 ml) extracted with ether (3×100 ml) and finally worked up as usual. Evaporation of the solvent in vacuo left 2.614 g of crude Δ'-pregnen-20-one (41) as a pale yellow oil (α/β ratio at C-17 85/15). The crude material was applied to 50 g of 100–200 mesh Florisil. Elution with 250 ml of hexane afforded 232 mg of non-polar materials. The desired tetracyclic ketone (41) was eluted with 1.5%, then 3% and 4% ether in hexane. A total of 1.620 g of ketone (41) was recovered for a yield of 65%. One of the fractions was recrystallized from 25% ethyl acetate in methanol to give white plates mp 101°–103° that rearranged into needles mp 113°–114.5°. Further recrystallization give white plates mp 102.5°–103.5°. From another cyclization white needles mp 114.5°–117.5° were obtained. When these crystals were dried at 68°/20μ a small amount was observed to sublime and collect on a cold part of the apparatus, mp 119–120. However when the bulk was sublimed at 125°/25μ two forms were observed; mp 101.5°–102.5° and 111°–112°. All recrystallized samples are pure β-isomer at C-17.

Analysis: Calc'd for: C$_{21}$H$_{32}$O: C, 83.94; H, 10.73. Found: dl—C, 84.05; H, 10.99; d—C, 83.96; H, 10.81.

Spectral Data:
NMR: (CDCl$_3$)  0.62δ  (s, 3H, (C-18)
                1.00   (s, 3H, C-19)

2.08   (s, 3H, C-21 —C(=O)—CH$_3$)
                5.50   (s, 2H, C-1,2)
IR: (KBr)       3.31μ  3.35, 3.40, 3.47 (CH)
                5.85   7.21, 7.40 (m)
                8.30,  8.47, 8.68 (all weak)
                14.1 (m)

-continued

| Mass Spec. (Atlas) | M+ 300 |
| --- | --- |
| | M— 15 (—CH$_3$) |
| | M— 43 (—C(O)CH$_3$) |
| | M— 85 (D ring cleavage) |
| | M— 56 (—C$_4$H$_8$ from A ring) |
| $[\alpha]_D^{22} = +172°$ | |

EXAMPLE 22a—An Alternative Method of Cyclizing Allylic Alcohol 33 to Δ$^1$-pregnen-20-one (41)

An oven-dried 10 ml flask equipped with serum cap and magnetic stirring bar, was charged with 0.0253 g (0.0842 mmole) of the allylic alcohol (33). then 2.5 ml of 2,2,2-trifluoroethanol was introduced by syringe, and resulting solution alternately degassed and purged with N$_2$ three times. After cooling the solution to 0° C., 0.20 ml of trifluoroacetic acid was introduced dropwise via syringe to the vigorously stirred solution. The reaction mixture was maintained at 0° C. for 2 hours. The reaction was then quenched with 6.0 ml of saturated aqueous NaHCO$_3$. The reaction mixture was poured into water and extracted with ether. The extract was washed with brine and dried over MgSO$_4$ to give, after evaporation of ether in vacuo, 0.0276 g of a pale yellow oil. The crude material was purified by preparative thin layer chromatography (silica gel HF$_{254}$ —20% EtOAc or hexane) to give ketone 41, identical in all respects with material obtained in the preceding example.

The following example illustrates an alternative method of cyclizing the allylic alcohol 33 to afford a mixture of isomers 43 and 44. (See Flow Sheet No. 8)

EXAMPLE 23—Δ$^{1,17}$-20-chloro-pregnediene (43) and Δ$'^{17,17a}$-17-chloro-D-homopregnediene (44)

In a 50 ml flask equipped with a magnetic stirrer bar were placed 0.150 g (0.50 mmoles) of the allylic alcohol (33) and 15 ml dry methylene chloride. This solution was chilled to —30° in a dry ice/acetone bath. The reaction mixture was stirred as 0.175 ml stannic chloride (3.0 equivalents) were added dropwise via syringe. A strong orange color developed after 1 equivalent of stannic chloride had been added. The cloudy orange solution was stirred at —20° to —30° for 75 minutes before 7 ml of dry ether was added followed by a slight excess of pyridine. The resulting precipitate was centrifuged and the white precipitates washed with methylene chloride. The supernatant was washed with methylene chloride. The supernatant was washed with 1N HCl then worked up in the usual fashion. Solvent evaporation in vacuo left 0.127 g of cloudy yellow oil. The crude material was chromatographed on 8 g of Florisil with hexane elution. 0.112 g of a clear colorless oil as recovered for a 70% yield. Vpc analysis (3% OV.17, 205°) showed a single peak (RT 10 min, 11.4%) and a doublet (RT 16 and 18 min, 88.6% Ratio (62/38). The above oil was recrystallized from hot absolute ethanol affording fine plates mp 100-106. Vpc analysis of these crystals showed only the doublet of peak in the ratio 61/39.

In another experiment 361 mg of the allylic alcohol (33) was cyclized in 36 ml of 1,1-dichloroethylene (freshly distilled) at —30° to —40° and the temperature was maintained in that range for 50 minutes after 0.35 ml stannic chloride (2.5 equivalents) had been added. This reaction was quenched with pyridine and worked up as previously described. Chromatography on Florisil with hexane yielded 246 mg of a clear colorless oil (64.5% yield). Vpc analysis showed the same single peak (16.4%) and the same doublet; however the ratio of these two peaks was 85/15. Two recrystallizations from absolute ethanol yielded 92 mg of white plates mp 106°-109° (Ratio 88/12). It was subsequently shown that the doublet peaks are the tetracyclic chlorocarbons (43 and 44), the one with the shorter vpc retention time having a 5-membered D ring (43).

Analysis: Calc'd for: C$_{21}$H$_{32}$Cl: C, 79.09; H, 9.80; Found: C, 79.24 H, 9.56.

| Spectral Data: | | |
| --- | --- | --- |
| NMR: (CDCl$_3$) | 0.87δ | (s, 3H, C-18 in) |
| | 0.93 | (s, 3H, C-18 in) |
| | 1.00 | (s, 3H, C-19) |
| | 1.72 | (t, 3H, J = 1.5 Hz, C-21) |
| | 2.13 | (m, 2H, C-16 H's) |
| | 5.52 | (s, 2H, C-1,2) |
| IR: (CHCl$_3$ sol'n) | 3.41μ 3.49 (CH) | |
| | 6.00 (C=C) | |
| | 9.18, 9.97, 10.43, 11.97 | |
| tlc: 20% ethyl acetate/hexane | R$_f$ 0.63 | |

EXAMPLE 24—Cyclization of Pentenol 34 to the A-nor Steroid 42

Cyclization of the cyclopentenol 34 is effected by treating it at room temperature or below with an acid and a substance H-W where W is a nucleophilic radical, for example, acyloxy. The acid cyclizing agent can be any protonic acid having a dissociation constant of at least about 2 × 10$^{-4}$, and includes such acids as formic acid, trifluoroacetic acid, fluorosulfonic acid, trifluoromethanesulfonic acid, picric acid, benzenesulfonic acid, and the like; or a Lewis acid such as stannic chloride, boron trifluoride, aluminum chloride, zinc chloride, and the like. In the event the acid cyclizing agent is a protonic acid, it may also serve as the substance H-W where W is the anion derived from said protonic acid. A preferred class of such anions are formyloxy and halogenated lower-alkanoyloxy having from one to four carbon atoms, at least one halogen atom being in the α-position, including, for example, chloroacetoxy, dichloroacetoxy, bromoacetoxy, trifluoroacetoxy, α-chloropropionoxy, and α,β-dibromopropionoxy. The halogenated lower-alkanoyloxy groups can have from one to three halogen atoms, at least one halogen atom being in the α-position.

It is also possible to effect cyclization of the cyclopentenol 34 with a strong acid (trifluoroacetic acid, stannic chloride, etc.) and an aprotic nucleophile, e.g., ethylene carbonate

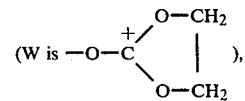

benzene (W is C$_6$H$_5$) or sodium iodide (W=I) or with water as the nucleophile (W is OH).

In the event R" in compound 34 is hydroxy, the latter may be esterified during cyclization with a protonic acid to introduce the corresponding acyl moiety.

Treatment of Steroidal Products of Cyclization to Product Other Steroids

In the cyclization reactions illustrated in Flow Sheets 7 to 9 above and in Examples 20 to 24 above, a variety of steroidal products are provided including normal steroids (six-membered A, B and C rings plus a five-membered D ring), A-nor steroids, and mixtures of normal and D-homo steroids. These steroidal products may be converted to other steroids in various ways. For example, the mixtures of 37/38 and 39/40 produced as in Examples 20 and 21, respectively, may be degraded to produce 5β-androstan-17-one (45) as described in Examples 25 and 26 and illustrated in Flow Sheet No. 9A. The A-nor steroid 42 produced as in Example 24 may be converted to steroids 46 and 47 as illustrated in Flow Sheet 10 or to steroid 48 as illustrated in Flow Sheet 11; see also Examples 47 to 53. Many other transformation techniques, some of which are illustrated in Examples 27 to 30 and which are well known in steroid chemistry, may be carried out to provide desired end products.

Typical of such conversion techniques are reduction of an olefinic group such as a $\Delta^1$-olefinic group by catalytic hydrogenation; oxidation of a C-20 hydroxyl group to a keto group by N-bromosuccinimide; and protection of a sensitive alcohol group by forming an ester. In some cases an ester is more easily crystallized. Further examples are oxidation of the C-3 position of a $\Delta^1$ steroid to a keto group with tert-butylchromate and the introduction of a $\Delta^4$-olefinic group into the A-ring of a steroid by bromination-dehydrobromination.

EXAMPLE 25—Degradation of Vinyl Sulfides (37) and (38) into 5β-androstan-17-one (45) (See Flow Sheet No. 9A)

(a) Treatment of 37/38 with Raney nickel. Into a 25 ml round-bottom flask was placed 190 mg (0.464 mmole if pure) of the above vinyl sulfide mixture 37/38, 10 ml of ethyl acetate, 5 ml of acetone and 1.139 g of wet (water) Raney nickel. The mixture was stirred at room temperature for 45 minutes and then refluxed for 30 minutes, cooled and filtered to afford a clear oil which by nmr still contained vinyl sulfide. This oil was retreated under the above conditions except that the mixture was refluxed for 2 hours, cooled, filtered to remove Raney nickel, the nickel washed several times with ethyl acetate. The organic washings were washed with brine and dried over anhydrous sodium sulfate. Filtration and evaporation in vacuo afforded 141 mg (92% yield) of the olefins 43/44. The vpc on 3% XE-60/188° showed four small peaks with $R_t<4$ minutes and 55% 43 ($R_t=7$ minutes), 32% 44 ($R_t=8$ minutes), and two other components of unknown structures, 12% ($R_t=4.5$ minutes) and 2% ($R_t=6.25$ minutes). This material coinjected with chloro olefin prepared as in Example 23.

(b) Hydrogenation. The above olefins 43/44 (136 mg) were hydrogenated over ca. 50 mg of 10% Pd/C in 10 ml of ethyl acetate for 6 hours at room temperature. Filtration and evaporation of the solvent in vacuo afforded 118 mg (87% yield) of the chlorocarbons 43a/44a. (Identical to 43/44 but with the $\Delta^1$-olefinic bond removed).

(c) Ozonolysis. Chlorohydrocarbons 43a/44a (118 mg) were dissolved in a mixture of 1 ml of methanol and 2 ml of ethyl acetate and the solution chilled to $-78°$. Ozone was bubbled through the solution until a permanent blue color was produced. The solution was allowed to stand for 5 minutes and the excess ozone was flushed from the solution with oxygen. Dimethylsulfide (0.5 ml) was then added at $-78°$ with stirring and the solution stirred while warming to room temperature. After 30 minutes the solution was concentrated in vacuo to afford 135 mg of a yellow oil. Vpc on 3% XE-60/225° showed a peak at $R_t=1.25$ minutes (13%) 5β-androstan-17-one (45) at $R_t=1.5$ minutes (55%), the keto-ester (45a) at $R_t=5.75$ minutes (26%) and a peak at $R_t=9$ minutes (6%). This material was absorbed onto a silica gel plate (20 cm 20 cm $\times$ 0.1 cm) and eluted with ethyl acetate: hexane (1:4) to afford 3 bands, $R_f=0.62$, 0.42, and 0.27. The fastest moving band contained 22 mg of an oil containing four components by vpc which had no carbonyls in the infrared.

The slowest moving band contained 15 mg (11% yield) of the keto-ester (45a). Vpc on 3% XE-60/225° showed one peak at $R_t=5.75$ minutes. This material was distilled bulb-to-bulb at 150°/0.0 mm to give a clear oil.

Analysis: Calc'd for: $C_{22}H_{36}O_3$: C, 75.82; H, 10.41; O, 13.77. Found: C, 75.54; H, 10.05.

IR (film): 5.74μ(C=O), 5.88μ(C=O)

NMR (CDCl$_3$): δ0.92(S), 1.11(S), 2.14(S), 3.63(S). Mass spec: M+ 348.

The middle band afforded 24 mg (25% yield) of 5 β-androstan-17-one (45), $[\alpha]_d-48.5°$. Vpc on 3% XE-60/180° showed 93% (45) at $R_t=8$ minutes, and 7% impurity at 6 minutes.

This material coinjected with the authentic material and the IR spectra were identical.

NMR (CDCl$_3$)δ0.85(S), 0.95(S) 1R (CHCl$_3$) 5.78μ

EXAMPLE 26—Degradation of Thioketals 39/40 into 5β-androstan-17-one (45)

Similarly the thioketal mixture 39/40 required degradation of the D-homo steroid (40) to provide a true steroid (45). This was accomplished by treatment with raney nickel to remove the thioketal group followed by ozonolysis to produce the steroid (45), as follows:

(a) Treatment with Raney nickel. Into a 25 ml round-bottom flask was placed 175 mg (0.426 mmole) of the thioketal 39/40 (containing 18% of another impurity), 15 ml of ethyl acetate, 5 ml of ethanol, and ca. 3 g of wet (water) Raney nickel. This mixture was stirred at room temperature for 4 hours (vpc showed all thioketal gone) filtered to remove Raney nickel and the nickel washed several times with ethyl acetate. The organic washings were washed with brine and dried over anhydrous sodium sulfate. Filtration and evaporation in vacuo afforded 109 mg (78% yield) of a clear oil. Nmr of this material showed some vinyl protons.

(b) Ozonolysis. The above material was dissolved in a mixture of 1 ml of methanol and 3 ml of ethyl acetate and the solution chilled to $-78°$. Ozone was bubbled through the solution until a permanent blue color was produced. The solution was allowed to stand for 5 minutes and the excess ozone was flushed from the solution with oxygen. Dimethyl sulfide (0.5 ml) was then added at $-78°$ with stirring and the solution stirred while warming to room temperature. After 30 minutes the solution was concentrated in vacuo to afford 140 mg of a yellow oil. This material was absorbed into a silica gel plate (20 cm $\times$ 20 cm $\times$ 0.1 cm) and eluted with ethyl acetate:benzene (1:4) to afford 21 mg (24% yield) of 5β-androstan-17-one (45) ($R_f=0.5$) as a clear oil. This material coinjected (3% XE-60, 220°) with the authentic material and the infrared spectra were similar.

Conversion of A-Nor Steroid 42 to Other Steroids Including dl-Progesterone

Flow Sheet No. 9 and Example 24 above describe and illustrate the cyclization of substrate 34 to the A-nor steroid 42; Flow Sheet No. 10 illustrates the conversion of 42A to steroids 46 and 47; and Flow Sheet No. 11 illustrates conversion of 42A to steroid 48. A general discussion of Flow Sheets Nos. 10 and 11 follows. Examples 47 to 53 provide details.

Referring to Flow Sheet No. 10 the enol ester of formula 42A can be hydrolyzed to the 20-oxo-A-nor-pregnene compound 49 where R° is H or $CH_3$ and R'''' is H or OH. Compound 49 wherein R'''' is OH can, if desired, be reesterified at the 21-position with any desired ester moiety, preferably lower-alkanoyl of one to six carbon atoms. The 5-membered Ring A of compound 49 (where R'''' is H or lower-alkanoyloxy) is then cleaved by ozonolysis to give the tricyclic triketone 50 (R° is H or $CH_3$; R'''' is H or lower alkanoyloxy). The Ring A cleavage can also be accomplished by treating compound 49 (where R'''' is H or lower-alkanoyloxy) with excess osmium tetroxide, followed by cleavage of the osmate with hydrogen sulfide to give a diol, which is treated with excess lead tetra-acetate to yield compound 50. Compound 50 need not be isolated and purified, but can be treated directly with a cyclodehydration catalyst to produce dl-progesterone, the 21-oxy derivatives thereof or the corresponding 19-nor compounds (46; R° is H or $CH_3$; R'''' is H, OH or lower-alkanoyloxy). The cyclodehydration catalyst comprises a strong acid (for example, hydrochloric acid, hydrobromic acid, trifluoroacetic acid, p-toluenesulfonic acid, a sulfonic acid resin, or the like), a strong base (for example, sodium hydroxide, potassium hydroxide, or the like), or an amine (for example, piperidine, triethylamine, or the like), or an amine acid-addition salt (for example, triethylammonium benzoate, triethylammonium acetate, or the like). A 21-acyloxy group (R'''' is lower-alkanoyloxy), if hydrolyzed during the cyclization reaction, can be reintroduced by conventional esterification reactions.

The route leading to dl-androst-4-ene-3,17-dione and dl-19-norandrost-4-ene-3,17-dione (47, R° is $CH_3$ or H) involves ozonolysis of the enol ester 42A followed by cyclization of the resulting triketone 51.

Flow Sheet 11 shows further transformation of the A-nor steroid compound 42A to afford useful steroid structures. Compound 42A having the double bond in Ring A protected as the dibromide can be treated with a peracid, for example, monoperphthalic acid, and the bromine atoms then extracted with zinc, to give the 17,20-epoxide 52 (R° is H or $CH_3$; R''' is H, OH or OAcyl). Hydrolysis of the latter opens the epoxide ring to produce the 17α-hydroxy A-nor steroid 53 (R° is H or $CH_3$; R'''' is H or OH). Compound 53 where R'''' is OH can, if desired, be esterified to produce the compounds where R'''' is lower-alkanoyloxy. Compound 53 (R'''' is H or lower-alkanolyloxy) is then subjected to ozonolysis and the resulting triketone 54 cyclized to dl-17δ-hydroxyprogesterone, the 21-oxy derivatives thereof, or the 19-nor analogs thereof having structure 48 (R° is H or $CH_3$; R'''' is H, OH or lower-alkanoyloxy), analogous to the sequence 49→50→46.

Flow Sheet No. 12 and Examples 27 to 29 illustrate the conversion of tetracyclic ketone 41 to progesterone (57). Example 30 gives details of the synthesis of 11-methylprogesterone.

Example 27 $\Delta^1$-pregnan-3,20-dione (55) from Steroid 41

In a 25 ml flask equipped with a magnetic stirring bar were placed 284 mg (0.95 mmoles) of the enone (41), 1.60 ml of glacial acetic acid, 0.40 ml acetic anhydride and 6 ml tetrachloroethylene. The flask was placed in a 100° oil bath and the contents stirred. The oxidant solution was prepared immediately before use by adding 1.60 ml glacial acetic acid and 0.40 ml acetic anhydride to 2.75 ml of tertiary butyl chromate reagent (2.4 M in tetrachloroethylene, 7.0 equivalents). The chromate reagent solution was prepared according to the procedure of Heusler and Wetterstein (K. Heusler, A. Wetterstein, Helv. Chem. Acta 35, 384, (1952)) except that tetrachloroethylene was used rather than carbon tetrachloride. The oxidant solution was added over a 5 minute period to the stirred solution of the enone (41) at 100°. After 55 minutes at 100° the reaction vessel was allowed to cool and 5 ml of saturated aqueous oxalic acid was added, followed after 10 minutes by some solid oxalic acid. After another 10 minutes the reaction mixture was poured into a separatory funnel and extracted with ether (3 × 15 ml). The combined ether layers were washed with water then worked up as usual. Evaporation of the solvent in vacuo left the crude enedione (55), 0.253 g as a pale yellow viscous oil. Vpc analysis of this crude product showed 89% of the integrated area corresponded to the desired enedione (55). All of the above product was dissolved in the minimum amount of hexane at reflux, then allowed to cool to 23°. An oil came out of solution. On further cooling to −30° a white solid then a fluffy white product were precipitated. The supernatant was carefully removed by pipette. A total of 185 mg of material that was 95% pure by vpc was collected. The supernatant on cooling to −78° yielded more product (15 mg; total yield, 64%). Tlc (silica gel, ethyl acetate/hexane 1/1, $R_f$ 0.34) showed all the impurities remained in the −78° supernatant. A sample was purified by tlc (silica, ethyl acetate/hexane 1/1) followed by recrystallization from hexane (2 × ) that yielded white plates mp 127–131. Concentration of the mother liquor caused very fine needles mp 137–138 to crystallize. Both crystalline forms were the pure 17β isomer.

Analysis: Calc'd for: $C_{21}H_{30}O_2$ ; C, 80.21; H, 9.62. Found: C, 79.96; H, 9.59.

Spectral Data:

| | | |
|---|---|---|
| NMR: ($CCl_3$) | 0.65δ | (s, 3H, C-18) |
| | 1.20 | (s, 3H, C-19) |
| | 2.10 | (s, 3H, C-21 —C(=O)—$CH_3$) |
| | 5.92 | ( , 1H, J = 10 Hz C-2H) |
| | 6.89 | ( , 1H, J = 10 Hz C-1H) |
| IR: (KBr) | 3.42μ 3.49 (CH) | |
| | 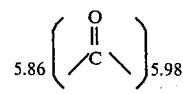 | |
| | 7.22, 7.41, 7.88, 8.25, 11.80 | |
| UV: $\lambda_{Max}^{CH_3OH}$ | 230 Mμ (E = 8.950) | |

EXAMPLE 28—Δ$^{1,4}$-pregnadien-3,20-dione (56) from 33

In a 25 ml flask were placed 0.180 g (0.572 mmoles) of Δ$^1$-pregnen-3,20-dione (55) 0.196 g (1.5 equivalents) of 2,3-dichloro-5,6-dicyano-benzoquinone, 0.140 g benzoic acid (2.0 equivalents) and 9 ml dry toluene. The flask was fitted with a condensor, degassed with nitrogen and placed in a 120° oil bath for 4 hours. The reaction mixture was then poured into saturated NaHCO$_3$ and extracted with ether (3×). The usual workup yielded 144 mg of brown oil. There was no trace of starting material by either tlc or vpc. The desired Δ$^{1,4}$-pregnadien-3,20-dione (56) integrated to 88% of the vapor phase chromatogram. A sample was purified by recrystallization from ethyl acetate/hexane (2/1) to give colorless plates mp 175°–176°.

Analysis: Calc'd for: C$_{21}$H$_{28}$O$_2$: C, 80.73; H, 9.03. Found: C, 80.68 H, 8.73.

| Spectral Data | | |
|---|---|---|
| NMR: (CDCl$_3$) | 0.68δ | (s, 3H, C-18) |
| | 1.22 | (s, 3H, C-19) |
| | 2.08 | (s, 3H, C-21) |
| | 6.03 | (m, 1H, C-4, J$_{2,4}$=2Hz) |
| | 6.16 | (q, C-2, J$_{1,2}$=10Hz, J$_{2,4}$-2Hz) |
| | 6.99 | (d 1H, C-1, J$_{1,2}$=10Hz) |
| IR: (CHCl$_3$ sol'n) | 3.32μ 3.38, 3.48 (CH) | |
| | 5.88 ( C(=O) CH$_3$) 6.02 | |
| | 6.17 (m) (C=C of A-ring) | |
| | 7.35, 7.70, 11.00, 11.22 | |

EXAMPLE 29—Progestrone (57) from 56

In a 50 ml flask equipped with a stopcock sidearm and stirrer bar were placed 144 mg of crude dienedione (56) and 30 mg Rh (Pφ$_3$)$_3$I catalyst. The flask was thoroughly degassed with hydrogen before 7 ml of toluene-/absolute ethanol (1/1, nitrogen degassed) was added via syringe. The flask was stirred under a positive pressure of hydrogenation. The resulting pale yellow orange solution was stirred 8 hours. The flask was removed from the hydrogenation apparatus and stirred in air. After solvent removal, the residue was taken up in 50% ethyl acetate in hexane then filtered through a celite/glass wool plug. Evaporation of the filtrate in vacuo left a pale brown oil, 118 mg. Vpc analysis showed that 17% of the starting material was not hydrogenated. In other experiments complete hydrogenation of the 1,2 bond has been effected. The desired product was separated from the starting material by thick layer chromatography with 2 developments in 25% ethyl acetate in hexane followed by one development in 50% ethyl acetate in hexane. Only 44 mg of crude dl-progesterone (57) was recovered. Recrystallization from methanol gave colorless plates mp 174°–184°.

| Spectral Data: | | |
|---|---|---|
| NMR: (CDCl$_3$) | 0.67δ | (s, 3H, C-18) |
| | 1.18 | (s, 3H, C-19) |
| | 2.12 | (s, 3H, C-21) |
| | 5.78 | (s, 1H, C-4) |
| IR: (KBr) | 3.35μ3.38, 3.40 (CH) | |

5.87 ( C(=O) CH$_3$) 6.00
7.35, 7.83, 8.60, 10.53, 11.45

This sample's nmr and ir spectra were ientical to the spectra of both natural progesterone and dl-progesterone.

EXAMPLE 30—Production of 11-Methyl Progesterone (a) Preparation of Cyclization Substrate 31a Into a 250 ml three-necked flask was placed 2.48 g (4.02 mmoles) of phosphonium iodide 23 (Example 12) which was then dried at 50° under high vacuum. After flushing the apparatus with dry nitrogen, 14.5 ml of dry THF were added. The partially dissolved salt was stirred magnetically at room temperature 0.99 M phenyllithium in THF was added slowly via syringe until a permanent yellow color was obtained indicating a small concentration of phosphorous ylid. Then 4.05 ml of 0.99 M phenyllithium solution (4.00 mmoles) was added all at once producing a bright cherry red solution which was then cooled to −78°. After 15 minutes at −78°, a solution of 0.65 1g (3.65 mmoles) of the aldehyde 8a (R$^1$=CH$_3$) (Example 1a) in a total of 8.0 ml of dry THF was added slowly via syringe down the side of the flask over 15 minutes. The color lightened to a pale orange and was stirred for 10 minutes. Then 6.0 ml of 0.99 M phenyllithium solution (1.5 equiv.) was added slowly via syringe down the cold side of the flask generating the very dark red betaine ylid. After 15 minutes 33 ml of dry ether was added over 5 minutes. The reaction mixture was then warmed to 0° for one hour and was then recooled to −78° for four hours after which one ml of methanol was added. After warming to room temperature while stirring overnight the reaction mixture was concentrated, poured into 50 ml of hexane and then filtered through celite. Concentration yielded 0.86 g of a light yellow oil. Vpc analysis (3% OV-17 column at 240°, 60 cc/min He flow rate) indicated two peaks in a ratio of 9:91 having retention times (RT) 12.4 and 14.0 minutes for the cis- and trans- disubstituted olefins, respectively. The crude product was purified by dry column chromatography on grade II basic alumina eluting with hexane followed by bulb to bulb distillation (190° at 0.006 mm) yielding 0.473 g (34%) of pure thioketal having the structure

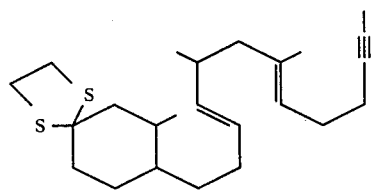

31a

Refractive Index: n$_D^{20.5}$ 1.5492

IR: λ$_{max}^{film}$ 3.30,3.42, 3.49, 6.02(C=C), 6.08 (C=C), 6.92, 6.97, 7.28, 7.86, 10.35, 11.82μ.

NMR: δ$_{CCl_4}^{TMS}$ 0.90 (3H doublet, J=6.4 Hz, 9-Methyl), 1.14–2.30 (25 H miltiplet), 1.56 (3H singlet, 7-methyl), 1.68 (3H doublet, J= 1.0 Hz, cyclohexenyl methyl), 1.72 (3H triplet, J= 2.0 Hz, CH$_3$—C≡C—), 3.22(4H singlet, —S-CH$_2$CH$_2$-S-), 4.83–5.40 (3H multiplet, C-6, C-7, C-11 vinyl H), 5.50 (1 H singlet, cyclohexenyl vinyl H).

Anal. Calc'd for $C_{24}H_{36}S_2$: C, 74.19; H: 9.34. Found: C, 74.20; H: 9.39.

As in the synthesis of dl-progesterone (Examples 15 to 18 above) the thioketal 31a was converted to an allylic alcohol 33a via the ketone 32a and the allylic alcohol 33a was used as the cyclization substrate. Details were as follows.

Into a 100 ml three-necked flask, equipped with magnetic stirrer and condenser was placed 0.548 g (1.41 mmoles) of thioketal 31a, 3.9 ml methyl iodide, 6.9 ml of water and 35 ml of acetonitrile. The resultant mixture was thoroughly degassed with nitrogen and then stirred at 38° for 24 hours. At this time the reaction mixture was poured into 100 ml of ether, washed two times with 25 ml portions of sodium thiosulfate, twice with brine, dried over magnesium sulfate and then concentrated leaving a yellow oil. Vpc analysis (3% XE-60 column at 210°, 60 cc/min. He flow rate) showed two peaks in a ratio of 9:91 having RT's of 4.0 and 4.5 minutes for the cis- and trans- disubstituted olefins, respectively. Chromatography over 40g of fluorisil while eluting with hexane, followed by bulb to bulb distillation (185° at 0.006 mm) yielded 0.441g (85%) of the pure ketone having the structure

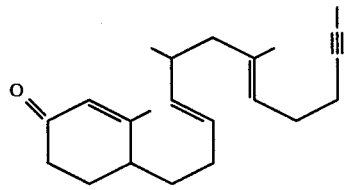

32a

Refractive Index: $D^{20.5}$ 1.3045

IR: $\lambda_{max}^{film}$ 3.28, 3.37, 3.41, 3.46, 5.97 (C=O), 6.14 (C=C), 6.88, 6.95, 7.25, 8.00, 8.34, 10.32, 11.58μ.

NMR: $\delta_{CCl_4}^{TMS}$ 0.90 (3H doublet, J-6.2 Hz, 9-methyl), 1.10–2.46 (25H multiplet), 1.56 (3H singlet, 7-methyl), 1.68 (3H triplet, J=2.5 Hz, CH$_3$-C≡C—), 1.92 (3H doublet, J=1.2 hz cyclohexenyl methyl), 5.42–4.95 (3H multiplet, C-6, C-7, and C-11 vinyl H), 5.68 (1 H singlet, cyclohexenyl vinyl H).

In a dry 50 ml three-necked flask was placed a solution of 0.62g (2.0 mmoles) of ketone 32a in 8 ml of dry THF. The flask was then flushed with dry nitrogen and cooled to 0°. While stirring, 0.50 ml of 3.00 M Redal solution (1.50 mmoles) was added dropwise over 5 minutes. After one hour, 2 ml of 5% sodium hydroxide was cautiously added to quench the reaction. Standard product isolation with ether then yielded 0.62g (99%) of a colorless liquid. TLC analysis (silica gel G, Hexane-EtOAc 4:1) indicated this crude product to be pure showing only one spot having Rf=0.17. The structure was

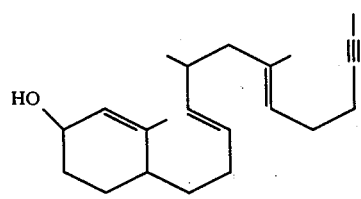

33a

IR: $\lambda_{max}^{film}$ 2.93 (O-H), 3.40, 3.48, 6.00 (C=C), 6.89, 6.95, 7.26, 8.86, 9.38, 10.30μ.

(b) Cyclization of substrate 33a to steroid 41a

A solution of 317 mg (1.01 mmole) of allylic alcohol 33a and 3.1g (35 mmoles) of ethylene carbonate in 31 ml of dry dichloroethane was cooled to −25° while vigorously stirring under dry nitrogen. To this colorless solution was then added 3.67g (32 mmoles) of trifluoroacetic acid. The reaction mixture turned light yellow and after an hour was orange in color. After three hours the reaction was quenched by pouring into 100 ml of water. The organic layer was separated and the aqueous layer extracted twice with ether. The combined organic fractions were washed twice with 25 ml portions of saturated sodium bicarbonate, once with brine, dried over magnesium sulfate and concentrated yielding a yellow oil. This material was then refluxed under nitrogen for thirty minutes with 5 ml of 5% potassium hydroxide in 4:1 methanol-water. After methanol evaporation, a standard ether workup yielded 0.242g of a light colored oil. TLC (Silica Gel HF$_{254}$, Hexane-EtOAc 4:1) showed one major component (R=0.57) in addition to at least five minor spots and a large amount of streaking. Purification by dry column chromatography (Grade III Silica Gel, Benzene) followed by bulb to bulb distillation (180° at 0.005 mm) yielded 47 mg of ketone 41a as a colorless oil. Vpc analysis (3% OV-17 column at 205°, 60cc/min He flow rate) showed two peaks, having RT's of 10.7 and 13.3 minutes, for the 17α- and 17β-epimers of 41α respectively. The structure was

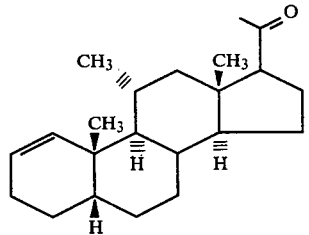

41a

IR: $\lambda_{max}^{film}$ 3.40, 3.47, 5.85 (C=O), 6.80, 6.89, 7.21, 7.36, 8.14, 8.58, 14.50μ.

NMR: $\delta_{CCl_4}^{TMS}$ 0.60 (3H singlet, 13-methyl), 1.04 (3H singlet, 10-methyl), 1.18 (3H doublet, J=6.0 Hz, 11-methyl) 2.03 (3H singlet, acetyl methyl), 0.8–2.6 (20H multiplet), 5.4–5.7 (2H multiplet). (c) The steroid 41a (11-methyl homologue of 41 in Example 22) was converted by a series of steps as in Examples 27 to 29 to dl 11-methyl progesterone. Details were as follows:

In a 25 ml three-necked flask was placed 66 mg (0.21 mmole) of ketone 41a, 1.32 ml of tetrachloroethylene, 0.35 ml of acetic acid and 0.09 ml of acetic anhydride. After flushing with nitrogen, an oxidant solution prepared from 0.35 ml acetic acid, 0.09 ml of acetic anhydride and 0.62 ml of 2.4 M t-butyl chromate reagent (1.47 mmoles) was added with stirring at room temperature. The reaction mixture was then stirred at 65°–70° for one hour. It was then green in color. After cooling, 0.5 ml of saturated oxalic acid was added and after 10 minutes this mixture was extracted with ether. The combined ether extracts were washed twice with 5 ml portions of saturated sodium bicarbonate, dried over magnesium sulfate and concentrated yielding a yellow oil. The crude product was purified by preparative TLC (Silica Gel HF$_{254}$-Hexane-EtoAc 1:1) followed by bulb to bulb distillation (250° at 0.005 mm) to yield 30 mg (44%) of a colorless oil. Vpc analysis (3% OV-17 column at 225°.

A solution of 32.5 mg (0.144 mmole) of 2,3-dichloro-5,6-dicyanobenzoquinone, 23.5 mg (0.192 mmole) of benzoic acid and 30 mg (0.096 mmole) of dione 55a from the preceding step in 1.50 ml of dry toluene was prepared in a 3 ml flask and flushed with dry nitrogen. The mixture was then heated to reflux for four hours. After cooling 10 ml of ether was added. The organic solution was washed four times with saturated sodium bicarbonate solution, dried over magnesium sulfate and concentrated yielding 31.5 mg of a green oil. Purification by preparative TLC (Silica Gel HF254, Hexane-EtOAc 1:1) yielded a crystalline substance from which 11.1 mg of off-white crystals mp 148°–155°, were obtained after one recrystallization from hexane-ethyl acetate).

IR: $\lambda_{max}^{CHCl_3 soln}$ 3.38, 3.46, 5.87 (C=O), 6.16 (C=C), 6.23 (C=C), 6.87, 7.09, 7.18, 7.37, 7.68, 11.17μ.

NMR: $\delta_{CDCl_3}^{TMS}$ 0.70 (3H singlet, 13-methyl), 1.10 (3H doublet, J=6 cps 11-methyl), 1.28 (3H singlet, 10-methyl), 2.10 (3H singlet, acetyl methyl), 0.8–2.7 (15H multiplet), 6.08 (1H singlet, 4-vinyl H), 6.14 (1 H doublet J=9Hz, 2-vinyl H), 7.15 (1 H doublet, J=9 Hz, 1-vinyl H).

The structure was:

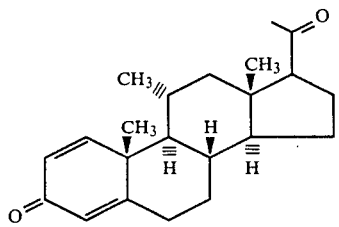

A solution of 11 mg of dione 56a from the preceding step was prepared in 3.0 ml of 1:1 toluene-ethanol while stirring in a 5 ml flask. This solution was degassed by bubbling hydrogen through it for 30 minutes. To this mixture was then added 14 mg of Rh (φ3P)3 I catalyst. Hydrogen was slowly bubbled through the reaction mixture while stirring overnight. The catalyst was then removed by a filtration through 10 g of Grade II alumina, eluting with ether. The product thus obtained was further purified by preparative TLC (Silica Gel HF254 Hexane-EtOAc 1:1). This yielded 4.5 mg of colorless needles.

IR: $\lambda_{max}^{film}$ 3.40, 3.48, 5.86C=O), 5.98 (C=O), 6.20 (C=C), 6.92, 7.24, 7.40, 7.88, 8.08, 8.22, 8.44, 8.62, 10.68, 11.55, 11.85

NMR: λ-hd CDCl3$^{TMS}$ 0.66 (3H singlet, 13-methyl), 1.10 (3H doublet, J=6 Hz, 11-methyl), 1.23 (3H singlet, 10-methyl), 2.10 (3H singlet, acetyl methyl), 0.8–2.6 (19 H multiplet), 5.74 (1 H singlet, 4-vinyl H).

The product was dl 11-methyl progesterone 57a having the structure

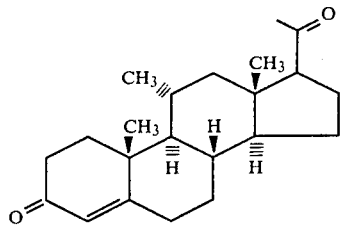

EXAMPLE 31

In the production of steriods having a C-3 keto group and a Δ$^4$ olefinic group (double bond at C-4, C-5), as in Examples 27 to 30 above, the initial steriod is subjected to certain transformations, among them oxidation at C-3 to afford a C-3 keto group and reactions which convert

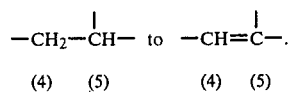

Synthesis of such steriods, including important steriods such as progesterone, cortisone and related or derivative steriods, can be considerably simplified and improved as to yield by employing an ylide fragment III (or its aldehyde counterpart III A) wherein the C-3 has a substituent which is readily modified to a keto group, where the A and B rings of the resulting steriod are

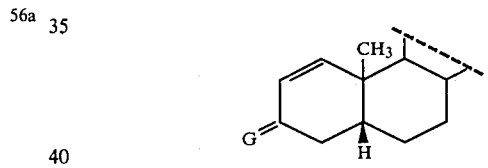

Subsequent catalystic hydrogenation of the $^1$-olefinic bond followed by oxidative cleavage (e.g. ozone) of the G$^1$ = C< group will result in steroids of partial structure A. Bromination

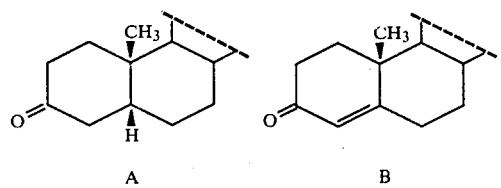

dehydrobromination of A will then afford a group of steriods of partial structure B of which progesterone, 11-methylprogesterone, cortisone, etc. are members.

Use of Nitro Alkanes and of Olefins as Trapping Agents

In the examples above relating to the cyclization of substrate I, the use of protonic acids such as trifluoroacetic acid and of Lewis acids such as stannic chloride has been described. These acids also function to trap the cation at C-20 which results from cyclization. The mechanism of trapping is discussed below under the heading of Mechanism Involved in the Cyclization Reaction. Two other classes of useful trapping agents —nitro alkanes and olefins —are described in Flow Sheets Nos. 13 and 14, respectively and in Examples 32 to 34. Yet another trapping agent is trifluoroethanol; see example 60.

EXAMPLE 32

Treatment of a solution of cyclization substrate 33 in dry 2-nitropropane with trichloroacetic acid, followed by aqueous sodium bicarbonate workup and purification by preparative TLC on Silica Gel (1:99 EtOAc-hexane: continuous elution for 4 hr) gave the isomeric oxime ethers 58 in 45% yield (ca. 1:1 mixture of 17-α-acetyl: 17-β-acetyl isomers by nmr). Evaporative distillation (190° at 0.01 mm) afforded an analytically pure sample (Anal. Found: C, 77.8; H, 10.0; N, 3.7); $\nu_{max}^{CCL_4}$ 1712 (C=O), 1639 (C=N) cm$^{-1}$. The nmr spectrum (60 MHz, CCl$_4$, TMS internal standard) included singlets at $\delta$0.58 (3H, C-18 of β-acetyl isomer), 0.93 (3H, C-18 of α-acetyl isomer), 0.99 (6H, C-19, both isomers) and at 1.86 (3H), 1.88 (3H), 1.92 (3H), and 1.94 (3H) for the methyl groups adjacent to the carbonyl and oxime groups. In addition there were two singlets at 5.48 and 5.52 (2H total) for the olefinic protons.

EXAMPLE 33—Conversion of Oxime Ether 58 to a Mixture of 17-α and 17-β hydroxypregnan-20-ones Reduction of the oxime ether 58 to the glycol 59 was carried out with excess lithium aluminum hydride in refluxing tetrahydrofuran in an atmosphere of nitrogen, which cleaved the N-O bond and also reduced the carbonyl group. 59 is a mixture of four stereoisomers which was identified (as a mixture) by nmr and infrared spectra. The $\Delta^1$ olefinic bond of 59 was reduced by hydrogenation with palladium on activated carbon in ethyl acetate at 23° to afford the diol 59A which was oxidized by aqueous N-bromosuccinimide to 60.

Details will be found in Johnson, Morton and Gravestock U.S. Pat. Application Ser. No. 354,532 entitled "Synthesis of Steroids by Cyclization in Nitro Solvents" filed Apr. 26, 1973, Example 5. In addition, the diol 59 was subjected to oxidative cleavage with periodic acid to produce a keto group at C-17, which was reduced to afford a steroid having an hydroxy group at C-17. The benzoic acid ester of this alcoholic group was formed, the C-3position of the benzoate was oxidized to afford a C-3 keto group; the $\Delta^1$-olefinic group was reduced; the resulting ketone (saturated A-ring) was converted to the enol acetate ($\Delta^3$ group, i.e., C-3, C-4 double bond introduced); bromination resulted in the regeneration of the C-3 keto group and introduced a C-4 bromine and dehydrobromination resulted in dl-testosterone benzoate.

The nitro alkane trapping agent may be used as the reaction solvent as in Example 32 above or a co-solvent, preferably constituting 70% or more of the solvent. Examples of suitable nitro alkanes are any of the various primary or secondary nitro alkane series such as nitromethane, nitroethane, symmetrical and unsymmetrical nitro propanes; and of the various primary and secondary C$_4$ to C$_{12}$ nitro alkanes, etc.; also cycloaliphatic nitro aliphatic compounds provided the carbon atom attached to the nitro group is a secondary carbon atom having a hydrogen atom attached thereto such as nitrocyclohexane, nitrocyclopentane, nitrocyclopropane, etc. The alkyl or cycloaliphatic group may be substituted by non-aliphatic groups and by hetero atoms and functional groups which do not interfere with formation of the oxime ether and with the cyclization reaction. Examples of non-aliphatic substituents are phenyl (e.g. phenyl nitro methane), substituted phenyl (e.g. substituted by alkyl or halogen). The aliphatic groups may have unsaturation. Mixtures of two or more aliphatic nitro compounds may be used. Unsubstituted low molecular weight nitro alkanes such as nitromethane, nitroethane and the nitropropanes are preferred because they are inexpensive, they are liquid at the reaction temperatures and the excess is easily removed because the solvent is volatile.

Among the advantages of using a nitro alkane as the trapping agent is that the group at C-20 lends itself to reduction to a glycol group, thus

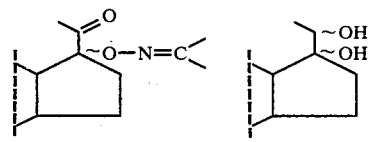

and this glycol group is readily converted, e.g., to a C-17 keto group as described above and this derivative in turn can be converted to a testosterone derivative.

EXAMPLE 34

The allylic alcohol 33 is treated with boron trifluoride etherate in the presence of a large excess of isohexene to produce the triene 62, most probably as a mixture of $\Delta^{22}$ and $\Delta^{23}$ isomers (so indicated on Flow Sheet No. 14 by the dotted lines). Catalytic hydrogenation of this triene generates coprostane 63. Alternatively, cyclization of 33 in the presence of isohexene with TFA produces the diene ester 64 which on hydrolysis results in the alcohol 65.

Synthesis of Cyclization Substrate I by Reversal of Ylide and Aldehyde

The cyclization substrate generally designated as I (a specific example being the substrate 31) are described above as being prepared by condensation of an ylide III which bears the cyclization initiator Z with an aldehyde IV which bears the acetylenic group —C≡C—R$^1$. It is quite feasible to reverse the procedure and to make the Z— fragment as an aldehyde and the acetylenic fragment as an ylide, thus

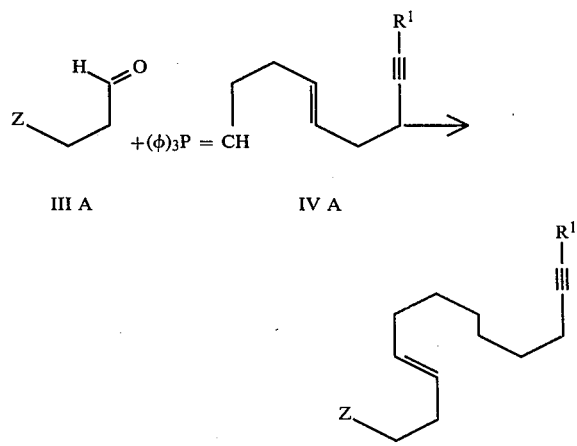

(It will be understood that Z, and R$^1$ are as defined above and that the various carbon atoms in III A and IV A may be substituted by alkyl groups.) Example 35 below illustrates the III A (aldehyde) + IV A (ylide) →I route.

EXAMPLE 35

(a) Synthesis of Aldehyde F

The reaction scheme was as follows:

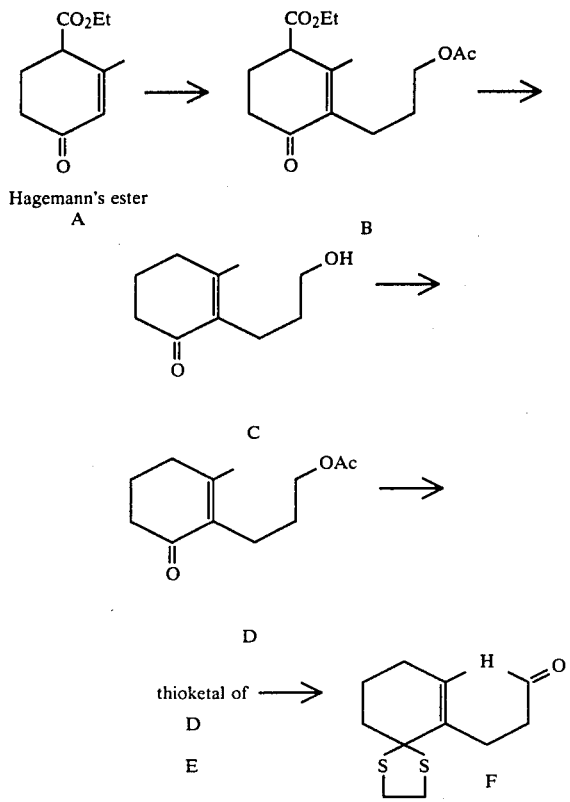

To a suspension of 5.65 g of 57% sodium hydride- oil dispersion (0.134 mole of sodium hydride) in 90 ml dry tetrahydrofuran at 25° under an atmosphere of nitrogen was added dropwise a solution of 25.7 g (0.134 mole) of Hagemann's ester A (Aldrich, 95% pure) in 40 ml of dry tetrahydrofuran. The mixture was heated to 40° to insure complete enolate formation and then was allowed to cool to 25°. To this suspension was added a mixture containing 18.3 g (0.134 mole) of chloroacetate Cl—$CH_2$—$Ch_2$—$CH_2$—OAc, 5.08 g (0.034 mole) of sodium iodide, and 110 ml of dry acetonitrile. The reaction mixture was stirred at 65° for 42 hr. (reaction was complete after 18 hr. by vpc analysis) and then the mixture was concentrated in vacuo and the product was isolated with ether, affording 36.3 g of diester B. Vapor phase chromatographic analysis revealed that the ratio of product to starting material was 1.7 to one.

A solution containing 36.3 g of crude diester B, 17.6 g (0.27 mole) of 86% KOH (Baker, "Analyzed" Reagent), and 110 ml of absolute ethanol was degassed, filled with nitrogen and was stirred at reflux for 2 hr. The reaction mixture was cooled to 0° under a nitrogen atmosphere and 85 ml of water was added. Following this, a solution of 29 ml of conc, hydrochloric acid and 56 ml of water was added slowly since carbon dioxide evolution accompanied the addition of acid. After the addition was complete, the reaction mixture was again degassed and stirred at reflux under nitrogen for 0.5 hr. The solution was allowed to cool to ambient temperature overnight and then most of the ethanol was removed in vacuo. The product was isolated with ether, affording 12.4 g of orange keto alcohol C:
$\lambda_{max}^{film}$ 2.89, 6.01, and 6.02.

To a solution of the crude keto alcohol C (12.4 g calculations based on 100% purity, 0.073 mole) in 12 ml of dry pyridine was added 10.5 ml (0.111 mole) of acetic anhydride. The reaction mixture was stirred at 25° under an atmosphere of nitrogen for several hours. It was then poured into aqueous hydrochloric acid and the product was isolated with ether. Fractional distillation afforded 6.2 g of keto acetate D.

To a solution of 1.06 g (5.0 mmole) of keto acetate D and 1.72 ml (20.0 mmole) of 1,2-ethanedithiol in 8.5 ml of chloroform at 25° was added 0.41 ml (3.31 mmole) of boron trifluoride etherate (distilled). The reaction mixture (in a flask fitted with a $CaCl_2$ drying tube) was stirred at 25° for 24 hr. The mixture was poured into aqueous sodium hydroxide and the product was isolated with ether to give 1.448 g (100%) of thioketal E.

To a suspension of 244 mg (6.42 mmole) of lithium aluminum hydride in 10 ml of dry ether at 0° under an atmosphere of nitrogen was added a solution of 1.45 g (5.06 mmole) of ketal acetate D (purified by column chromatography) in 5 ml of ether dropwise over a period of 17 min. An additional 5 ml of ether was used to rinse the addition funnel. The ice bath was removed and the reaction was stirred at 25° for 0.5 hr. At this time 0.24 ml of water, 0.24 ml of 15% aqueous sodium hydroxide, and 0.72 ml of water were sequentially added to the reaction mixture. The mixture was stirred overnight and then magnesium sulfate was added and the resulting precipitates were filtered. The solvents were removed in vacuo to give 1.273 g (100%) of white viscous liquid (alcohol E).

A mixture containing 1.235 g (5.06 mmole) of alcohol E, 3.14 g (15.2 mmole) of dicyclohexylcarbodiimide, 17.1 ml of dry benzene, and 17.1 of dry dimethylsulfoxide was degassed several times and filled with nitrogen. To this mixture was added 0.41 ml (5.06 mmole) of dry pyridine followed by 0.19 ml (2.53 mmole) of trifluoroacetic acid. The mixture was stirred at 25° for 65 hr then benzene was added and the solution was filtered. The benzene solution was extracted several times with water, was dried over anhydrous sodium sulfate and the solvents were removed in vacuo to give 1.605 g of semi-solid.

The crude reaction product was chromatographed on 60 ml of Silica Gel (Brinckman, 0.05-0.2 mm) in hexane solution. The aldehyde was eluted with 20'% ether in hexane to give 1.15 g (93%) of semi-solid material which was 92% pure by vapor phase chromatography. This represents an 86% overall yield of material;
$\lambda_{max}^{film}$ 3.63 and 5.79µ; $\delta_{CCl_4}^{TMS}$ 1.62(S). 3.23(S), and 9.70 ppm (S).

(b) Synthesis of Ylide 8A.

The reaction scheme was as follows:

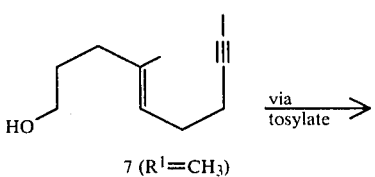

7 ($R^1$=$CH_3$)

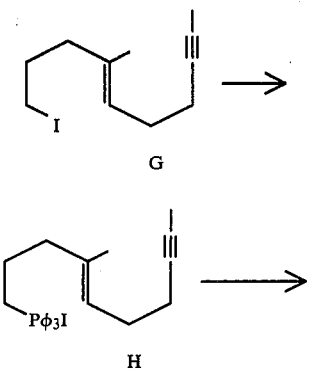

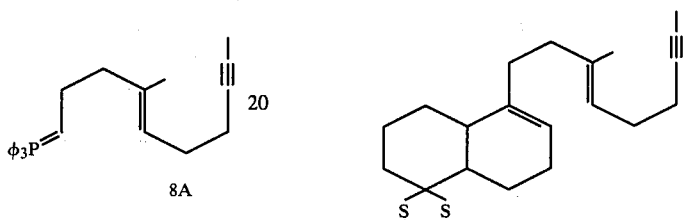

The tosylate of alcohol 7 (preparation of which is described in Example 38) was prepared using p-toluene sulfonyl chloride in pyridine at 0° under nitrogen. This tosylate was converted to the iodide G by reaction with sodium iodide in acetone under nitrogen at 25°. The iodide G was converted to the phosphonium salt H as follows:

A mixture containing 553 mg (2.0 mmole) of iodide G, 735 mg (2.82 mmole) of triphenylphosphine (MCB, mp 80°-81°), 3 drops of diisopropylethyl amine, and 2.3 ml of dry acetonitrile was degassed thoroughly and was stirred at 52° under nitrogen for 17 hr. The mixture was cooled to room temperature and 5.5 ml of dichloromethane was added. This solution was then poured into 41 ml of hexane and after stirring vigorously, the hexane was decanted away. The resulting oily residue was washed in the same manner five times with 5 ml portions of hexane. All traces of solvents were removed by evacuating the flask to 0.02 mm Hg at 24° overnight to afford 1.049 g (97%) of a yellow glass.

The ylide 8A was formed in situ; see section (c) below.

(c) Condensation of Ylide 8A with Aldehyde F

A mixture of 601 mg (1.12 mmole) of phosphonium salt H and 3.5 ml of dry tetrahydrofuran was degassed, filled with nitrogen, and was stirred at room temperature until solution was complete. To this was added 0.62 ml of a 2.0 M phenyllithium in tetrahydrofuran solution. Initially 0.06 ml of phenyllithium was added in order to produce a sustained yellow color, then 0.56 ml (1.12 mmole) additional phenyllithium solution was added. This deep-red solution was stirred at 25° for 10 min and then was cooled to −78° and stirred for 10 min. To the ylide solution (ylide 8A) at −78° under nitrogen was added 268 mg (1.12 mmole) of aldehyde F along with 1.3 ml of tetrahydrofuran and the mixture was stirred for 10 min. At this time, 1.05 ml of 2.0 M phenyllithium in tetrahydrofuran solution was added and the resulting solution was stirred at −78° for one hour to allow for complete formation of the second ylide. To the now deep-red solution was added slowly, down the sides of the flask, 5.85 ml of dry ether. The solution was then warmed to −30° and 0.5 ml of methanol was added slowly. The mixture then was stirred at −30° to 25° overnight. The reaction mixture was poured into water and the product was isolated with ether.

The crude reaction product was chromatographed carefully on a column of 6 g of Fisher Florisil (100–200 mesh) prepared in hexane. The thioketal product was eluted with hexane and afforded 309 mg (73%) of a clear, colorless liquid: $\delta_{CCl_4}^{TMS}$ 1.60(S), 1.65(S), 1.72(S), 2.05(broad S) 2.20 (broad S), 3.25(S), 5.14(m), and 5.38 ppm (m). This material was essentially pure by vapor phase chromatography. The stereochemistry about the disubstituted double bond was ascertained to be 97% trans and 3% cis. The trans species had the structure

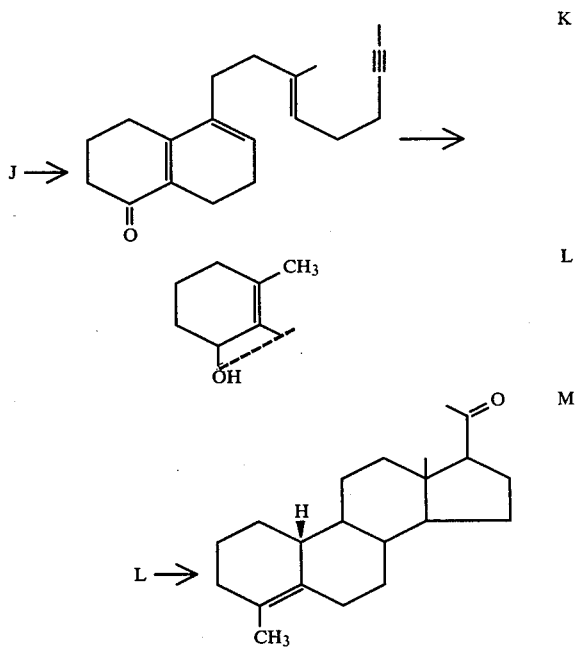

(d) Conversion of J to Ketone K and of K to Alcohol L and Cyclization of L

The reaction scheme was as follows:

A mixture containing 309 mg (0.825 mmole) of thioketal J, 1.3 ml (0.028 mole) of methyl iodide, 12.4 ml of dry acetonitrile, and 2.5 ml of deionized water was degassed, filled with nitrogen, and was stirred at 43° overnight. Most of the acetonitrile was removed in vacuo and the product was isolated with ether to give 246 mg (100%) of yellow liquid. Thin-layer chromatography of this material revealed that there were two components present (Silica Gel HF$_{254}$, 1:1 ether-hexane) at Rf=0.47 and Rf=0.68. The former (Rf—0.47)

was identified as K and was separated by thin layer chromatography.

To a solution of 24.5 mg (0.0822 mmole) of the ketone K in 1.5 ml of dry tetrahydrofuran at 0° under an atmosphere of nitrogen was added an excess of Redal (3.54 M lithium di (methoxyethoxy) aluminum hydride in benzene). The reaction mixture was stirred at 25° for 1.5 hr then aqueous sodium hydroxide was added carefully. The reaction mixture was poured into aqueous sodium hydroxide and the product was isolated with ether; $\lambda_{max}^{film}$ 2.97, 6.00, 10.32μ; $\delta_{CCl_4}^{TMS}$ 1.53 (broad S), 1.63 (S), 3.84(m) 5.04(m), and 5.27 ppm(m).

To a solution of 284 mg (3.22 mmole) of ethylene carbonate in 0.85 ml of dichloromethane at −78° under an atmosphere of nitrogen was added 0.185 ml (2.5 mmole) of trifluoroacetic acid and the mixture was stirred for ca. 5 min. To this mixture was added, via syringe, the crude alcohol L (based on 0.0822 mmole) along with 1.0 ml of dichloromethane. After 45 min. the temperature of the reaction bath had risen to −50° and after 1.3 hr., the temperature was approaching 0°. An ice bath was placed around the reaction flask and the mixture was stirred at 0° for 20 min. then 2.0 ml of a 10% potassium carbonate in 50% aqueous methanol solution was added. This mixture was stirred at 25° overnight and then it was poured into water and the product was isolated with ether.

The crude product was purified by preparative thin-layer chromatography (Silica Gel HF$_{254}$, 15% ether-hexane) to afford 10 mg (40%) of yellow crystalline material, M. $\delta_{CCl_4}^{TMS}$ 0.62(S), 1.57(S), and 2.00 ppm(S).

Further details in the synthesis of aldehyde 8 (See Flow Sheet No. 2 and Example 1 above) are set forth in Examples 36 to 38 below.

EXAMPLE 36—(Precursors to Hexynal 5 and Preparation of Alcohol 3)

(a) 3-Carboethoxy-6-chlorohept-5-en-2-one (cis/trans).

To a solution of 46 g sodium (2 g atom) in 500 ml ethanol at reflux, in a 2-liter flask equipped with mechanical stirrer, and addition funnel, was added 325 g ethyl acetoacetate (2.5 mole) over 30 minutes. The resulting solution of enolate was refluxed for 15 minutes, and then 250 g (2.0 mole) 1,3-dichlorobut-2-ene (n$_D^{20}$ 1.4675) was added dropwise at such a rate as to maintain reflux with gentle heating towards the end of the addition. After addition, refluxing and stirring were maintained for 4 hours, the condenser converted for distillation, and ethanol removed as 500 ml distillate. The residual product was cooled, water and 1.2 N hydrochloric acid were added and the organic layer separated. The aqueous portion was extracted with ether, the organic layers combined, washed with water and brine, filtered through sodium sulfate and evaporated in vacuo to give 485 g. dark yellow oil (96%, based on dichlorobutene). Vpc showed 73% of trans plus cis product, together with 20% ethyl acetoacetate and other volatiles, and 7% dialkylated product at long retention time. A small sample was purified by TLC on silica gel (1:3 ethyl acetate:pentane) R$_f$0.27, followed by distillation at 100° C./0.1 mm. 3-Carboethoxy-6-chlorohept-5-en-2-one was obtained as a colorless oil, n$_D^{20}$ 1.4640.

(b) Methyl 4-hexynoate. (Precursor to Hexynal 5)

Crude 3-carbethoxy-6-chlorohept-5-en-2-one from part (a) above, 242 g, was added dropwise (at such a rate as to maintain reflux) to 264 g (4 mole) 85% potassium hydroxide dissolved in 250 ml 95% ethanol in a 2-liter 3-necked flask equipped with mechanical stirrer, reflux condenser and addition funnel. After the addition the condenser was converted for distillation, 150 ml ethylene glycol and 50 ml 2-ethoxyethanol (b.p. 133°-135° C.) were added, and ethanol/water distilled off until the pot-temperature had reached 130°-135° C. Stirring and heating under reflux werethen continued for 5 hours at 130°-135° C., the reaction mixture cooled to about 80° C., 1 liter brine added, the mixture stirred for 2-3 hours at room temperature and then poured into a separatory funnel. After washing with ether (3×150 ml), the aqueous solution was then acidified with cold concentrated hydrochloric acid to pH 6.5, extracted with chloroform, acidified to pH 1.0, and again extracted with chloroform. The pH 1.0 extracts were washed with 200 ml brine, filtered through sodium sulfate and evaporated in vacuo to give 67.1 g (60% based on dichlorobutene) pale brown crystalline solid (after removal of acetic acid by azeotroping with 1,4-dioxan and vacuum drying). A small sample of the acid was purified by crystallization from benzene: pentane and vacuum sublimation to give 4-hexynoic acid, colorless needles, m.p. 99°-100° C.

(b) Methyl 4-hexynoate. (Precursor to Hexynal 5)

Crude 3-carboethoxy-6-chlorohept-5-en-2-one from part (a) above, 242 g, was added dropwise (at such a rate as to maintain reflux) to 264 g (4 mole) 85% potassium hydroxide dissolved in 250 ml 95% ethanol in a 2-liter 3-necked flask equipped with mechanical stirrer, reflux condenser and addition funnel. After the addition the condenser was converted for distillation, 150 ml ethylene glycol and 50 ml 2-ethoxyethanol (b.p. 133°-135° C.) were added, and ethanol/water distilled off until the pot-temperature had reached 130°-135° C. Stirring and heating under reflux were then continued for 5 hours at 130°-135° C., the reaction mixture cooled to about 80° C., 1 liter brine added, the mixture stirred for 2-3 hours at room temperature and then poured into a separatory funnel. After washing with ether (3×150 ml), the aqueous solution solution was then acidified with cold concentrated hydrochloric acid to pH 6.5, extracted with chloroform, acidified to pH 1.0, and again extracted with chloroform. The pH 1.0 extracts wer washed with 200 ml brine, filtered through sodium sulfate and evaporated in vacuo to give 67.1 g (60% based on dichlorobutene) pale brown crystalline solid (after removal of acetic acid by azeotroping with 1,4-dioxan and vacuum drying). A small sample of the acid was purified by crystallization from benzene: pentane and vacuum sublimation to give 4-hexynoic acid, colorless needles, m.p. 99°-100° C.

The crude acid was dissolved in 150 ml. dry methylene dichloride and 48 g methanol, and refluxed for 20 hours with 0.50 g. p-toluenesulfonic acid monohydrate. The reaction mixture was cooled, diluted with saturated sodium bicarbonate solution, separated and the aqueous layer extracted with ether. The combined organic extracts were washed with saturated sodium bicarbonate solution, and the product isolated to give 58 g. orange oil. Distillation in vacuo through a small Vigreux column gave 51.0 g. methyl 4-hexynoate as colorless oil, b.p. 77°-78° C./21 mm.

(c) 4-Hexynal. 11

4-Methyl hexynoate (25.0 g., 0.20 mole) was dissolved in 100 ml. dry tetrahydrofuran in a 500 ml. flask equipped with mechanical stirrer and addition funnel with provision for "Dry-Ice"/acetone cooling. To the stirred solution at −70° C. under dry N$_2$ was added over 1 hour, 70 ml. of a 3.54 M solution of sodium bis (2-methoxyethoxy) aluminum hydride in benzene diluted to 140 ml. (total volume) with dry tetrahydrofuran from the cooled addition funnel. The product was then stirred for 5 hours at −70° C. and then 14.2 ml (11 g.) (0.25 mole) acetaldehyde, b.p. 20°-22° C. was added slowly by syringe. After 10 minutes at −70° C. the reaction mixture was poured into a mixture of 100 ml. concentrated hydrochloric acid and 500 ml. saturated brine. The mixture was ether extracted and the extracts washed with 50 ml. saturated sodium bicarbonate solution and with 50 ml. brine, then filtered through Na$_2$SO$_4$ and evaporated in vacuo at 20° C. The crude 4-hexynal was used directly for the next step after drying over "4A"-molecular sieves to remove ethanol. A purified specimen showed the following properties: b.p. 70° C./20 mm.; n$_D^{20}$ 1.4524; 2,4-dinitrophenylhydrazone, m.p. 119.5-120° C.

(d) 2-Methyloct-1-en-6-yn-3-ol (3; R' is CH$_3$) - 3

Magnesium (14.4 g., 0.6 g atom) was dried in a 250 ml. flask fitted with reflux condenser, mechanical stirrer and addition funnel. After initiation of reaction under dry N$_2$ with about 1 ml. ethylene dibromide in 70 ml. tetrahydrofuran, 36.0 g. (0.30 mole) 2-bromopropene (n$_D^{20}$1.4425) was added dropwise at such a rate as to maintain reflux without external heating. The Grignard solution was then stirred until it cooled to room temperature (30 minutes-1 hour). It was then cooled further to −15° C. in ice-salt, and the total crude 4-hexynal 11 from part (c) above was added dropwise over 15 minutes. The reaction mixture was stirred for 2 hours at room temperature, saturated ammonium chloride solution was added and the product was extracted with ether. There was obtained 23.50 g. of 2-methyloct-1-en-6-yn-3-ol, 3, (85%, based on 4-methyl hexynoate) as a pale yellow oil.

Apart from small samples for characterization, the alcohol was rather unstable to distillation or chromatography, and was used crude in the next step for best overall yields. TLC on silica gel (1:2 ethyl acetate:pentane) R$_f$ 0.70, and distillation 60° C./0.05 mm. gave a colorless oil.

Anal. Calcd. for C$_9$H$_{14}$O: C, 78.21; H, 10.21. Found: C, 78.14; H, 10.15 The nmr spectrum indicated the triplet at 1.76δ characteristic of the methylacetylenic residue.

2-Methyloct-1-en-6-yn-3-ol (3, R is CH$_3$) was alternatively prepared from methacrolein 1 and the Grignard reagent 2 derived from 1-bromo-3-pentyne. (Flow Sheet No. 1)

If in the foregoing preparation of 2-methyloct-1-en-6-yn-3-ol (3 R$^1$ is CH$_3$), the 4-hexynal 11 is replaced by a molar equivalent amount of 5-trimethylsilyl-4-pentynal [(CH$_3$)$_3$SiC≡C-CH$_2$CH$_2$CHO], there can be obtained 2-methyl-7-trimethylsilylhept-1-en-6-7n-3-ol [3, R$^1$ is Si(CH$_3$)$_3$]. The intermediate 5-trimethylsilyl-4-pentynal can be obtained by condensing 3-dimethoxy-propyl chloride [ClCH$_2$CH$_2$CH(OCH$_3$)$_2$] with lithium acetylide and treating the resulting dimethoxypropylacetylene [HC≡CCH$_2$CH$_2$CH-(OCH$_3$)$_2$] with trimethylsilyl chloride in the presence of butyllithium, followed by acid hydrolysis of the acetal, (CH$_3$)$_3$SiC≡CCH$_2$CH$_2$CH (OCH$_3$)$_2$.

EXAMPLE 37—Methyl trans-4-methyldec-4-en-8-ynoate (13 R$^1$ is CH$_3$)

2- Methyloat-1-en-6-yn-3-ol 3, 11.75 g (85% pure, 0.0725 mole), was dissolved in 53 g. trimethyl orthoacetate (b.p. 107°-108° C.) (0.44 mole) (6 equivs.) together with 0.50 g. propionic acid (6.7 mmole), and the mixture heated in a 115° C. oil bath under N$_2$, condenser, and a Dean-Stark trap with heating tape for 16 hours. The reaction mixture was cooled, poured into water and extracted with ether. The ethereal extracts were washed (3x) with 1.2 N hydrochloric acid and the product isolated to give 14.24 g. orange oil. The crude ester from two of the above runs, 28.14 g., was distilled in vacuo through a small Vigreux column to give 19.5 g of methyl trans-4-methyldec-4-en-8-ynoate 13 as colorless oil, b.p 75°-77° C./0.1 mm. (50% from 4-methyl hexynoate) (>98% pure by vpc) (less than 1% cis isomer) n$_D^{20}$1.4694.

Anal. Calcd. for C$_{12}$H$_{18}$O$_2$: C, 74.19; H, 9.34. Found: C, 73.92; H, 9.26.

ir (liq film) λ$_{max}$3.42, 5.75, 8.64μ. The nmr spectrum indicated a singlet at 1.62δ characteristic of a methyl group on a trans-trisubstituted olefinic bond, and a triplet at 1.76 for the methylacetylenic residue.

By an analogous procedure, 5-trimethylsilyl-4-pentynal can be caused to react with trimethyl orthoacetate to give methyl trans-4-methyl-9-trimethylsilylnon-4-en-8-ynoate 13; R$^1$ is (CH$_3$)$_3$Si, Alk is CH$_3$.

EXAMPLE 38—Trans-4-Methyldec-4-e-8-ynal (8 R$^1$ is CH$_3$).

Methyl trans-4-methyldec-4-en-8-ynoate 13, 4.84 g. (25 mmole), was dissolved in 15 ml. dry tetrahydrofuran in a 250 ml. flask equipped with mechanical stirrer and addition funnel equipped with a "Dry Ice"-acetone cooling jacket. The solution was cooled with stirring under dry N$_2$ to −70° C., and 10.5 ml. of 3.54 M sodium bis (2-methoxyethoxy) aluminum hydride in benzene diluted with 11 ml. dry tetrahydrofuran was added from the cooled funnel over 1 hour. The product was stirred for 5 hours after the addition, and then 3.45 ml (2.65 g., 60 mmole) acetaldehyde was added by syringe, dropwise, the mixture stirred for 10 minutes at −70° C. and poured into 400 ml of 1.2 hydrochloric acid. Ether extraction (3×75 ml.) and isolation gave 4.05 g. colorless oil (98%) which vpc showed to contain 87% desired aldehyde (8) and 13% of the corresponding alcohol (7). See Flow Sheet No. 1. The alcohol was separated from the aldehyde by Florisil ® (activated magnesium silicate) chromatography and elution of the latter with pentane. A sample of trans-4-methyldec-4-en-8-ynal 8 was obtained pure by tlc, silica gel (1:2 ethyl acetate:pentane) R$_f$ 0.64, and distillation, b.p. 70° C./0.025 mm.

Anal. Calcd. for C$_{11}$H$_{16}$O: C, 80.44; H, 9.83. Found: C, 80.69; H, 9.75.

n$_D^{20}$ 1.4824, ir (liq film) λmax 3.43, 3.69, 5.76, 6.95μ. The nmr spectrum included a singlet at 1.57δ and a triplet at 1.71; in addition there was a singlet at 9.80 for the aldehyde portion.

Alternatively, methyl trans-4-methyldec-4-en-8-ynoate 6 was reduced with lithium aluminum hydride in ether (1 hour at 0°) to give trans-4-methyldec-4-en-8- ynol (7; $R^1$ is $CH_3$) (b.p. 80° C./-0.025 mm.), and the latter oxidized with dipyridine chromic oxide complex in methylene dichloride (1.2 hours at 23° C. to the aldehyde, trans-4-methyldec-4-en-8-ynal (7; $R^1$ is $CH_3$). (See Flow Sheet No. 1)

By analogous procedures, methyl trans-4-methyl-9-trimethylsilylnon-4-en-8-ynoate [6; $R^1$ is $(CH_3)_3SI$, Alk is $CH_3$] can be reduced to trans-4-methyl-9-trimethylsilylnon-4-en-8-ynol [7, $R^1$ is $Si(CH_3)_3$] and/or trans-4-methyl-9-trimethylsilylnon-4-en-8-ynal [8, $R^1$ is $Si(CH_3)_3$].

The following Examples Nos. 39 to 41 provide further details of the synthesis of the phosophonium iodide 30 (see Flow Sheet No. 4 above) which is converted (see Example below and Flow Sheet No. 4 above) to the ylide 25 which, however, is not isolated but is employed in the reaction solution to condense with aldehyde 8 to produce cyclization substrate precursor 35.

EXAMPLE 39

(a) 2-Methyl-5-(4-bromobutyl) furan (27)

To an oven-dried 2-liter 3-necked flask equipped with a mechanical stirrer and a nitrogen inlet were added 700 ml. tetrahydrofuran (distilled from lithium aluminum hydride) and 61.5 g. (0.75 mole) of 2-methylfuran (distilled from calcium hydride, b.p. 64° C.). The solution was cooled to −30° C. and 350 ml. of a solution of n-butyllithium in hexane (2.28 M, 0.80 mole) was added via syringe. The temperature was maintained between −20° C. and −30° C. The mixture was stirred for 4 hours, the flask cooled to −60° C. and 467 g (2.16 mole, 2.9 equiv.) of 1,4-dibromobutane (b.p. 82°–83.5° C., 15 mm.; precooled to −25° C. was added all at once. The clear yellow solution was allowed to warm slowly to room temperature overnight. The reaction mixture was poured into water (250 ml.) overlaid with ether (300 ml.) and the organic layer was washed with dilute acid (2×50 ml.) The aqueous layer was extracted with ether (2×100 ml.) and the combined organic layers were washed with bicarbonate and brine and dried over anhydrous magnesium sulfate. The volatile solvents were removed under reduced pressure leaving an orange liquid (about 350 ml.). The product was distilled through an 8-inch Vigreux column. Hydroquinone (50 mg.) was added to inhibit free radical reactions. Distillation fractions were identified as follows: fraction 1, 307 g., b.p. 36° C./0.10 mm. (dibromobutane); fraction 2, 30.3 g., b.p. 42° C./0.015 mm. at 50° C./0.015 mm. [dibromobutane and 2-methyl-5-(4-bromobutyl) furan]; redistilled to yield 22.8 g. of 2-methyl-5-(4-bromobutyl) furan, b.p. 50° C./0.015 mm.; fraction 3, 95.2 g. of 2-methyl-5-(4-bromobutyl) furan, b.p. 50° C./0.015 mm. Yield: 118 g. (72.5%).

Anal. Calcd. for $C_9H_{13}OBr$: C, 49.76; H, 6.04; Br, 36.8. Found: C, 49.82; H, 6.10; Br, 36.8.

Ir: $\lambda_{max}^{film}$ 6.2, 6.4, 9.8, 12.8µ (furan); 8.0, 8.2 ($RCH_2Br$), $n_D^{22}$ 1.5002. The nmr spectrum included a singlet at 2.12δ for the methyl group, a triplet at 3.37 for the protons α to the bromine, and a singlet at 5.82 for the protons at C3 and C4 on the furan ring.

(b) 1-Bromonona-5,8-dione bis (ethylene ketal) (28 n is 2).

In a 1-liter 3-necked flask equipped with nitrogen inlet, mechanical stirrer and a Dean-Stark trap with condenser were placed 500 ml. of benzene, 180 ml. of ethylene glycol (200 g., 3.2 moles), 3.0 g. of para-toluenesulfonic acid monohydrate and about 100 mg. of hydroquinone. The mixture was stirred and refluxed for 6 hours to remove any water. Then 111 g. of 2-methyl-5-(4-bromobutyl) furan (27) (0.51 mole) was added, the flask shielded from light and the stirring and reflux continued. After 43 hours, the mixture was allowed to cool and poured into a separatory funnel, and the brown glycol layer allowed to separate. The benzene layer was washed with saturated bicarbonate (2×100 ml.) then with brine (2×50 ml.) filtered through anhydrous sodium sulfate and the solvent removed under reduced pressure to give 158 g. (165 g. theoretical of pale yellow-brown liquid. The crude product (69 g.) was applied to a column of 1 kg. of 100–200 mesh Florisil ® (activatedmagnesium silicate). Unreacted bromofuran (27) (9.5 g.) was eluted with hexane. The desired 1-bromonona-5,8-dione bis (ethylene ketal) (28) (51 g., 71% conversion, 88% yield corrected for recovered starting material) was eluted with 15% ether in hexane. Vpc analysis indicated >99% purity. The analytical sample was prepared by bulb-to-bulb distillation at 140° C./0.05 mm.

Anal. Calcd. for $C_{13}H_{23}O_4Br$: C, 48.28; H, 7.17; Br, 24.7. Found: C, 48.39; H, 7.22; Br, 24.84.

The nmr spectrum included a singlet at 1.22δ for the methyl group, a singlet at 1.56 for the two methylene groups flanked by the ketal residues, a triplet at 3.35 and a pair of singlets at 3.83 and 3.85 for the four ketal methylene groups.

By replacing the ethylene glycol in the foregoing preparation by a molar equivalent amount of propylene glycol, there can be obtained 1-bromonona-5,8-dione bis (propylene ketal) (28) n is 3).

EXAMPLE 40

1-Iodonona-5,8-dione bis (ethylene ketal) (29 n is 2).

A suspension of 39.6 g. of the aforementioned 1-bromonona-5,8-dione bis (ethylene ketal) (28 0.123 mole), 26.4 g. of drysodium iodide (0.176 mole, 1.4 equivalents) and 150 ml. of dry 2-butanone was degassed and stirred under nitrogen for 40 minutes at 80° C. The reaction mixture was poured into dilute bicarbonate and the product extracted with ether. The ether layer was washed with a sodium thiosulfate solution, saturated bicarbonate and brine, then filtered through anhydrous sodium sulfate. The solvent was removed under reduced pressure to give 44.9 g. of almost colorless 1-iodonona-5,8-dione bis(ethylene ketal) (99% yield). This was used directly in the next step. An analytical sample was prepared by bulb-to-bulb distillation at 145° C./0.05 mm.

Anal. Calcd. for $C_{13}H_{23}O_4I$: C, 42.18; H, 6.26: I, 34.28. Found: C, 42.40; H, 6.13; I, 34.54.

The nmr spectrum was similar to that of the corresponding bromo compound, including a triplet at 3.20δ for the protons α to the iodine.

By an analogous procedure 1-bromonona-5,8-dione bis (propylene ketal) can be converted to 1-iodonona-5,8-dione bis (propylene ketal) (29 n is 3).

EXAMPLE 41

Nona-5,8-dione bis (ethylene ketal)-1-triphenylphosphonium iodide (30 n is 2)

In a 100 ml. flask with a magnetic stirrer bar were placed 1.13 g. (3.1 mmoles) of 1-iodonona-5,8-dione bis (ethylene ketal) (Example 5), 1.14 g. triphenylphosphine (4.4 mmoles, 1.4 equivalents) and about 5 ml. of dry benzene. The solution was degassed and stirred under nitrogen at 80° C. for 11 hours. The phosphonium salt was precipitated with 20 ml. of dry ether. The supernatant was removed and the thick white oil washed with another 10 ml. of dry ether. This oil was dissolved i 6 ml. of dry acetone from which it began to crystallize. The stirred suspension was cooled to 0° C. while 30 ml. of dry ether was added slowly. After removal of the supernatant, the phosphonium salt was washed with 10 ml. of dry ether and then dried under reduced pressure to give 1.81 g. of nona-5,8-dione bis(ethylene ketal)-1-triphenylphosphonium iodide )94% yield), as a loose, white powder.

Anal. Calcd for $C_{31}H_{38}O_4PI$: C, 58.86; H, 6.06; P, 4.90; I, 20.06. Found: C, 59.00; H, 6.02; P, 4.79; I, 19.52.

Ir ($CHCl_3$) $\lambda_{max}$ 6.33, 6.78, 6.99, 9.02, 14.07μ. The nmr spectrum included features similar to that of the bromide 28 and, in addition, a multiplet at 3.62δ for the $CH_2-P^+$ protons and a multiplet at 7.7–8.1 for the aromatic protons.

By a similar procedure, 1-iodonona-5,8-dione bis (propylene ketal) can be converted to nona-5,8-dione bis (propylene ketal)-1-triphenylphosphonium iodide (30 n is 3).

Examples 42 to 46 below provide details of the preparation of the ylide 25 (in solution, not isolated) its condensation with the aldehyde 8 and conversion of the product of condensation to the cyclization substrate 34 (See also Flow Sheet No. 6 above). Examples 47 to 53 provide details of the cyclization of substrate 34 to an A-nor steroid and transformation of the resulting A-nor steroid to natural (6-membered A ring) steroids. (See also Flow Sheets Nos. 9, 10 and 11).

EXAMPLE 42

7-Methylnonadeca-trans,trans-6,10-dien-2-yn-15,18-dione bis (ethylene ketal) (35; $R^1$ is $CH_3$, n is 2)

The phosphonium salt (30 n is 2), 4.45 g. (recrystallized from acetone) (7 mmole) was dispersed in 25 ml. dry tetrahydrofuran under dry $N_2$, and treated with 7 ml. 1.02 M phenyllithium in ether. The resulting deep-red ylid (25 n is 2) solution was cooled to −70° C., and 1.15 g. trans-4-methyldec-4-en-8-ynal (8 $R^1=CH_3$) (7 mmole) (>98% pure) was added dropwise by syringe in 10 ml. dry ether. The mixture was stirred for 5 minutes at −70° C., warmed to −30° C., 8 ml. 1.02 M phenyllithium syringed into the resulting red ylid solution which was stirred for a further 5 minutes, and then 1 ml. methanol was added dropwise by syringe at −30° C. Trphenylphosphine oxide was precipitated immediately. The mixture was stirred for a few hours at room temperature, and the product was poured into water and ether extracted. Isolation of the product gave 2.86 g. yellow oil after two triturations from pentane. The triphenyl-phosphine oxide and volatile impurities were removed by chromatograpy on Florisil ® (activated magnesium silicate). Elution with pentane: 10% ether gave 1.64 g. 7-methylnonadeca-trans,trans-6,10-dien-2-yn-15,18-dione bis (ethylene ketal) as colorless oil. The analytical sample was further purified by tlc, silica gel (1:2 ethyl acetate:pentane) $R_f$=0.32, and distillation, b.p. 190° C./0.01 mm.

Anal. Calcd. for $C_{24}H_{38}O_4$: C, 73.80; H, 9.81. Found: C, 74.10; H, 9.70.

Ir (liq film) $\lambda_{max}$ 3.45, 6.90, 7.30, 9.58, 10.30, 10.52μ. The nmr spectrum included a singlet at 1.39δ for the methyl on the ketal carbon, a singlet at 1.63, a triplet at 1.75, a singlet at 3.94 for four ketal methylene groups, and a multiplet at 5.41 for the vinyl hydrogens of the trans-disubstituted olefinic bond.

By replacing the phosphonium salt (30 n is 2) in the foregoing preparation by the corresponding bis (propylene ketal) (30 n is 3) there can be obtained 7-methylnonadeca-trans,trans-6,10-dien-2-yn-15,18-dione bis(propylene glycol) (35 R' is $CH_3$, n is 3).

By replacing the trans-4-methyldec-4-en-8-ynal in the foregoing preparation by trans-4-methyl-9-trimethylsilylnon-4-en-8-ynal [8 $R^1$ is $Si(CH_3)_3$], there can be obtained 1-trimethylsilyl 6-methyloctadeca-trans,trans-5,9-dien-1-yn-14,17-dione bis (ethylene ketal) [35 $R^1$ is $(CH_3)_3Si$, n is 2]. The latter can be treated with aqueous alcoholic silver nitrate to replace the trimethylsilyl group by hydrogen to provide 6-methyloctadeca-trans,-trans-5,9-dien-1-yn-14,17-dione bis(ethylene ketal) (35 $R^1$ is H, n is 2). The latter in the presence of a strong base such as sodium methoxide reacts with formaldehyde to give 1-hydroxy-7-methylnonadeca-trans,trans-6,10-dien-2-yn-15,18-dione bis (ethylene ketal) (35 $R^1$ is $CH_2OH$, n is 2).

EXAMPLE 43

7-Methylnonadeca-trans,trans-6,10-dien-2-yn-15,18-dione (36 R″ is H)

The bis ketal (35 $R^1$ is $CH_3$, n is 2) (Example 42), 2.75 g. was dissolved in 100 ml. methanol, degassed under $N_2$, 30 ml. 0.1 N hydrochloric acid added and degassed again under $H_2$. The reaction mixture was stirred at 40° C. for 6 hours under $N_2$. Solid sodium bicarbonate was added until the mixture was basic, and the solvent removed in vacuo. Ether and water were added, and the product extracted and isolated to give 2.25 g. 7-methylnonadeca-trans,trans-6,10-dien-2-yn-15,18-dione, as a pale yellow oil. A sample was purified for analysis by tlc, silica gel (1:2 ethyl acetate:pentane) $R_f$ 0.25, and distilled to give colorless oil, b.p. 190° C./0.01 mm.

Anal. Calcd. for $C_{20}H_{30}O_2$: C, 79.42; H, 10.00. Found: C, 79.40; H, 9.88.

The nmr spectrum included a singlet at 2.21δ for the methyl ketone group.

By a similar procedure, 1-hydroxy-7-methylnonadeca-trans,trans-6,10-dien-2-yn-15,18-dione bis (ethylene ketal) (35 R' is $CH_2OH$, n is 2) can be hydrolyzed to give 1-hydroxy-7-methyl-nonadeca-trans,trans-6,10-dien-2-yn-15,18-dione (36 R″ is OH).

EXAMPLE 44

2-(7-Methyltrideca-trans,trans-3,7-dien-11-ynyl)-3-methylcyclopent-2-enone (36A R″ is H).

The crude dione (36 R″ is H) (Example 43), 2.25 g., was dissolved in 30 ml. methanol and added to 70 ml. of 2% aqueous sodium hydroxide. The resulting solution was degassed under $N_2$ and heated at reflux for 18 hours. The methanol was removed in vacuo, and the product diluted with water and ether extracted to give on isolation, 2.20 g. crude cyclopentenone derivative as yellow oil. Chromatograhy on Florisil ® (activated magnesium silicate) and elution with pentane: ether (9:1) gave 920 mg. 2-(7-methyltrideca-trans,trans-3,7-dien-11-ynyl)-3-methylcyclopent-2-enone as a colorless oil [46% based on aldehyde (8)]. Vpc showed two peaks corresponding to 97% of the trans-disubstituted double bond compound and 3% of the cis isomer. In a separate experiment an analytical sample was prepared by tlc purification on silica gel (1:4 ethyl acetate:pentane) $R_f$ 0.40, and distillation, b.p. 190° C./0.05 mm.

Anal. Calcd. for $C_{20}H_{28}O$: C, 84.45; H, 9.92. Found: C, 84.33; H, 9.77.

Ir (liq film) $\lambda_{max}$ 3.43, 5.86, 6.05, 6.94, 7.20, 10.29μ.
Uv (MeOH) $\lambda_{max}$ 235 mμ (10,400).

By an analogous procedure, 1-hydroxy-7-methylnonadeca-trans,trans-6,10-dien-2-yn-15,18-dione (36; R" is OH) can by cyclized to give 2-(13-hydroxy-7-methyltrideca-trans,trans-3,7-dien-11-ynyl)-3-methylcyclopent-2-enone (36A; R" is OH).

EXAMPLE 45

2-(7-Methyltrideca-trans,trans-3,7-dien-11-ynyl)-1,3-dimethylcyclopent-2-enol (34 R° is $CH_3$, R" is H)

The cyclopentenone derivative (36A; R" is H) (Example 44), 210 mg (0.74 mmole), was dissolved in 5 ml dry ether together with a few crystals of 1,10-phenanthroline. Methyllithium (2 M in ether) was added dropwise by syringe under $N_2$ until a permanent yellow-brown color was achieved, and the mixture was stirred for 2 minutes at room temperature. The mixture was then quenched by dropwise addition of water, diluted with more water and ether extracted to give after isolation, 219 mg pale yellow oil containing 2-(7-methyltrideca-trans,trans-3,7-dien-11-ynyl)-1,3-dimethylcyclopent-2-enol. Since the alcohol dehydrates easily and the resultant polyenes polymerize readily, an analysis was not obtained and the crude material was always used directly for cyclization in the subsequent reaction.

Ir (liq film) $\lambda_{max}$ 2.70–3.22, 3.38, 6.92, 7.20, 9.20, 10.30μ.

By an analogous procedure, 2-(13-hydroxy-7-methyltrideca-trans,trans-3,7-dien-11-ynyl)-3-methylcyclopent-2-enone 36A; R" is OH) can be treated with methyllithium to give 2-(13-hydroxy-7-methyltrideca-trans,trans-3,7-dien-11-ynyl)-1,3-dimethylcyclopent-2-enol (34; R° is $CH_3$, R" is OH).

EXAMPLE 46

2-(7-Methyltrideca-trans,trans-3,7-dien-11-ynyl)-3-methylcyclopent-2-enol (34 R° is H, R" is H)

can be prepared by treating 2-(7-methyltrideca-trans,trans-3,7-dien-11-ynyl)-3-methylcyclopent-2-enone (36A; R" is H) with sodium borohydride in aqueous ethanol at room temperature for about five hours.

Similarly, 2-(13-hydroxy-7-methyltrideca-trans,trans-3,7-dien-11-ynyl)-3-methylcyclopent-2-enone (36A; R" is OH) can be reduced with sodium borohydride to give 2-(13-hydroxy-7-methyltrideca-trans,trans-3,7-dien-11-ynyl)-3-methylcyclopent-2-enol (34; R° is H, R" is OH).

EXAMPLE 47

3-Methyl-A-nor-3-pregnen-20-one (49 R° is $CH_3$, R"" is H)

2-(7-Methyltrideca-trans,trans-3,7-dien-11-ynyl)-1,3-dimethylcyclopent-2-enol 34 (Example 45), 219 mg. (0.70 mmole), was dissolved in a 10:1 mixture of dichloroethane (dist. from $P_2O_5$):-ethylene carbonate (24.2 g) in a 50 ml flask, the mixture stirred and degassed under $N_2$ at 0° C., and 0.80 ml (1.23 g, 10.8 mmole) trifluoroacetic acid (b.p. 71°–73° C.) was added dropwise. The solution turned a yellow color, and eventually to a deep-red. The reaction mixture was stirred for 1.5 hours at 0° C. and an additional 0.80 ml trifluoroacetic acid was added with stirring for an additional 1.5 hours at 0° C. To the resulting mixture was added 20 ml of a 10% potassium carbonate solution in water; methanol (50:50), and the mixture stirred finally for 1 hour at room temperature. The mixture was poured into water, ether extracted and the product isolated to give 238 mg dark orange oil. Vpc inspection showed 70% of 3-methyl-A-nor-3-pregnen-20-one and 13% of the corresponding 17α-isomer, together with 6% unreacted starting material. The crude mixture was chromaographed directly on 12 g. Florisil ® (activated magnesium silicate) using degassed pentane. Pentane gave vpc volatile impurities, followed by 158 mg of the desired product in 10% ether: pentane, the earlier fractions being richer in the 17-α form. A sample of the product was submitted for analysis after distillation at 190° C./0.05 mm. [Single spot on silica gel (1:2 ethyl acetate:-pentane) $R_f$ 0.69].

Anal. Calcd. for $C_{21}H_{32}O$: C, 83.94; H, 10.73. Found: C, 83.77; H, 10.62.

The remainder of the sample was recrystallized from pentane at −20° C. to give 3-methyl-A-nor-3-pregnen-20-one as colorless leaves, m.p. 82°–88° C. (showing 9.5% α-form by vpc). A further crystallization gave m.p. 88°–89° C. ir ($CH_3Cl$) $\lambda_{max}$ 3.42, 5.86, 6.90, 7.40μ. The nmr spectrum included singlets at 0.65μ for the C-19 methyl, 0.92 for the C-18 methyl, 1.58 for $CH_3C=C$, and 2.13 for the C-21 methyl.

3-Methyl-A-nor-3-pregnen-20-one was also prepared by treating a methylene dichloride solution of 2-(7-methyltridecatrans,trans-3,7-dien-11-ynyl)-1,3-dimethylcyclopent-2-enol with stannic chloride and then with water.

By analogous procedures, 2-(13-hydroxy-7-methyltrideca-trans,trans-3,7-dien-11-ynyl)-1,3-dimethylcyclopent-2-enol (34 R° is $CH_3$, R" is OH); 2-(7-methyltrideca-trans,trans-3,7-dien-11-ynyl)-3-methylcyclopent-2-enol (34 trans, R° is H, R" is H); or 2-(13-hydroxy-7-methyltrideca-trans,trans-3,7-dien-11-ynyl)-3-methylcyclopent-2-enol (34: R° is H, R" is OH) can be cyclized with trifluoroacetic acid and hydrolyzed with potassium carbonate to give, respectively, 21-hydroxy-3-methyl-A-nor-3-pregnen-20-one (49 R° is $CH_3$, R"" is OH); 3-methyl-A, 19-bisnor-3-pregnen-20-one (49; R° is H, R"" is H); or 21-hydroxy-3-methyl-A,19-bisnor-3-pregnen-20-one (49; R° is H, R"" is OH).

21-Hydroxy-3-methyl-A-nor-3-pregnen-20-one (49 R° is $CH_3$, R"" is OH) can be esterified with acetic anhydride, butyric anhydride or caproyl chloride in pyridine to give, respectively, 21-acetoxy-3-methyl-A-nor-3-pregnen-20-one (49; R° is $CH_3$, R"" is $OCOCH_3$), 21-butyryloxy-3-methyl-A-nor-3-pregnen-20-one[49: R° is $CH_3$, R"" is $[OCO(CH_2)_2CH_3]$ or 21-caproyloxy-3-methyl-A-nor-3-pregnen-20-one [49 R° is $CH_3$, R"" is $OCO(CH_2)_4CH_3$].

EXAMPLE 48 dl-Progesterone (46 R° is $CH_3$, R"" is H).

A 150 mg. sample of 3-methyl-A-nor-3-pregnen-20-one (Example 47) (about 95% pure) (0.5 mmole) in 15 ml. of methanol and 5 ml. of methylene dichloride was added to bulb "B" of a Rubin ozonizer containing 14 ml. of ozone-saturated methylene dichloride at −70° C. in bulb "A" (0.55 mole $O_3$). The ozone solution was then forced slowly, by $N_2$ pressure, into the ketone solution stirred at −70° C. After 2 minutes at −70° C., the colorless solution was warned to −15° C., and 10 ml. acetic acid, 2 ml water and 1 g zinc dust were added and stirred for 30 minutes at room temperature. The reaction mixture was filtered, diluted with water and ether extracted. The product was isolated to give 146 mg triketone (50 R° is CH$_3$, R'''' is H) as a near-colorless oil (88%). Tlc showed a major spot at R$_f$ 0.26 on silica gel (1:2 ethyl acetate:pentane). Ir showed (liq film) $\lambda_{max}$ 3.42$\mu$, 5.88 (broad). The triketone (50) was not characterized further but submitted crude to aldol conditions.

The triketone (50) (146 mg) was dissolved in 5 ml methanol, degassed under N$_2$ and 2 ml. of a 5% methanolic potassium hydroxide solution added by syringe. The reaction mixture was stirred at room temperature for 20 hours, poured into water, ether extracted and worked-up to give 126 mg. pale yellow oil which crystallized slowly. The crude product was chromatographed on a 1000$\mu$ silica gel tlc plate (anal. plate R$_f$=0.33, 1:2 ethyl acetate:pentane, identical with d-progesterone) with 4:6 ethyl acetate:pentane (degassed). The major uv active band yielded 71 mg. crystalline solid. Vpc showed >95% pure, $\beta$;$\alpha$-progesterone (8.5:1.5). The sample was dissolved in methanol and diluted with ether. Cooling produced colorless plates, m.p. 180–183° C. A further methanol crystallization produced colorless prisms, m.p. 182°–185° C., identical by mixed m.p. with a sample of dl-progesterone, m.p. 182°–185° C., prepared according to Johnson et al., Tetrahedron, Suppl. 8, Part II, 541 (1966). The synthetic sample was identical by ir (CH$_2$Cl$_2$), nmr (CDCl$_3$ 60 MHz) and mass spectrum (70 eV) with natural progesterone. Ir (CH$_2$Cl$_2$) $\lambda_{max}$ 3.40, 5.88, 6.00, 7.40, 10.50, 11.53$\mu$.

By analogous procedures, 21-acetoxy-3-methyl-A-nor-3-pregnen-20-one (49 R° is CH$_3$, R'''' is OCOCH$_3$); 3-methyl-A, 19-bisnor-3-pregnen-20-one (49; R° is H, R'''' is H); or 21-acetoxy-3-methyl-A,19-bisnor-3-pregnen-20-one (49 R° is H, R'''' is OCOCH$_3$) can be submitted to ozonolysis and aldol cyclization of the intermediate triketone (50) to give, respectively, dl-21-hydroxy-pregn-4-ene-3,20-dione (46 R° is CH$_3$, R'''' is OH); dl-21-hydroxy-19-norpregn-4-ene-3,20-dione (46; R° is H, R'''' is H); or dl-21-hydroxy-19-norpregn-4-ene-3,20-dione (46 R° is H, R'''' is OH).

EXAMPLE 49

3-Methyl-20-trifluoroacetoxy-A-norpregna-3,17(20)-diene(42A R° is CH$_3$, R''' is H, W is OCOCF$_3$).

2-(7-Methyltrideca-trans,trans-3,7-dien-11-ynyl)-1,3-dimethylcyclopent-2-enol 34(Example 45), 25 mg., was dissolved in 2 ml. dry, olefin-free pentane and 0.20 ml. dry dichloroethane. The mixture was cooled to 0° C. and degassed under N$_2$, and then 0.12 ml. trifluoroacetic acid was added giving a dark-orange solution; a further 0.12 ml of acid after 15 minutes produced as further color change. The reaction mixture was stirred for 1.0 hour at 0° C., poured into water and ether extracted to give 30 mg 3-methyl-20-trifluoroacetoxy-A-norpregna-3,17 (20)-diene as a yellow oil. Ir (liq film) $\lambda_{max}$ 3.43, 5.60 (CF$_3$COOR), 5.90 (C=C), 8.20 (C-O) indicated the expected enol trifluoroacetate structure.

By analogous procedures, using in place of trifluoroacetic acid, formic acid (15 minutes in pentane at 23° C.), or $\alpha,\beta$-dibromopropionic acid, there can be obtained, respectively, 3-methyl-20-formyloxy-A-norpregna-3,17(20)-diene (42A; R° is CH$_3$R''' is H, W is OCOH); or 3-methyl-20-(2,3-dibromopropionoxy)-A-norpregna-3,17(20-diene [42A; R° is CH$_3$, R''' is H, W is OCOCH(Br)CH$_2$Br].

Similarly, 2-(7-methyltrideca-trans,trans-3,7-dien-11-ynyl)-1,3-dimethylcyclopent-2-enol34(Example 45) when treated with trifluoroacetic acid and sodium iodide or benzene, gave, respectively, 3-methyl-20-iodo-A-norpregna-3,17(20)-diene (42A R° is CH$_3$, R''' is H, W is I), or 3-methyl-20-phenyl-A-norpregna-3,17(20)-diene (42A; R° is CH$_3$, R''' is H, W is C$_6$H$_5$).

Similarly, 2-(13-hydroxy-7-methyltrideca-trans,trans-3,7-dien-11-ynyl)-1,3-dimethylcyclopent-2-enol (34 R° is CH$_3$, R'' is OH); 2-(7-methyltrideca-trans,trans-3,7-dien-11-ynyl)-3-methylcyclopent-2-enol (34 R° is H, R'' is H); or 2-(13-hydroxy-7-methyltrideca-trans,trans-3,7-dien-11-ynyl)-3-methylcyclopent-2-enol (34 R° is H, R'' is OH) can be cyclized in the presence of trifluoroacetic acid to give, respectively, 3-methyl-20,21-bis-(trifluoroacetoxy)-A-norpregna-3,17(20)-diene (42A R° is CH$_3$, R''' is OCOCF$_3$, W is OCOCF$_3$); 3-methyl-20-trifluoroacetoxy-A,19bisnorpregna-3,17(20)-diene (42A R° is H, R''' is H, W is OCOCF$_3$; or 3-methyl-20,21-bis(-trifluoroacetoxy)-A,19 -bisnorpregna-3,17(20)-diene (42A R° is H, R''' is OCOCF$_3$, W is OCOCF$_3$).

EXAMPLE 50 dl-Androst-4-ene-3,17-diene (47 R° is CH$_3$).

The 3-methyl-20-trifluoroacetoxy-A-norpregna-3,17(20)-diene prepared in Example 49 was subjected to controlled ozonolysis in the same manner as in Example 48. The resulting triketone (51; R° is CH$_3$) was subjected to aldol condensation conditions as in Example 48, and the product isolated to give 15 mg. yellow oil. Vpc showed a major peak identical by coinjection with dl-androst-4-ene-3,17-dione prepared by an alternative process. After partial purification tlc (silica gel HF$_{254}$) 90% pure, the sample showed the same mass spectrum and ir (liq. film) $_{max}$ 3.44, 5.79, 6.01 and 6.20 shown by androst-4-ene-3,17-dione derived from natural sources.

Similarly, 3-methyl-20-trifluoroacetoxy-A,19-bisnorpregna-3,17(20)-diene (42 R° is H, R''' is H, W is OCOCF$_3$) can be subjected to ozonolysis to give a triketone (51 R° is H) and the latter cyclized to dl-19-norandrost-4-ene-3,17-dione (47 R° is H).

EXAMPLE 51

17,20-Epoxy-3-methyl-20-trifluoroacetoxy-A-norpregn-3-ene (52 R° is CH$_3$, R''' is H, W is OCOCF$_3$) can be prepared by reacting 3-methyl-20-trifluoroacetoxy-A-norpregna-3,17(20)-diene (42A R° is CH$_3$, R''' is H, W is OCOCF$_3$) (Example 49) with bromine, treating the resulting 3,5-dibromo-3-methyl-20-trifluoroacetoxy-A-norpregn-17(20)-ene with monoperphthalic acid in ether solution at room temperature for about 15 hours, and debrominating the dibromo-epoxide with zinc.

Similarly, 3-methyl-20,21-bis(trifluoroacetoxy)-A-norpregna-3,17(20)-diene (42A R° is CH$_3$, R''' is OCOCF$_3$, W is OCOCF$_3$); 3-methyl-20-trifluoroacetoxy-A,19-bisnorpregna-3,17-diene (42A R° is H, R''' is H, W is OCOCF$_3$); or 3-methyl-20,21-bis(trifluoroacetoxy)-A,19-bisnorpregna-3,17(20)-diene (42A R° is H, R''' is OCOCF$_3$, Wis OCOCF$_3$) can be converted, respectively, to 17,20-epoxy-3-methyl-20,21-bis(trifluoroacetoxy)-A-norpregn-3-ene (52 R° is CH$_3$, R''' is OCOCF$_3$, Wis OCOCF$_3$); 17,20-epoxy-3-methyl-20-trifluoroacetoxy-A,19-bisnorpregn-3-ene (52 R° is H, R''' is OCOCF$_3$, W is OCOCF$_3$).

EXAMPLE 52

17α-Hydroxy-3-methyl-A-norpregn-3-en-20-one (53; R° is CH₃, R"" is H)

can be prepared by treating 17,20-epoxy-3-methyl-20-trifluoroacetoxy-A-norpregn-3-ene (Example 51) with sodium methoxide in methanol, at room temperature for about three hours.

Similarly, 17,20-epoxy-3-methyl-20,21-bis(trifluoroacetoxy)-A-norpregn-3-ene (52 R° is CH₃, R''' is OCOCF₃, W is OCOCF₃); 17,20-epoxy-3-methyl-20-trifluoroacetoxy-A,19-bisnorpregn-3-ene (52 R° is H, R"" is H, W is OCOCF₃); or 17,20-epoxy-3-methyl-20,21-bis(trifluoroacetoxy)-A,19-bisnorpregn-3-ene (52 R° is H, R''' is OCOCF₃, W is OCOCF₃) can be subjected to basic cleavage to produce, respectively, 17α,21-dihydroxy-3-methyl-A-norpregn-3-en-20-one (53 R° is CH₃, R"" is OH); 17α-hydroxy-3-methyl-A,19-bisnorpregn-3-en-20-one (53 R° is H, R"" is H); or 17α,21-dihydroxy-3-methyl-A,19-bisnorpregn-3-en-20-one (53 R° is H, R"" is OH).

EXAMPLE 53 dl-17α-Hydroxypregn-4-ene-3,20-dione (48 R° is CH₃, R"" is H)

can be prepared according to the procedure of Example 48 by ozonolysis of 17α-hydroxy-3-methyl-A-norpregn-3-en-20-one (Example 52), and acidic aldol condensation of the resulting triketone (54 R° is CH₃, R"" is H).

Similarly, 17α-hydroxy-21-acetoxy-3-methyl-A-norpregn-3-en-20-one (53; R° is CH₃, R"" is H); 17α-hydroxy-3-methyl-A,19-bisnorpregn-3-en-20-one (53 R° is H, R"" is OCOCH₃); or 17α-hydroxy-21-acetoxy-3-methyl-A,19-bisnorpregn-3-en-20-one (53 R° is H, R"" is OCOCH₃) can be subjected to ozonolysis, and aldol condensation of the intermediate tricyclic ketones (54) to produce, respectively, dl-17α,21-dihydroxypregn-4-ene-3,20-dione (48 R° is CH₃, R"" is OH); dl-17α-hydroxy-19-nor-pregn-4-ene-3, 20-dione (48R° is H, R"" is H); or dl-17α,21-dihydroxy-19-norpregn-4-ene-3,20-dione (48 R° is H, R"" is H).

VII. Conclusion

The subject method provides a convenient procedure for preparing polycyclic compounds having the hydrindane, cyclopentanoperhydronaphthalene and cyclopentanoperhydrophenanthrene cyclic structures with a substituent on the cyclopentane ring. By employing an initiator molecule with from 0 to 2 3-butenylene groups between the initiator and a 3-butyne group, upon treatment with acid, the polyenyne compound cyclizes to a polycyclic product having a cyclopentane ring.

The subject process employing an alkyne terminator is useful whenever one wishes to cyclize to a polycyclic product having a substituted cyclopentane ring. The formation of the cyclopentane ring is particularly important in the synthesis of steroids, since the cyclopentane D ring is achieved directly unlike prior synthetic techniques. In earlier cyclization methods, a homo D ring was formed which had to be cleaved and recyclized to the desired 5-membered ring. This is disadvantageous in adding at least two additional synthetic steps, so that overall yields of the desired final product are reduced. Furthermore, by appropriate choice of the nucleophile, one can vary the substituent at the C-17 position, whereby one can have the cholestane side chain, the stigmastane side chain, the pregnane side chain, etc., with various functionalities at C-17, C-20 and C-21.

What is claimed is:

1. A method for preparing a cyclization product having a structure B

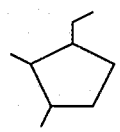

from a substrate having the structure A

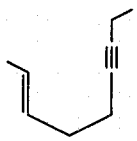

the method comprising:
contacting said substrate in a solvent with from about 1 to 50 equivalents of a Lewis acid per equivalent of said substrate at a temperature in the range of about −50 to 10° C.

2. A method according to claim 1, wherein R¹ is methyl and said Lewis acid is selected from the group consisting of trifluoroacetic acid, trichloroacetic acid, formic acid, stannic chloride, titanium tetrachloride, zinc chloride, zinc bromide, and boron trifluoride.

3. A method for preparing a cyclization product having a structure B

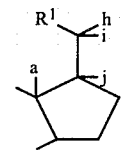

from a substrate having the structure A

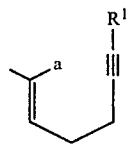

wherein:
a is hydrogen or lower alkyl of from 1 to 2 carbon atoms;
R¹ is hydrogen or saturated aliphatic hydrocarbon of from 1 to 3 carbon atoms and having from 0 to 1 oxy, halo or tri-(lower alkyl)silyl substituent;
h is derived from a nucleophile selected from the group consisting of alkenes, carbocyclic aromatics, oxy, halo, nitroalkane of from 1 to 6 carbon atoms and, when the nucleophile is hydroxy is taken together with i to form oxo;
when not taken together with h, i is taken together with j to form a double bond, and
j, when not taken together with i, is hydrogen or when h and i are oxo and said nucleophile is nitroalkane, oximino;
the method comprising:

contacting said substrate in a solvent containing said nucleophile with from about 1 to 50 equivalent of a Lewis acid per equivalent of said substrate at a temperature in the range of about −50° to 10° C.

4. A method according to claim 3, wherein said acid medium is derived from a protic acid.

5. A method according to claim 4, wherein said protic acid is a carboxylic acid and is said nucleophile.

6. A method according to claim 5, wherein the acid of said acidic medium is a Lewis acid metal halide.

7. A method for preparing a cyclization product having a structure B

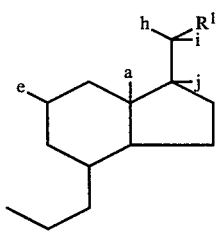

from a substrate having the structure A

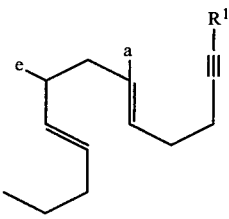

wherein:
a is hydrogen or lower alkyl of from 1 to 2 carbon atoms;
$R^1$ is hydrogen or saturated aliphatic hydrocarbon of from 1 to 3 carbon atoms and having 0 to 1 oxy, halo or tri-(lower alkyl) silyl substituent;
e is lower alkyl of from 1 to 2 carbon atoms;
h is derived from a nucleophile selected from the group consisting of alkenes, carbocyclic aromatics, oxy, halo, nitroalkane of from 1 to 6 carbon atoms, and, when the nucleophile is hydroxy is taken together with i to form oxo;
when not taken together with h, i is taken together with j to form a double bond; and
j when not taken together with i, is hydrogen or when h and i are oxo and said nucleophile is nitroalkane, oximino;
the method comprising:
contacting said substrate in an acidic halocarbon medium at a temperature in the range of about −50° to 10° C. with an acid at an equivalent ratio of 1-50:1 to said substrate in the presence of a nucleophile.

* * * * *